(12) United States Patent
Glunz et al.

(10) Patent No.: US 7,122,559 B2
(45) Date of Patent: Oct. 17, 2006

(54) PHENYLGLYCINE DERIVATIVES USEFUL AS SERINE PROTEASE INHIBITORS

(75) Inventors: Peter W. Glunz, Yardley, PA (US); Gregory S. Bisacchi, Ringoes, NJ (US); George C. Morton, Collegeville, PA (US); Alexandra A. Holubec, Yardley, PA (US); E. Scott Priestley, Yardley, PA (US); Xiaojun Zhang, Hockessin, DE (US); Uwe D. Treuner, Nittendorf (DE)

(73) Assignee: Bristol-Myers Squibb Company, Princeton, NJ (US)

( * ) Notice: Subject to any disclaimer, the term of this patent is extended or adjusted under 35 U.S.C. 154(b) by 115 days.

(21) Appl. No.: 10/775,923

(22) Filed: Feb. 10, 2004

(65) Prior Publication Data

US 2004/0204412 A1    Oct. 14, 2004

Related U.S. Application Data

(60) Provisional application No. 60/446,578, filed on Feb. 11, 2003, provisional application No. 60/520,781, filed on Nov. 17, 2003.

(51) Int. Cl.
*A61K 31/472* (2006.01)
*C07D 217/22* (2006.01)

(52) U.S. Cl. .................. 514/310; 546/143; 546/146; 546/139; 514/307

(58) Field of Classification Search ............... 514/310, 514/307; 546/143, 139, 146
See application file for complete search history.

(56) References Cited

U.S. PATENT DOCUMENTS

| | | | |
|---|---|---|---|
| 6,140,353 | A | 10/2000 | Ackermann et al. |
| 6,194,409 | B1 | 2/2001 | van Boeckel et al. |
| 6,242,644 | B1 | 6/2001 | Ackermann et al. |
| 6,335,324 | B1 | 1/2002 | Bisacchi et al. |
| 6,358,960 | B1 | 3/2002 | Senokuchi et al. |
| 6,472,393 | B1 | 10/2002 | Aliagas-Martin et al. |
| 6,642,252 | B1 | 11/2003 | Bisacchi et al. |
| 6,699,994 | B1 | 3/2004 | Babu et al. |

FOREIGN PATENT DOCUMENTS

| | | |
|---|---|---|
| WO | WO 96/20689 | 7/1996 |
| WO | WO 97/10214 | 3/1997 |
| WO | WO 01/44172 | 6/2001 |
| WO | WO 01/90051 | 11/2001 |
| WO | WO 02/09688 | 2/2002 |
| WO | WO 2002/034711 | 5/2002 |
| WO | WO 2003013531 | 2/2003 |
| WO | WO 03/66588 | 8/2003 |
| WO | WO 2003/084533 | 10/2003 |
| WO | WO2004/072102 | 8/2004 |

OTHER PUBLICATIONS

U.S. Appl. No. 10/775,443, filed Feb. 10, 2004, Bisacchi et al.
Stedman's Medical Dictionary, 27th Edition Illustrated in Color, Lippincott Williams & Wilkins, 1999, pp. 1711, 1831, 1832.
Dorland's Illustrated Medical Dictionary, 29th Edition, W.B. Saunders Company, 2000, pp. 1836, 1837.
Robbins Pathologic Basis of Disease, Sixth Edition, W. B. Saunders Company, 1999, pp. 113-138.
Hurst's The Heart, 10th Edition, 2001, pp. 1373-1384.
Harrison's Principles of Internal Medicine, 14th Edition, vol. 2, 1998, pp. 2325-2348.

*Primary Examiner*—Charanjit S. Aulakh
(74) *Attorney, Agent, or Firm*—Jing G. Sun

(57) ABSTRACT

Compounds having the formula (I),

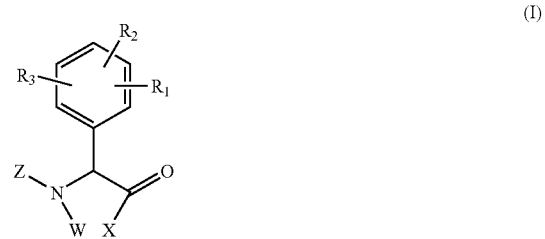

(I)

or a stereoisomer or pharmaceutically-acceptable salt, or hydrate thereof, are useful as factor VIIa inhibitors, wherein X is $-NR_6S(O)_pR_{16}$; W is hydrogen or $-(CR_7R_8)_q-W_1$; $W_1$ is hydrogen or a bond with $R_6$; Z is a 5-membered heteroaryl group, a five to six membered heterocyclo or cycloalkyl group, a 9 to 10 membered bicyclic aryl or heteroaryl, or a six membered aryl or heteroaryl, and $R_1$, $R_2$, $R_3$, $R_6$, $R_7$, and $R_{16}$ are as defined in the specification.

32 Claims, No Drawings

PHENYLGLYCINE DERIVATIVES USEFUL AS SERINE PROTEASE INHIBITORS

CROSS-REFERENCE TO RELATED APPLICATIONS

The present application claims the priority benefits of U.S. Provisional Application No. 60/446,578, filed Feb. 11, 2003, and U.S. Provisional Application No. 60/520,781, filed Nov. 17, 2003, which are expressly incorporated fully herein by reference.

FIELD OF THE INVENTION

The present invention relates to phenylglycine derivatives that are inhibitors of serine proteases such as Factor VIIa. These compounds are useful as anticoagulants in treating and preventing cardiovascular diseases, as anti-inflammatory agents, and as metastasis inhibitors in treating cancer.

BACKGROUND OF THE INVENTION

Under normal conditions, the coagulation system is naturally balanced in favor of anticoagulation by a number of proteins circulating in the blood. These proteins include antithrombin III, a serine-protease inhibitor, and protein C, a vitamin-K dependent protein formed in the liver. When injury or trauma occurs, thrombin is produced at precise levels through an ordered series of reactions. Thrombin is a proteolytic enzyme that occupies a central position in the coagulation process. Thrombin catalyzes the conversion of fibrinogen to fibrin, is a key effector enzyme for blood clotting, and is pivotal for other functions as well, such as activation of helper proteins (including Factors V and VIII and thrombomodulin), and its own activation. Disturbances in the natural balance between pro- and anti-coagulant forces may result in bleeding or thrombotic diseases.

A number of coagulation factors present in the blood as precursors (e.g., Factors VII–XII) lead to the production of thrombin. When the coagulation system is triggered (e.g., when trauma occurs), the coagulation factors are transformed into activated factors (e.g., Factors VIIa, IXa, Xa, XIa, etc.). When Factor VII is activated, it forms a complex with tissue factor, a membrane protein. Thus, Factor VIIa is present as a complex bound to tissue factor. When triggered, the coagulation factors and tissue factor complexes undergo an ordered chain of reactions that ultimately lead to conversion of Factor X to Factor Xa, and Factor Xa catalyzes the conversion of prothrombin to thrombin.

An elevated plasma level of coagulation factors, particularly Factor VIIa, is a risk factor for fatal myocardial infarction and associated with coronary artery disease and other abnormalities of the coagulation system, e.g., thrombosis, ischemic vascular disease, intravascular clotting, stroke, embolisms, and so forth. Accordingly, antithrombotic agents have been researched and developed for use in treating cardiovascular and other diseases. Presently established antithrombotic agents include heparin, coumarin, and aspirin. There are, however, limitations with these agents. For example, both heparin and coumarin have a highly-variable dose-related response, and their anticoagulant effects must be closely monitored to avoid a risk of serious bleeding. The erratic anticoagulant response of heparin is likely due to its propensity to bind non-specifically to plasma proteins. Aspirin has a limited efficacy and at high doses presents a risk of gastrointestinal bleeding. Thrombin inhibitors and their drawbacks are further discussed in WO 96/20689.

As may be appreciated, those in the field of pharmaceutical research continue to seek new compounds and compositions having increased effectiveness and bioavailability and/or having fewer side effects. There is particularly an interest in developing agents that can selectively and directly inhibit key factors in the complicated coagulation process. Compounds effective in inhibiting Factors VIIa, Xa, as well as tryptase and urokinase are described in U.S. Pat. No. 6,335,324 and U.S. Pat. No. 6,642,252. Factor VIIa inhibitors are also disclosed in U.S. Pat. No. 6,358,960 and WO 01/44172. U.S. Pat. No. 6,194,409 discloses certain bicyclic groups such as isoquinoline groups which reportedly are advantageous for promoting pharmacological properties. Phenyl glycine derivatives useful as serine protease inhibitors are disclosed in U.S. Pat. No. 6,140,353, U.S. Pat. No. 6,242,644, WO 01/90051 and WO 03/66588 and U.S. Pat. No. 6,472,393.

The patents, patent applications, and articles cited herewith are incorporated herein by reference.

SUMMARY OF THE INVENTION

Accordingly, the present invention provides novel compounds according to formula (I):

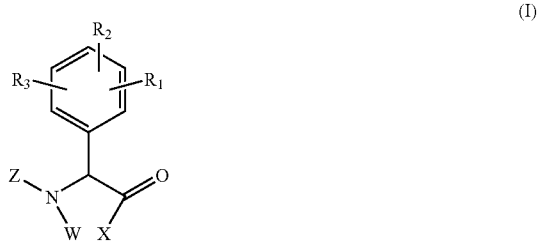

which are useful as selective inhibitors of serine protease enzymes, especially factor VIIa, or a stereoisomer or a pharmaceutically-acceptable salt, hydrate, or prodrug thereof, wherein:

X is $-NR_6S(O)_pR_{16}$;

W is hydrogen or $-(CR_7R_8)_q-W_1$;

$W_1$ is hydrogen or may be taken together with $R_6$ to define a bond so that X and W are joined together to form a five to seven membered heterocyclic ring;

Z is a 5-membered heteroaryl group optionally substituted with 1–3 $R_9$, a five to six membered heterocyclo or cycloalkyl group optionally substituted with 1–3 $R_9$, a 9 to 10 membered bicyclic aryl or heteroaryl optionally substituted with 1–3 substituents selected from $R_9$ and/or $R_{10}$, or

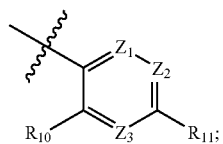

$Z_1$, $Z_2$ and $Z_3$ are independently N or $CR_9$;

$R_1$, $R_2$ and $R_3$ are attached to any available carbon atom of the phenyl ring and are independently selected from hydrogen, halogen, cyano, nitro, $C_{1-10}$alkyl, $C_{2-10}$alkenyl, substituted $C_{1-10}$alkyl, substituted $C_{2-10}$alkenyl, $-C(=O)NR_{12}R_{13}$, $-OR_{12}$, $-CO_2R_{12}$, $-C(=O)R_{12}$, $-SR_{12}$, $-S(O)_rR_{15}$, $-NR_{12}R_{13}$, $-NR_{12}SO_2R_{15}$, —$NR_{14}SO_2NR_{12}R_3$, —$NR_{12}CO_2R_{13}$, —$NR_{12}C(=O)R_{13}$, —$NR_{14}C(=O)NR_{12}R_{13}$, —$SO_2NR_{12}R_{13}$, aryl, heteroaryl, cycloalkyl, and heterocyclo;

$R_6$ is hydrogen, $C_{1-4}$alkyl, $NH_2$, $C_{1-4}$alkylamino, hydroxy, or $C_{1-4}$alkoxy, or together with $W_1$ is a bond so that X and W join together to form a five to seven membered heterocyclic ring;

$R_7$ and $R_8$ are independently selected from hydrogen, —$OR_{18}$, —$NR_{18}R_{19}$, —$NR_{18}SO_2R_{20}$, alkyl, alkenyl, substituted alkyl, substituted alkenyl, halogen, haloalkyl, haloalkoxy, cyano, nitro, alkylthio, —C(=O)H, acyl, —$CO_2H$, alkoxycarbonyl, sulfonamido, sulfonyl, and phenyl in turn optionally substituted with 1–3 of halogen, cyano, haloalkyl, haloalkoxy, nitro, hydroxy, $C_{1-4}$alkyl, $C_{1-4}$hydroxyalkyl, $C_{1-4}$alkoxy, amino, $NH(C_{1-4}$alkyl), $N(C_{1-4}$alkyl$)_2$, and/or $C_{1-4}$aminoalkyl;

$R_9$, $R_{10}$ and $R_{11}$ are independently selected from hydrogen, halogen, alkyl, substituted alkyl, haloalkyl, haloalkoxy, cyano, nitro, —$S(O)_uR_{21}$, —$NR_{22}SO_2R_{21}$, —C(=O)$NR_{22}R_{23}$, —$OR_{22}$, —$CO_2R_{22}$, —C(=O)$R_{22}$, —$SR_{22}$, —$NR_{22}R_{23}$, —$NR_{22}CO_2R_{23}$, —$NR_{22}C(=O)R_{23}$, —$NR_{22}C(=O)NR_{23}R_{24}$, —$SO_2NR_{22}R_{23}$, —$NR_{22}SO_2NR_{23}R_{24}$, —C(=$NR_{22}$)$NR_{23}R_{24}$, five or six membered heterocyclo or heteroaryl, phenyl, and $C_{3-7}$cycloalkyl, provided that $R_{11}$ is not —C(=$NR_{22}$)$NR_{23}R_{24}$ when W or $W_1$ is hydrogen; wherein when $R_9$, $R_{10}$ or $R_{11}$ is selected from heterocyclo, heteroaryl, phenyl, and $C_{3-7}$cycloalkyl, each of said cyclic groups in turn is optionally substituted with up to three of $C_{1-4}$alkyl, $C_{1-4}$alkoxy, $C_{1-4}$ hydroxyalkyl, $C_{1-4}$ aminoalkyl, halogen, hydroxy, haloalkyl, haloalkoxy, amino, $C_{1-4}$ alkylamino, and/or cyano;

$R_{12}$, $R_{13}$, $R_{14}$, $R_{18}$, $R_{19}$, $R_{22}$ $R_{23}$, and $R_{24}$ are independently selected from hydrogen, alkyl, substituted alkyl, alkenyl, substituted alkenyl, aryl, heteroaryl, cycloalkyl, and heterocyclo;

$R_{15}$, $R_{20}$ and $R_{21}$ are independently selected from alkyl, substituted alkyl, alkenyl, substituted alkenyl, aryl, heteroaryl, cycloalkyl, and heterocyclo;

$R_{16}$ is alkyl, substituted alkyl, alkenyl, substituted alkenyl, aryl, heteroaryl, cycloalkyl, or heterocyclo;

p is 1 or 2;

q is 1, 2 or 3;

t is 1 or 2; and u is 1 or 2;

provided that:

i) when Z is phenyl, pyridyl or pyridazinyl, $R_9$, $R_{10}$ and/or $R_{11}$ are other than cyano or —C(=$NR_{22}$)$NR_{23}R_{24}$;

ii) when W is H or $C_{1-4}$alkyl, Z is other than aryl;

iii) when W is H, Z is other than $C_{5-6}$cycloalkyl, piperidinyl, tetrahydropyridinyl, 3-pyridyl, or 3-pyridyl N-oxide; or iv) $R_1$, $R_2$, and $R_3$ are not all simultaneously hydrogen.

The invention also relates to pharmaceutical compositions containing at least one compound of formula (I) and a pharmaceutically-acceptable carrier or diluent, for use in treating serine protease or Factor VIIa-associated diseases. Also included within the invention are methods of treating such diseases comprising administering to a mammal in need of such treatment an effective amount of at least one compound of formula (I). Further included in the invention are compositions for use as anticoagulants during the preparation, use, storage, or fractionation of blood and methods of maintaining blood in the fluid phase during its preparation, use, storage or fractionation.

DETAILED DESCRIPTION OF THE INVENTION

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The following are definitions of terms used in this specification. The initial definition provided for a group or term herein applies to that group or term throughout the present specification, individually or as part of another group, unless otherwise indicated.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. When the subscript "0" is used, as in $C_0$, this refers to a bond. Thus, the term $C_{0-2}$hydroxyalkyl refers to hydroxy, hydroxymethyl, and hydroxyethyl.

The term "substituted alkyl" refers to an alkyl group as defined above having one, two, or three substituents selected from the group consisting of halogen, trifluoromethyl, alkenyl, alkynyl, nitro, cyano, keto (=O), haloalkoxy, —OR, —SR, —NRR', —NRSO$_2$, —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', =N—OH, =N—O-alkyl, aryl, heteroaryl, heterocyclo and cycloalkyl, wherein R and R' are selected from hydrogen, alkyl, alkenyl, amino, alkylamino, substituted alkylamino, benzyl, phenylethyl, cycloalkyl, heterocyclo, aryl, and heteroaryl, or R and R' together may form a heterocyclo or heteroaryl ring, and R" is alkyl, alkenyl, benzyl, phenylethyl, cycloalkyl, heterocyclo, aryl, and/or heteroaryl. When an alkyl is substituted with an aryl, heteroaryl, heterocyclo or cycloalkyl, those groups are as recited below and thus optionally may be substituted as recited below. Each of R, R', and R" in turn may have zero to three substituents (preferably 0–2 substituents), appropriately selected from R''', $C_{1-4}$ alkyl, and $C_{1-4}$alkyl substituted with R''', wherein R''' is selected from halogen, haloalkyl, $C_{2-5}$alkenyl, nitro, cyano, —OH, —O($C_{1-4}$alkyl), haloalkoxy, phenyl, benzyl, phenylethyl, phenyloxy, benzyloxy, —SH, —S($C_{1-4}$alkyl), —S(phenyl), —NH$_2$, —NH($C_{1-4}$alkyl), —N($C_{1-4}$alkyl)$_2$, —NH(cycloalkyl), —NHSO$_2$, —NHSO$_2$($C_{1-4}$alkyl), —SO$_2$ ($C_{1-4}$alkyl), —SO$_2$NH$_2$, —SO$_2$NH($C_{1-4}$alkyl), —SO$_2$N ($C_{1-4}$alkyl)$_2$, —CO$_2$H, —CO$_2$($C_{1-4}$alkyl), —C(=O)H, —C(=O) $C_{1-4}$alkyl, —C(=O)NH$_2$, —C(=O)NH($C_{1-4}$ alkyl), —C(=O)N($C_{1-4}$alkyl)$_2$, —OC(=O)$C_{1-4}$alkyl, —OC(=O)NH$_2$, —OC(=O)NH($C_{1-4}$alkyl), —OC(=O)N ($C_{1-4}$alkyl)$_2$, —NHC(=O)$C_{1-4}$alkyl, —NHCO$_2$($C_{1-4}$alkyl), $C_{3-7}$cycloalkyl, $C_{5-6}$heteoraryl, and $C_{4-7}$heterocyclo.

When the term alkyl is used as a suffix with a second named group, as in arylalkyl or cycloalkylalkyl, this refers to a substituted alkyl in which at least one of the substituents is the second named group. For example, the term arylalkyl includes benzyl and any other straight or branched chain alkyl having at least one aryl group attached at any point of the alkyl chain. Other substituents may be attached to the alkyl chain or the second named group. Such substituents may be selected as appropriate from the groups recited above in the definition of substituted alkyl and/or from those recited herein for the second named group.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene, these groups are substituted with one to three substitutents as defined above for alkyl groups. A substituted alkylene, alkenylene, or alkynylene may have a ringed substituent attached in a spiro fashion as in

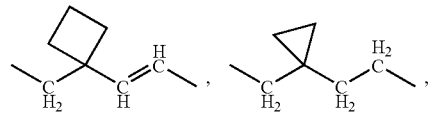

and so forth.

The term "alkoxy" refers to the group —OR, wherein R is alkyl or alkenyl. The term "alkylthio" refers to the group —SR, wherein R is alkyl or alkenyl. The term "alkylamino" refers to the group —NR'R", wherein each of R' and R" is selected from hydrogen, alkyl, alkenyl, cycloalkyl, aryl, heteroaryl, or heterocyclo, as defined herein, provided that both R' and R" are not hydrogen. The term "amino" refers to —NH$_2$. A substituted alkoxy, alkythio, or alkylamino may have zero to three substituents as defined above for substituted alkyl.

When a subscript is used with an alkoxy, alkylthio or alkylamino, the subscript refers to the number of carbon atoms that the group may contain in addition to heteroatoms. Thus, for example, monovalent $C_{1-2}$alkylamino includes the groups —NHCH$_3$, —NHCH$_2$CH$_3$, and —N(CH$_3$)$_2$. A lower alkylamino comprises an alkylamino having one to four carbon atoms.

The alkoxy, alkylthio, or alkylamino groups may be monovalent or bivalent. By "monovalent" it is meant that the group has a valency (i.e., power to combine with another group), of one, and by "bivalent" it is meant that the group has a valency of two. For example, a monovalent alkoxy includes groups such as —O—$C_{1-12}$alkyl, whereas a bivalent alkoxy includes groups such as —O—$C_{1-12}$alkylene-, etc.

The term "acyl" refers to a carbonyl {—C(=O)—} linked to an organic group i.e.,

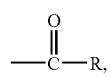

wherein R may be selected from alkyl, substituted alkyl, alkenyl, substituted alkenyl, aryl, heterocyclo, cycloalkyl, and heteroaryl, as defined herein.

The term "alkoxycarbonyl" refers to a carboxy or ester group {—CO$_2$—} linked to an organic radical, i.e.,

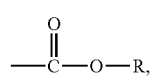

wherein R is as defined for acyl. "Carboxy" refers to the group CO$_2$H, and "carboxyalkyl" refers to —R—CO$_2$H, wherein R is alkylene or substituted alkylene.

The term "carbamyl" refers to a functional group in which a nitrogen atom is directly bonded to a carbonyl, i.e., as in —NRC(=O)R' or —C(=O)NRR', wherein R and R' can be hydrogen, alkyl, substituted alkyl, alkenyl, substituted alkenyl, alkoxy, cycloalkyl, aryl, heterocyclo, or heteroaryl.

The term "heteroatoms" shall include oxygen, sulfur and nitrogen.

"Halo" or "halogen" as used herein refers to fluoro, chloro, bromo, and iodo; and "counterion" is used to represent a small, negatively charged species such as chloride, bromide, hydroxide, acetate, and sulfate.

The term "haloalkyl" means an alkyl having one or more halo substituents and thus includes, for example, trifluoromethyl.

The term "perfluoroalkyl" means an alkyl group having from one to five fluoro atoms, such as pentafluoroethyl. The term "perfluoromethyl" means a methyl group substituted by one, two, or three fluoro atoms, i.e., —CH$_2$F, —CHF$_2$ and CF$_3$.

The term "haloalkoxy" means an alkoxy group having one or more halo substituents. For example, "haloalkoxy" includes —OCF$_3$.

The term "sulfonyl" refers to a sulphoxide group (i.e., —S(O)$_{1-3}$) linked to an organic radical R", wherein R" is alkyl, substituted alkyl, alkenyl, substituted alkenyl, cycloalkyl, heterocyclo, heteroaryl, or aryl. Sulfonic acid is —SO$_3$H.

The term "sulfonamide" or "sulfonamido" refers to the group —S(O)$_2$NRR', wherein R and R" are selected from hydrogen, alkyl, substituted alkyl, alkenyl, substituted alkenyl, cycloalkyl, heterocyclo, heteroaryl and aryl. Preferably when one of R and R' is, optionally substituted cycloalkyl, heterocyclo, heteroaryl or aryl (as defined below), the other of R and R' is hydrogen or alkyl.

The term "cycloalkyl" refers to fully saturated and partially unsaturated substituted or unsubstituted hydrocarbon rings of 3 to 9, preferably 3 to 7 carbon atoms. When substituted, the cycloalkyl will contain one to three (preferably one to two) groups selected from the group consisting of C$_{0-6}$alkyl optionally substituted with (or linked to) one to two of halogen, perfluoroalkyl, alkenyl, alkynyl, nitro, cyano, keto (=O), haloalkoxy, —OR, —SR, —NRR', —NRSO$_2$, —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', =N—OH, =N—O-alkyl, phenyl, 3 to 6 membered heteroaryl or heterocyclo, and/or C$_{3-7}$cycloalkyl, wherein R and R' are independently selected from hydrogen, alkyl, alkenyl, phenyl, benzyl, phenylethyl, C$_{3-7}$cycloalkyl, and 3 to 6 membered heterocyclo or heteroaryl, and R" is alkyl, alkenyl, phenyl, benzyl, phenylethyl, C$_{3-7}$cycloalkyl, and/or 3 to 6 membered heterocyclo or heteroaryl. The term "cycloalkyl" also includes such rings having a phenyl ring fused thereto or having a carbon-carbon bridge of 3 to 4 carbon atoms. Additionally, each of R, R' and R" in turn may, as appropriate, be optionally substituted with one to two C$_{0-4}$alkyl optionally substituted with (or linked to) one to two of halogen, CF$_3$, OCF$_3$, alkenyl, nitro, cyano, keto (=O), hydroxy, alkoxy, SH, S(alkyl), NH$_2$, NH(alkyl), N(alkyl)$_2$, CO$_2$H, CO$_2$(alkyl), C(=O)H, and/or C(=O)alkyl.

The term "aryl" refers to phenyl and naphthyl, with phenyl being preferred. The term "aryl" includes such rings having zero to three substituents (preferably 0–2 substituents). When substituted, the aryl will contain one to three C$_{0-6}$alkyl optionally substituted with (or linked to) one to two of halogen, perfluoroalkyl, alkenyl, alkynyl, nitro, cyano, haloalkoxy, —OR, —SR, —NRR', —NRSO$_2$, —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', phenyl, 3 to 6 membered heteroaryl or heterocyclo, and C$_{3-7}$cycloalkyl, wherein R and R' are independently selected from hydrogen, alkyl, alkenyl, phenyl, benzyl, phenylethyl, C$_{3-7}$cycloalkyl, or 3 to 6 membered heterocyclo and heteroaryl, and R" is alkyl, alkenyl, phenyl, benzyl, phenylethyl, C$_{3-7}$cycloalkyl, and/or 3 to 6 membered heterocyclo or heteroaryl. Additionally, two substituents attached to an aryl, particularly a phenyl group, may join to form a further ring including a spiro ring or a fused ring, e.g., spiro-cyclopentyl or fused cyclohexenyl, or fused heteroaryl or heterocyclo. Each of R, R', and R" in turn may, as appropriate, be optionally substituted with one to two C$_{0-4}$alkyl optionally substituted with (or linked to) one to two of halogen, CF$_3$, OCF$_3$, alkenyl, nitro, cyano, keto (=O), hydroxy, alkoxy, SH, S(alkyl), NH$_2$, NH(alkyl), N(alkyl)$_2$, CO$_2$H, CO$_2$(alkyl), C(=O)H, and/or C(=O) alkyl.

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms, provided that the total number of heteroatoms in each ring is four or less, and further provided that the ring contains at least one carbon atom and no two adjacent heteroatoms are simultaneously selected from —O— and —S—. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero to three substituents (preferably 0–2 substituents), selected from C$_{0-6}$alkyl optionally substituted with (or linked to) one to two of halogen, perfluoroalkyl, alkenyl, alkynyl, nitro, cyano, haloalkoxy, keto (=O), —OR, —SR, —NRR', —NRSO$_2$, —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', phenyl, 3 to 6 membered heteroaryl or heterocyclo, and/or C$_{3-7}$cycloalkyl, wherein R and R' are independently selected from hydrogen, alkyl, alkenyl, phenyl, benzyl, phenylethyl, C$_{3-7}$cycloalkyl, and 3 to 6 membered heterocyclo or heteroaryl, and R" is alkyl, alkenyl, phenyl, benzyl, phenylethyl, C$_{3-7}$cycloalkyl, or 3 to 6 membered heterocyclo or heteroaryl. The term "heterocyclo" also includes such rings having a phenyl ring fused thereto or having a carbon-carbon bridge of 3 to 4 carbon atoms. Additionally, each of R, R' and R" in turn may, as appropriate, be optionally substituted with one to two C$_{0-4}$alkyl optionally substituted with (or linked to) one to two of halogen, CF$_3$, OCF$_3$, alkenyl, nitro, cyano, keto (=O), hydroxy, alkoxy, SH, S(alkyl), NH$_2$, NH(alkyl), N(alkyl)$_2$, CO$_2$H, CO$_2$(alkyl), C(=O)H, and/or C(=O)alkyl.

Exemplary monocyclic groups include oxiranyl, aziridinyl, pyrrolidinyl, imidazolinyl, imidazolidinyl, pyrazolidinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, tetrahydropyranyl, morpholinyl, thiamorpholinyl, and the like. Exemplary bicyclic heterocyclo groups include quinuclidinyl.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms, provided that the total number of heteroatoms in each ring is four or less, each ring has at least one carbon atom, and no two adjacent heteroatoms are simultaneously selected from —O— and —S—. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring, but the other fused ring or rings may be aromatic or non-aromatic. The heteroaryl group may be attached at any available nitrogen or carbon atom of any ring. The heteroaryl ring system may contain zero to three substituents (preferably 0–2 substituents), selected from $C_{0-6}$alkyl optionally substituted with (or linked to) one to two of halogen, perfluoroalkyl, alkenyl, alkynyl, nitro, cyano, haloalkoxy, keto (=O), —OR, —SR, —NRR', —NRSO$_2$, —NRSO$_2$R', —SO$_2$R'', —SO$_2$NRR', —CO$_2$R, —C(=O)R, —C(=O)NRR', —OC(=O)R, —OC(=O)NRR', —NRC(=O)R', —NRCO$_2$R', phenyl, 3 to 6 membered heteroaryl or heterocyclo, and/or $C_{3-7}$cycloalkyl, wherein R and R' are independently selected from hydrogen, alkyl, alkenyl, phenyl, benzyl, phenylethyl, $C_{3-7}$cycloalkyl, and 3 to 6 membered heterocyclo or heteroaryl, and R'' is alkyl, alkenyl, phenyl, benzyl, phenylethyl, $C_{3-7}$cycloalkyl, and/or 3 to 6 membered heterocyclo or heteroaryl. Additionally, each of R, R' and R'' in turn may, as appropriate, be optionally substituted with one to two $C_{0-4}$alkyl optionally substituted with (or linked to) one to two of halogen, $CF_3$, $OCF_3$, alkenyl, nitro, cyano, keto (=O), OH, O(alkyl), phenyloxy, benzyloxy, SH, S(alkyl), $NH_2$, NH(alkyl), N(alkyl)$_2$, $CO_2H$, $CO_2$(alkyl), C(=O)H, and/or C(=O) alkyl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, indazolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, cinnolinyl, quinoxalinyl, indazolyl, pyrrolopyridyl, furopyridinyl, dihydroisoindolyl, benzothiadiazolyl, phthalazinyl, benzotriazinyl, quinazolinyl, quinolinyl, benzoxazolyl, benzothiopheneyl, tetrahydrophthalazinyl, tetrahydroquinolinyl, tetrahydroquinazolinyl, tetrahydrocinnolinyl, tetrahydroquinoxalinyl and the like.

Exemplary tricyclic heteroaryl groups include carbazolyl, benzidolyl, phenanthrollinyl, acridinyl, phenanthridinyl, xanthenyl and the like.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups, as appropriate.

"Protecting groups" may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Examples of amino protecting groups include, formyl, aralkyl groups (e.g., benzyl and substituted benzyl, p-methoxybenzyl, nitrobenzyl and 2,4-dimethoxybenzyl, and triphenylmethyl); di-p-anisylmethyl and furylmethyl groups: lower alkoxycarbonyl (for example tert-butoxycarbonyl): lower alkenyloxycarbonyl (for example allyloxycarbonyl): aryl lower alkoxycarbonyl groups (for example benzyloxycarbonyl, p-methoxybenzyloxycarbonyl, o-benzylidene and substituted benzylidene groups.

Methods appropriate for removal of amino protecting groups include, e.g., acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to *Advanced Organic Chemistry*, 4$^{th}$ Edition, by Jerry March, published by John Wiley & Sons 1992, for general guidance on reaction conditions and reagents. The reader is referred to *Protective Groups in Organic Synthesis*, 2$^{nd}$ Edition, by Green et al., published by John Wiley & Sons for general guidance on protecting groups.

Preferred leaving groups include halides, mesylate, tosylate, benzenesulfonate, trifluoromethanesulfonate, and the like and the methods to produce these intermediates will be readily recognized by those skilled in the art.

When the term "unsaturated" is used herein to refer to a ring or group, the ring or group may be fully unsaturated or partially unsaturated. Throughout the specification, groups and substituents thereof may be chosen by one skilled in the field to provide stable moieties and compounds. The terms "appropriately selected" are "appropriately substituted" as used herein are intended to mean that one skilled in the field would make selections from the recited groups to provide stable moieties and compounds.

The compounds of of the present inventions form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309–396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113–191 (1991);

c) H. Bundgaard, *Advanced Drug Delivery Reviews*, Vol. 8, p. 1–38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of solvation are generally known in the art.

Compounds of the present invention are, subsequent to their preparation, preferably isolated and purified to obtain a composition containing an amount by weight equal to or greater than 99% compound of the present invention ("substantially pure"), which is then used or formulated as described herein. Such "substantially pure" compounds are also contemplated herein as part of the present invention.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor VIIa. "Therapeutically effective amount" is also intended to include an amount of the combination of compounds claimed that is effective to inhibit factor VIIa. The combination of compounds is preferably a synergistic combination. Synergy, as described, for example, by Chou and Talalay, *Adv. Enzyme Regul.* 1984, 22:27–55, occurs when the effect (in this case, inhibition of factor VIIa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Preferred Embodiments

In a preferred embodiment, the present invention provides compounds of formula (I):

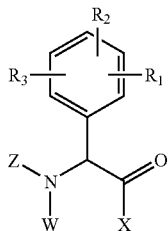

(I)

or a stereoisomer or a pharmaceutically-acceptable salt, hydrate or prodrug thereof, wherein:

X is —NR$_6$S(O)$_p$R$_{16}$;

W is hydrogen or —(CH$_2$)$_q$—H;

Z is a 5-membered heteroaryl group optionally substituted with 1–3 R$_9$, a five to six membered heterocyclo optionally substituted with 1–3 R$_9$, a 9 to 10 membered bicyclic heteroaryl optionally substituted with 1–3 substituents selected from R$_9$ and/or R$_{10}$, or

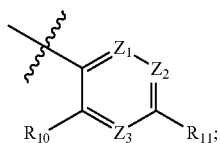

$Z_1$, $Z_2$ and $Z_3$ are independently N or CR$_9$ and at least one of $Z_1$, $Z_2$ and $Z_3$ is N;

R$_1$, R$_2$ and R$_3$ are attached to any available carbon atom of the phenyl ring and are independently selected from hydrogen, halogen, cyano, nitro, C$_{1-10}$alkyl, C$_{2-10}$alkenyl, substituted C$_{1-10}$alkyl, substituted C$_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_t$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, and heterocyclo;

R$_6$ is hydrogen;

R$_9$, R$_{10}$ and R$_{11}$ are independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and C$_{3-7}$cycloalkyl, provided that R$_{11}$ is not —C(=NR$_{22}$)NR$_{23}$R$_{24}$ when W or W$_1$ is hydrogen; wherein when R$_9$, R$_{10}$ or R$_{11}$ is selected from heterocyclo, heteroaryl, phenyl, and C$_{3-7}$cycloalkyl, each of said cyclic groups in turn is optionally substituted with up to three of C$_{1-4}$alkyl, C$_{1-4}$alkoxy, C$_{1-4}$ hydroxyalkyl, C$_{1-4}$ aminoalkyl, halogen, hydroxy, haloalkyl, haloalkoxy, amino, C$_{1-4}$ alkylamino, and/or cyano;

R$_{12}$, R$_{13}$, R$_{14}$, R$_{18}$, R$_{19}$, R$_{22}$ R$_{23}$, and R$_{24}$ are independently selected from hydrogen, alkyl, substituted alkyl, alkenyl, substituted alkenyl, aryl, heteroaryl, cycloalkyl, and heterocyclo;

R$_{15}$, R$_{20}$ and R$_{21}$ are independently selected from alkyl, substituted alkyl, alkenyl, substituted alkenyl, aryl, heteroaryl, cycloalkyl, and heterocyclo;

R$_{16}$ is alkyl, substituted alkyl, alkenyl, substituted alkenyl, aryl, heteroaryl, cycloalkyl, or heterocyclo;

p is 1 or 2;

q is 1, 2 or 3;

t is 1 or 2; and u is 1 or 2;

provided that:

i) when Z is pyridyl or pyridazinyl, R$_9$, R$_{10}$ and/or R$_{11}$ are other than cyano or —C(=NR$_{22}$)NR$_{23}$R$_{24}$;

ii) when W is H, Z is other than piperidinyl, tetrahydropyridinyl, 3-pyridyl, or 3-pyridyl N-oxide; or iii) R$_1$, R$_2$, and R$_3$ are not all simultaneously hydrogen.

More preferred are compounds wherein Z substituted by 0 to 3 R$_9$ and is selected from the group:

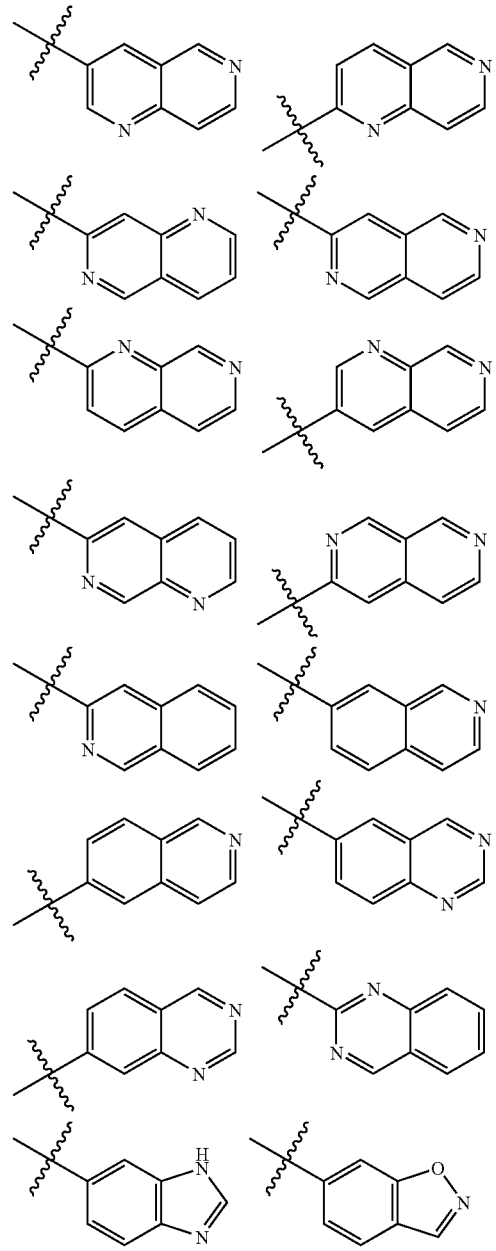

-continued
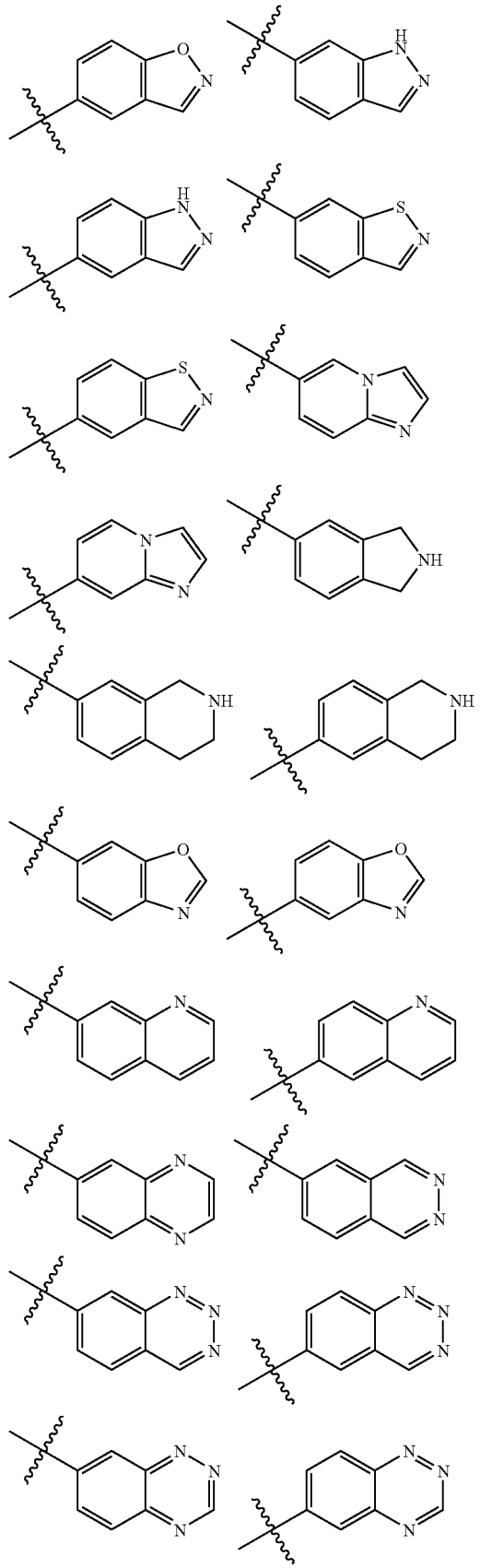
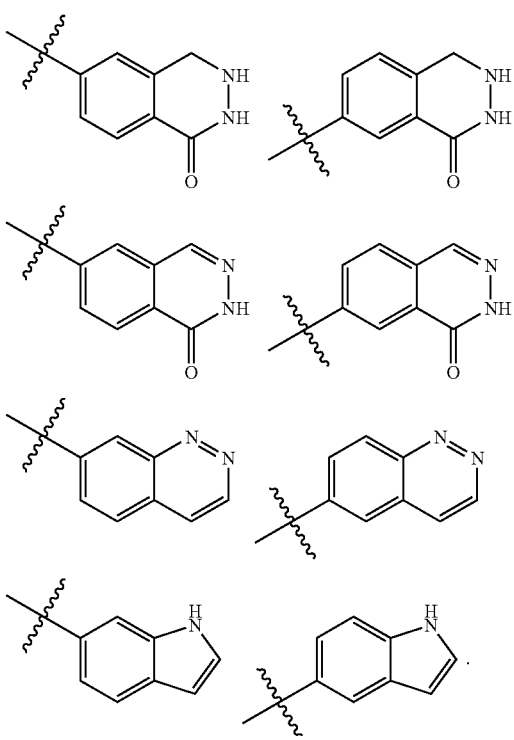
More preferred are compounds wherein Z is substituted with 0–2 $R_9$ and selected from the group:

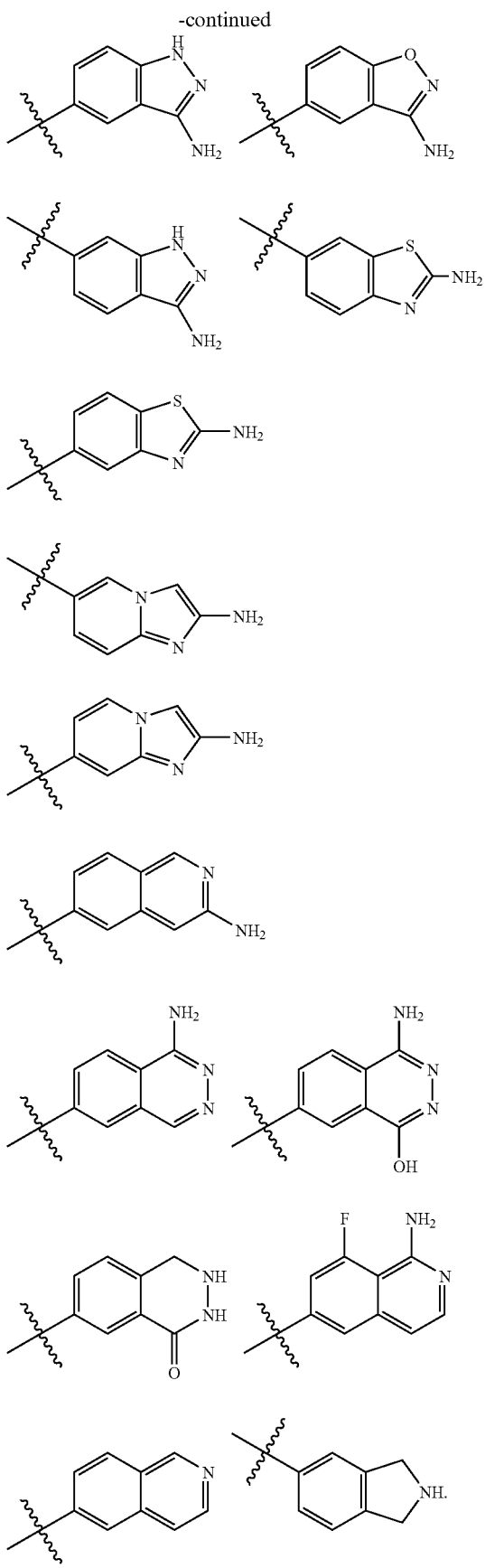

More preferred are compounds having the formula (Ia),

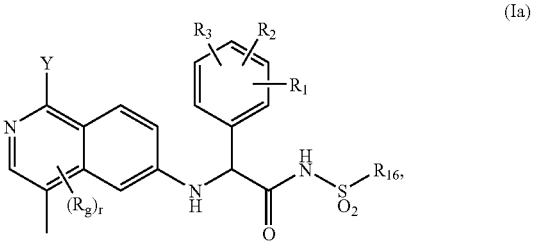

or a stereoisomer or a pharmaceutically-acceptable salt, hydrate, or prodrug thereof, wherein:

Y is $NH_2$ or H;

$R_1$, $R_2$ and $R_3$ are attached to any available carbon atom of the phenyl ring and are independently selected from H, halogen, CN, $NO_2$, $C_{1-6}$alkyl, $C_{2-6}$alkenyl, substituted $C_{1-6}$alkyl, substituted $C_{2-6}$alkenyl, —C(=O)$NR_{12}R_{13}$, —$OR_{12}$, —$CO_2R_{12}$, —C(=O)$R_{12}$, —$SR_{12}$, —S(O)$_tR_{15}$, —$NR_{12}R_{13}$, —$NR_{12}SO_2R_{15}$, —$NR_{14}SO_2NR_{12}R_{13}$, —$NR_{12}CO_2R_{13}$, —$NR_{12}C(=O)R_{13}$, —$NR_{14}C(=O)NR_{12}R_{13}$, —$SO_2NR_{12}R_{13}$, aryl, heteroaryl, cycloalkyl, and heterocyclo;

$R_9$ is, independently at each occurrence, H, halogen, alkyl, substituted alkyl, haloalkyl, haloalkoxy, cyano, nitro, —S(O)$_uR_{21}$, —$NR_{22}SO_2R_{21}$, —C(=O)$NR_{22}R_{23}$, —$OR_{22}$, —$CO_2R_{22}$, —C(=O)$R_{22}$, —$SR_{22}$, —$NR_{22}R_{23}$, —$NR_{22}CO_2R_{23}$, —$NR_{22}C(=O)R_{23}$, —$NR_{22}C(=O)NR_{23}R_{24}$, —$SO_2NR_{22}R_{23}$, —$NR_{22}SO_2NR_{23}R_{24}$, five or six membered heterocyclo or heteroaryl, phenyl, or $C_{3-7}$cycloalkyl, provided that $R_{11}$ is not —C(=$NR_{22}$)$NR_{23}R_{24}$ when W or $W_1$ is hydrogen; wherein when $R_9$ is selected from heterocyclo, heteroaryl, phenyl, and $C_{3-7}$cycloalkyl, each of said cyclic groups in turn is optionally substituted with up to three of $C_{1-4}$alkyl, $C_{1-4}$alkoxy, $C_{1-4}$ hydroxyalkyl, $C_{1-4}$ aminoalkyl, halogen, hydroxy, haloalkyl, haloalkoxy, amino, $C_{1-4}$ alkylamino, and/or cyano;

$R_{16}$ is $C_{1-6}$alkyl substituted with 0–3 $R_{25}$, phenyl substituted 0–3 $R_{25}$, naphthyl substituted with 0–3 $R_{25}$, a 5–10 membered heteroaryl substituted with 0–3 $R_{25}$ and selected from 1H-pyrazol-4-yl, 1H-pyrazol-4-yl, thiazol-5-yl, 2-naphthyl, quinolin-8-yl, benzo[1,2,5]thiadiazol-4-yl, 2,3-dihydro-benzo[1,4]dioxin-5-yl, or 1H-benzoimidazol-5-yl;

$R_{25}$ is, independently at each occurrence, $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, cyano, carboxy, nitro, phenyl; —$SO_2NR_{22}R_{23}$, or —CO$NR_{22}R_{23}$; and r is 0 to 2.

More preferred are compounds having the formula (Ib),

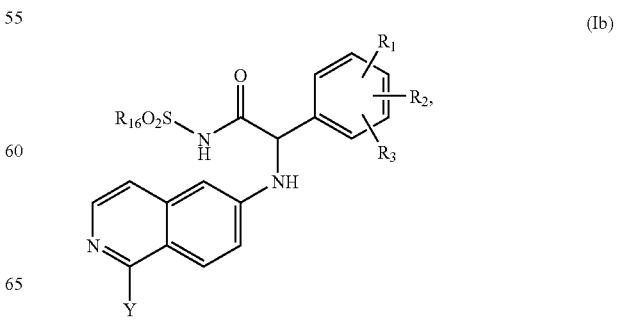

or a stereoisomer or a pharmaceutically-acceptable salt, hydrate, or prodrug thereof, wherein:

Y is H or $NH_2$;

$R_{16}$ is Me, Et, Pr, i-Pr, cyclo-Pr, Bu, i-Bu, t-Bu, phenyl, 2-Me-phenyl, 3-Me-phenyl, 4-Me-phenyl, 2-F-phenyl, 3-F-phenyl, 4-F-phenyl, 2-OH-phenyl, 3-OH-phenyl, 4-OH-phenyl, 2-OMe-phenyl, 3-OMe-phenyl, 4-OMe-phenyl, 2-$CH_2$OH-phenyl, 3-$CH_2$OH-phenyl, 4-$CH_2$OH-phenyl, 2-$CO_2$H-phenyl, 3-$CO_2$H-phenyl, 4-$CO_2$H-phenyl, 3-$CONH_2$-phenyl, 4-$CONH_2$-phenyl, 3-$CO_2$H-4-OH-phenyl, 3-$SO_2NH_2$-phenyl, 4-$SO_2NH_2$-phenyl, 2-CN-phenyl, 3-CN-phenyl, 4-CN-phenyl, 3-$NO_2$-phenyl, 4-$NO_2$-phenyl, 2-$NH_2$-phenyl, 3-$NH_2$-phenyl, 4-$NH_2$-phenyl, 3-$CH_2NH_2$-phenyl, 4-$CH_2NH_2$-phenyl, 4-(2-$CH_2CH_2NH_2$)-phenyl, 4-(2-tert-butyl carbamoyl-ethyl)-phenyl, benzyl, 5-Cl-1,3-diMe-1H-pyrazol-4-yl, 5-Me-1-phenyl-1H-pyrazol-4-yl, 2,4-diMe-thiazol-5-yl, 2-naphthyl, Quinolin-8-yl, Benzo[1,2,5]thiadiazol-4-yl, 2,3-dihydro-benzo[1,4]dioxin-5-yl, 2-amino-1H-benzoimidazol-5-yl, hydroxymethyl, hydroxyethyl, hydroxypropyl, aminomethyl, aminoethyl, aminopropyl, 2,2,2-trifluoroethyl, 3-$SO_2NH_2$-propyl, 3-$CONH_2$-propyl, 2-$SO_2NH_2$-ethyl, 2-$CONH_2$-ethyl, 4-$SO_2NH_2$-butyl, or 4-$CONH_2$-butyl.

In another more preferred embodiment, the present invention provides compounds of formula (Ib) as recited above, or a stereoisomer or a pharmaceutically-acceptable salt, hydrate, or prodrug thereof, wherein $R_1$ and $R_2$ are $C_{1-4}$alkoxy.

In another preferred embodiment, the present invention provides compounds of formula (I) as recited above, or a stereoisomer or a pharmaceutically-acceptable salt, hydrate, or prodrug thereof, wherein:

Z is selected from:

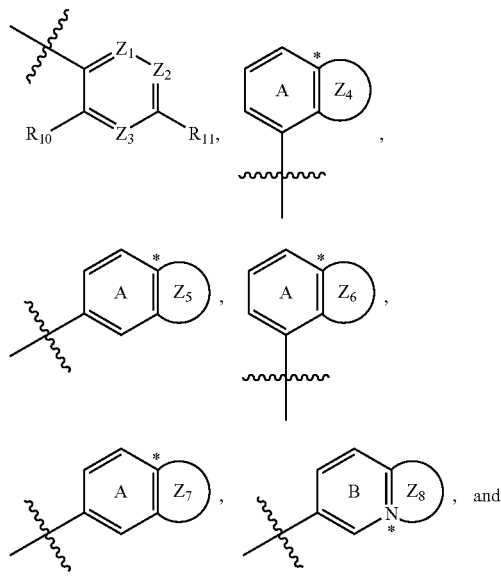

$Z_4$ is fused to ring A comprising the common carbon atom C* and is

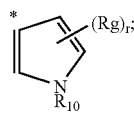

$Z_5$ is fused to ring A comprising the common carbon atom C* and is selected from:

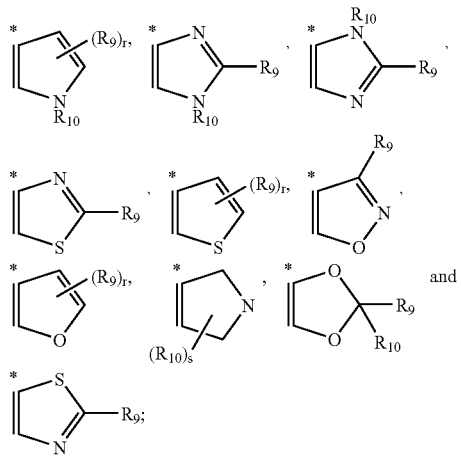

$Z_6$ is fused to ring A comprising the common carbon atom C* and is

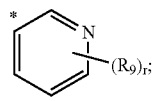

$Z_7$ is fused to ring A comprising the common carbon atom C* and is selected from:

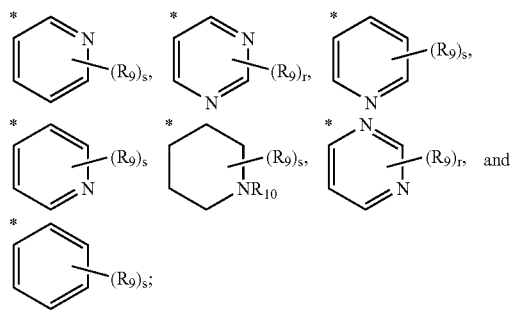

$Z_8$ is fused to ring B comprising the common nitrogen atom N* and is selected from

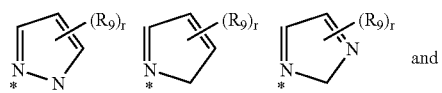

-continued
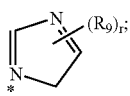
$Z_9$ is CH or N;
r is 0, 1, or 2; and
s is 0, 1, 2, or 3.
In another more preferred embodiment, the present invention provides compounds of formula (I) as recited above, or a stereoisomer or a pharmaceutically-acceptable salt, hydrate, or prodrug thereof, wherein:
Z is selected from:
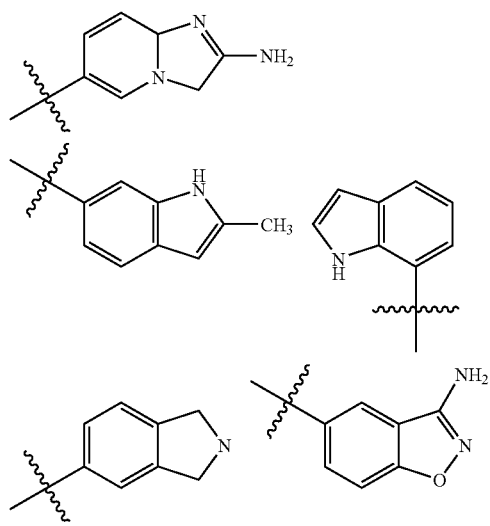
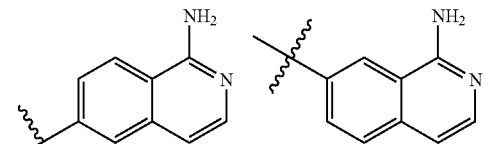
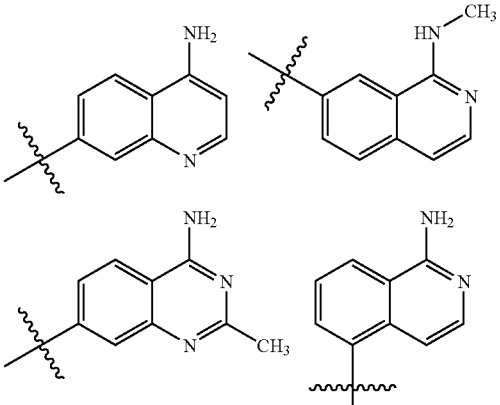
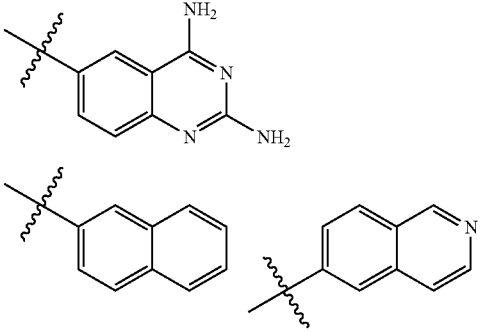
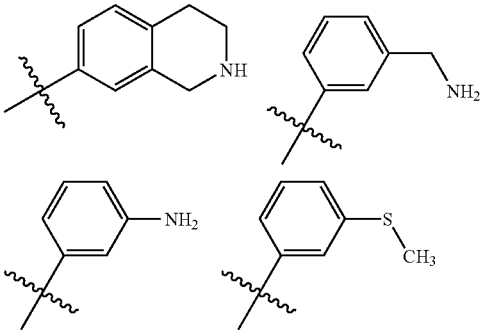
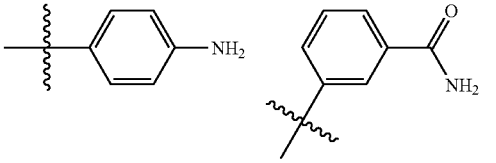
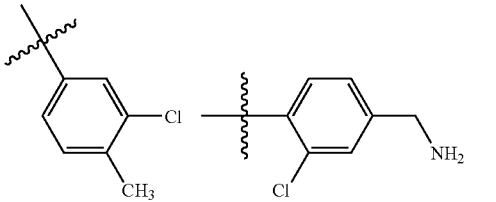

-continued

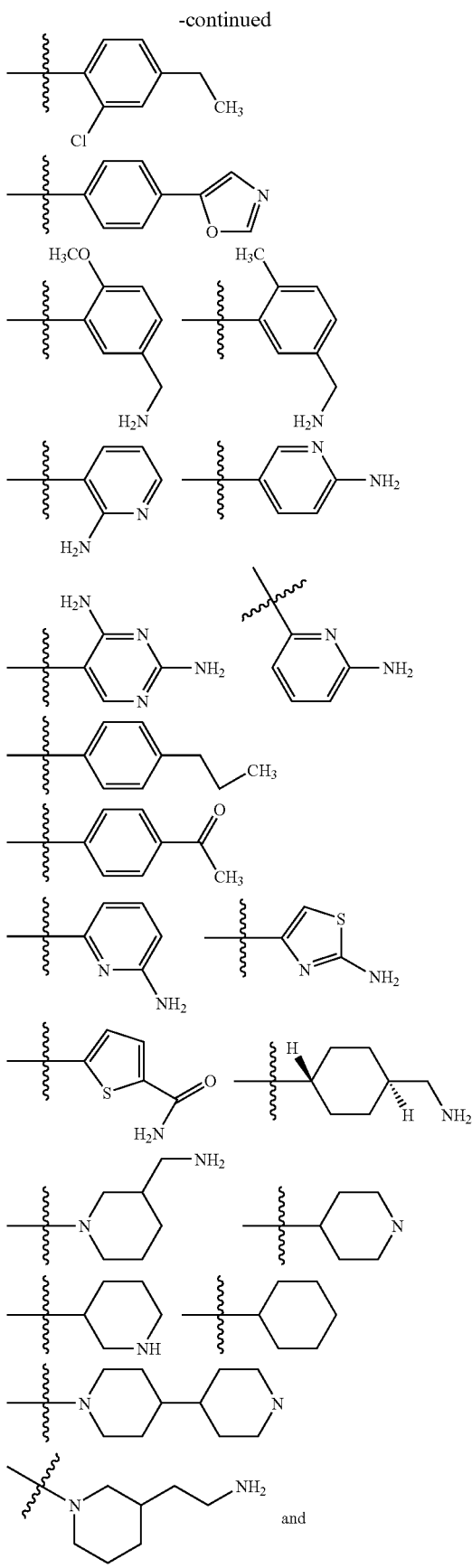

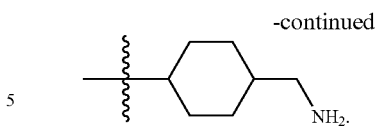

and

In another more preferred embodiment, the present invention provides compounds of formula (I) as recited above, or a stereoisomer or a pharmaceutically-acceptable salt, hydrate, or prodrug thereof, wherein $R_1$ and $R_2$ are $OR_{12}$.

In another more preferred embodiment, the present invention provides compounds of formula (I) as recited above, or a stereoisomer or a pharmaceutically-acceptable salt, hydrate, or prodrug thereof, wherein $R_{12}$ is $C_{1-6}$alkyl, phenyl, or benzyl optionally substituted with 1–2 of halogen, cyano, haloalkyl, haloalkoxy, nitro, hydroxy, $C_{1-4}$alkyl, $C_{1-4}$hydroxyalkyl, $C_{1-4}$alkoxy, amino, $NH(C_{1-4}$alkyl), and/or $N(C_{1-4}$alkyl$)_2$.

In another more preferred embodiment, the present invention provides compounds of formula (I) as recited above, or a stereoisomer or a pharmaceutically-acceptable salt, hydrate, or prodrug thereof, wherein W is hydrogen.

In another preferred embodiment, the present invention provides compounds of formula (Ic):

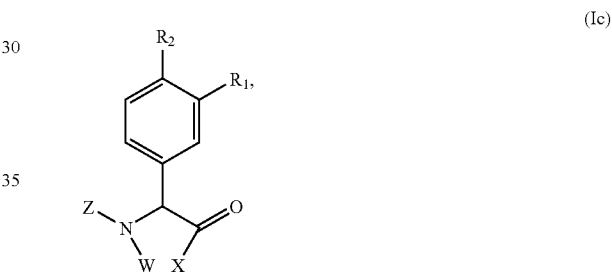

(Ic)

or a stereoisomer or a pharmaceutically-acceptable salt, hydrate, or prodrug thereof, wherein:

X is $-NR_6S(O)_pR_{16}$;

W is hydrogen or $-(CH_2)_q-H$;

Z is a 5-membered heteroaryl group optionally substituted with 1–2 $R_9$, a five to six membered heterocyclo or cycloalkyl group optionally substituted with 1–2 $R_9$, a 9 to 10 membered bicyclic aryl or heteroaryl optionally substituted with 1–3 substituents selected from $R_9$ and/or $R_{10}$, or

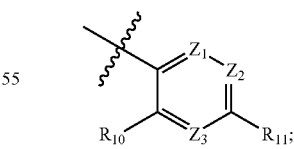

$Z_1$, $Z_2$ and $Z_3$ are independently N or $CR_9$ and at least one of $Z_1$, $Z_2$ and $Z_3$ is N;

$R_1$ and $R_2$ are attached to any available carbon atom of the phenyl ring and are independently hydrogen, halogen, cyano, nitro, $C_{1-10}$alkyl, $C_{2-10}$alkenyl, substituted $C_{2-10}$alkyl, substituted $C_{2-10}$alkenyl, $-C(=O)NR_{12}R_{13}$, $-OR_{12}$, $-CO_2R_{12}$, $-C(=O)R_{12}$, $-SR_{12}$, $-S(O)_rR_{15}$, $-NR_{12}R_{13}$, $-NR_{12}SO_2R_{15}$, $-NR_{14}SO_2NR_{12}R_{13}$, —NR$_{12}$CO$_2$R$_{13}$, —NR$_{12}$C(=O)R$_{13}$, —NR$_{14}$C(=O)NR$_{12}$R$_{13}$—SO$_2$NR$_{12}$R$_{13}$, aryl, heteroaryl, cycloalkyl, or heterocyclo;

R$_6$ is hydrogen or together with W is a bond so that X and W join together to form a five to seven membered heterocyclic ring;

R$_9$, R$_{10}$ and R$_{11}$ are independently selected from hydrogen, halogen, alkyl, substituted alkyl, haloalkyl, haloalkoxy, cyano, nitro, —S(O)$^u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and C$_{3-7}$cycloalkyl, provided that R$_{11}$ is not —C(=NR$_{22}$)NR$_{23}$R$_{24}$; wherein when R$_9$, R$_{10}$ or R$_{11}$ is selected from heterocyclo, heteroaryl, phenyl, and C$_{3-7}$cycloalkyl, each of said cyclic groups in turn is optionally substituted with up to three of C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

R$_{12}$, R$_{13}$, R$_{14}$, R$_{22}$ R$_{23}$, and R$_{24}$ are independently selected from hydrogen, alkyl, substituted alkyl, alkenyl, substituted alkenyl, aryl, heteroaryl, cycloalkyl, and heterocyclo;

R$_{15}$ and R$_{21}$, are independently selected from alkyl, substituted alkyl, alkenyl, substituted alkenyl, aryl, heteroaryl, cycloalkyl, and heterocyclo;

R$_{16}$ is C$_{1-6}$alkyl substituted with 0–2 R$_{25}$, phenyl substituted 0–3 R$_{25}$, naphthyl substituted with 0–3 R$_{25}$, a 5–10 membered heteroaryl substituted with 0–3 R$_{25}$ and selected from 1H-pyrazol-4-yl, 1H-pyrazol-4-yl, thiazol-5-yl, 2-naphthyl, quinolin-8-yl, benzo[1,2,5]thiadiazol-4-yl, 2,3-dihydro-benzo[1,4]dioxin-5-yl, or 1H-benzoimidazol-5-yl;

R$_{25}$ at each occurrence is selected from C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

p is 1 or 2;
q is 1, 2 or 3;
t is 1 or 2; and
u is 1 or 2;

provided that when Z is pyridyl or pyridazinyl, R$_9$, R$_{10}$ and/or R$_{11}$ are other than cyano or —C(=NR$_{22}$)NR$_{23}$R$_{24}$.

More preferred are compounds having the formula (Id),

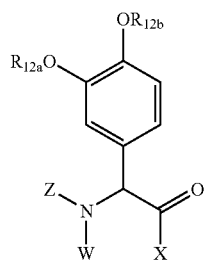

(Id)

or a stereoisomer or a pharmaceutically-acceptable salt, hydrate, or prodrug thereof, wherein:

X is —NR$_6$S(O)$_p$R$_{16}$;
W is hydrogen or —(CH$_2$)$_q$—W$_1$;
W$_1$ is hydrogen or may be taken together with R$_6$ to define a bond so that X and W are joined together to form a five to seven membered heterocyclic ring;

Z is selected from:

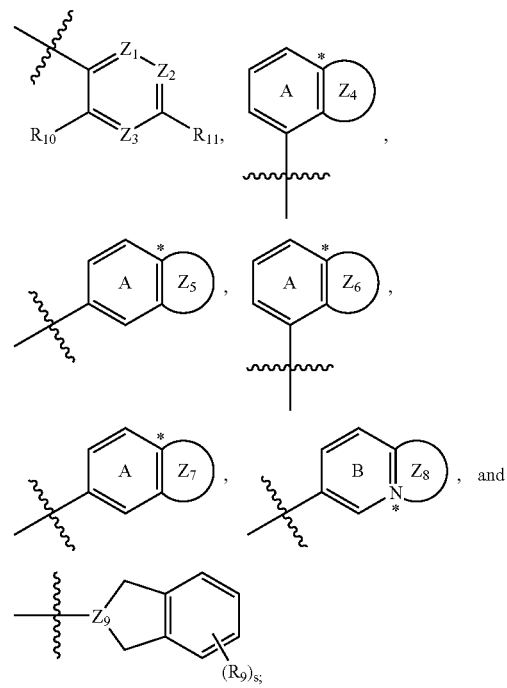

Z$_1$, Z$_2$ and Z$_3$ are independently N or CR$_9$;

Z$_4$ is fused to ring A comprising the common carbon atom C* and is

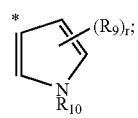

Z$_5$ is fused to ring A comprising the common carbon atom C* and is selected from:

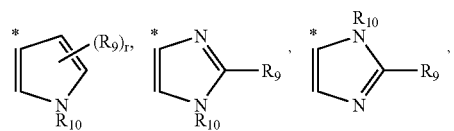

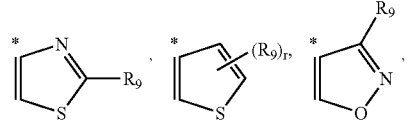

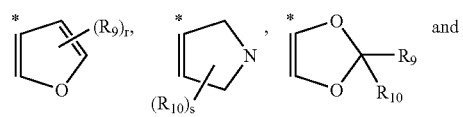

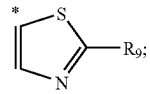

$Z_6$ is fused to ring A comprising the common carbon atom C* and is

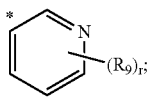

$Z_7$ is fused to ring A comprising the common carbon atom C* and is selected from:

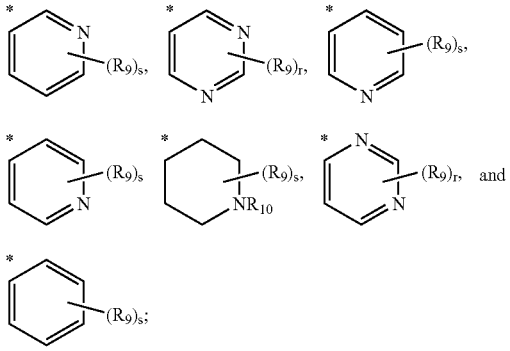

$Z_8$ is fused to ring B comprising the common nitrogen atom N* and is selected from

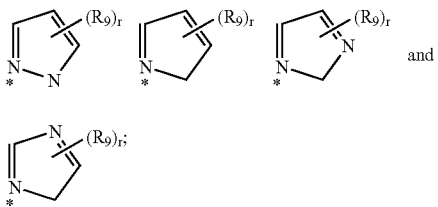

$Z_9$ is CH or N;

$R_6$ is hydrogen or together with $W_1$ is a bond so that X and W join together to form a five to seven membered heterocyclic ring;

$R_9$, $R_{10}$ and $R_{11}$ are independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and $C_{3-7}$cycloalkyl, provided that $R_9$, $R_{10}$, and $R_{11}$ are not —C(=NR$_{22}$)NR$_{23}$R$_{24}$ when W or $W_1$ is hydrogen; wherein when $R_9$, $R_{10}$ or $R_{11}$ is independently selected from heterocyclo, heteroaryl, phenyl, and $C_{3-7}$cycloalkyl, each of said cyclic groups in turn is optionally substituted with up to three of $C_{1-4}$alkyl, $C_{1-4}$alkoxy, $C_{1-4}$hydroxyalkyl, $C_{1-4}$aminoalkyl, halogen, hydroxy, haloalkoxy, amino, $C_{1-4}$alkylamino, and/or cyano;

$R_{12}$, $R_{12a}$, $R_{12b}$, $R_{22}$, $R_{23}$, and $R_{24}$ are independently selected from hydrogen, alkyl, substituted alkyl, alkenyl, substituted alkenyl, aryl, heteroaryl, cycloalkyl, and heterocyclo;

$R_{16}$ is $C_{1-6}$alkyl substituted with 0–2 $R_{25}$, phenyl substituted 0–3 $R_{25}$, naphthyl substituted with 0–3 $R_{25}$, a 5–10 membered heteroaryl substituted with 0–3 $R_{25}$ and selected from 1H-pyrazol-4-yl, 1H-pyrazol-4-yl, thiazol-5-yl, 2-naphthyl, quinolin-8-yl, benzo[1,2,5]thiadiazol-4-yl, 2,3-dihydro-benzo[1,4]dioxin-5-yl, or 1H-benzoimidazol-5-yl; and $R_{21}$ is selected from alkyl, substituted alkyl, alkenyl, substituted alkenyl, aryl, heteroaryl, cycloalkyl, and heterocyclo;

$R_{25}$ at each occurrence is selected from $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, and/or cyano;

p is 1 or 2;

q is 1, 2 or 3;

r is 0, 1, or 2;

s is 0, 1, 2, or 3;

t is 1 or 2; and u is 1 or 2.

provided that:

i) when Z is phenyl, pyridyl or pyridazinyl, $R_9$, $R_{10}$ and/or $R_{11}$ are other than cyano or —C(=NR$_{22}$)NR$_{23}$R$_{24}$;

ii) when W is H or $C_{1-4}$alkyl, Z is other than aryl.

In another preferred embodiment, the present invention provides compounds of formula (Ie):

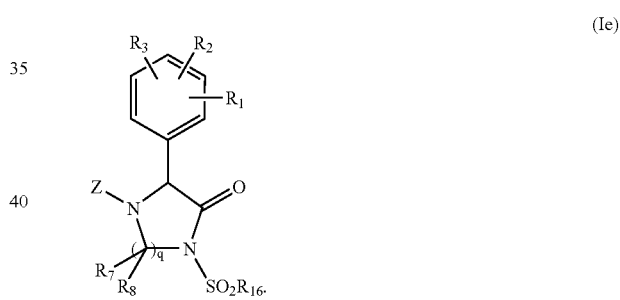

In another preferred embodiment, the present invention provides compounds of formula (If):

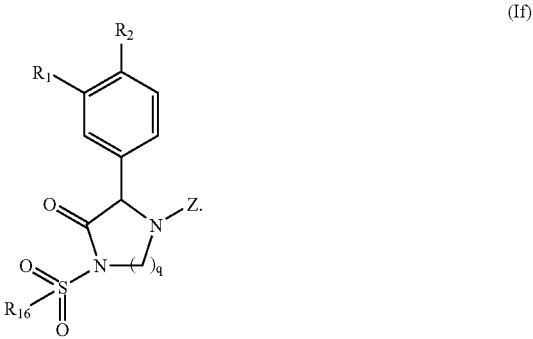

In another preferred embodiment, the present invention provides a process for preparing a compound of formula (I), which comprises:

(a) contacting a compound of formula (II):

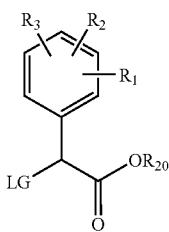

(II)

wherein $R_1$, $R_2$, and $R_3$ are defined as in Claim 1; LG is a leaving group selected from the group: halogen, mesylate, tosylate, benzenesulfonate, and trifluoromethanesulfonate; and $R_{20}$ is $C_{1-4}$alkyl or benzyl, with a compound of formula (III):

PG-Z-NH—W    (III)

wherein Z and W are defined as in Claim 1; and PG is a protecting group selected from the group: formyl, benzyl, p-methoxybenzyl, nitrobenzyl, 2,4-dimethoxybenzyl, triphenylmethyl, di-p-anisylmethyl, furylmethyl, $C_{1-4}$alkoxycarbonyl, $C_{1-4}$ allyloxycarbonyl, benzyloxycarbonyl, p-methoxybenzyloxycarbonyl, o-nitrobenzyloxycarbonyl, p-nitrobenzyloxycarbonyl, trimethylsilyl, t-Bu-diMe-silyl, $C_{1-4}$alkylidene, and benzylidene;

in the presence of a blase selected from the group: diisopropylethylamine, triethylamine, potassium carbonate, potassium bicarbonate, and potassium phosphate;

to form a compound of formula (IV):

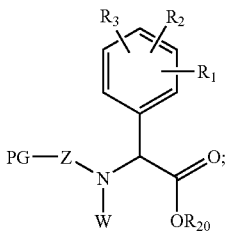

(IV)

and (c) forming a compound of formula (I).

In another preferred embodiment, the present invention provides a process for preparing a compound of formula (Ia), which comprises:

(a) contacting a compound of formula (II):

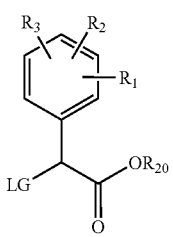

(II)

wherein $R_1$, $R_2$, and $R_3$ are defined as in Claim 5; LG is a leaving group selected from the group: halogen, mesylate, tosylate, benzenesulfonate, and trifluoromethanesulfonate; and $R_{20}$ is $C_{1-4}$alkyl or benzyl;

with a compound of formula (IIIa):

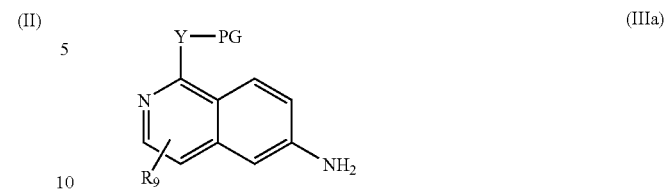

(IIIa)

wherein Y and $R_9$ are defined as in Claim 5; and PG is a protecting group selected from the group: formyl, benzyl, p-methoxybenzyl, nitrobenzyl, 2,4-dimethoxybenzyl, triphenylmethyl, di-p-anisylmethyl, furylmethyl, $C_{1-4}$alkoxycarbonyl, $C_{1-4}$ allyloxycarbonyl, benzyloxycarbonyl, p-methoxybenzyloxycarbonyl, o-nitrobenzyloxycarbonyl, p-nitrobenzyloxycarbonyl, trimethylsilyl, t-Bu-diMe-silyl, $C_{1-4}$alkylidene, and benzylidene;

in the presence of a base selected from the group: diisopropylethylamine, triethylamine, potassium carbonate, potassium bicarbonate, and potassium phosphate;

to form a compound of formula (IVa):

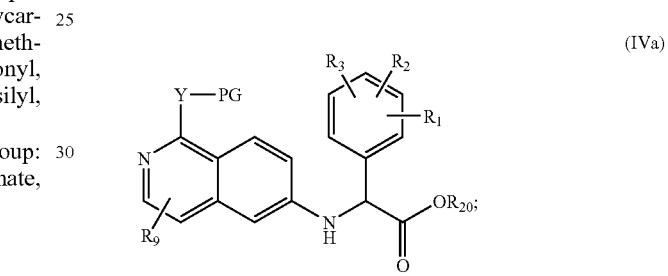

(IVa)

and (c) forming a compound of formula (Ia).

In another preferred embodiment, the present invention provides a process a compound of formula (Ia), which comprises:

contacting a compound of formula (II), wherein $R_{20}$ is benzyl; with

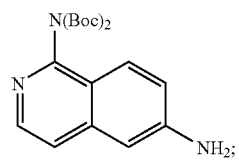

in the presence of diisopropyl ethyl amine;

to form a compound of formula of (IVb):

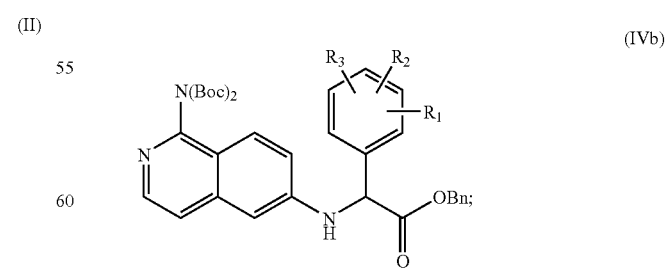

(IVb)

and (c) forming a compound of formula (Ia).

In another preferred embodiment, the present invention provides a process a compound of formula (I), which comprises:

(a) contacting a compound of formula (V):

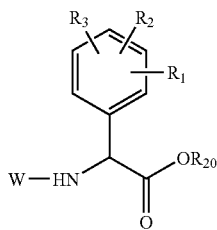

(V)

wherein $R_1$, $R_2$, $R_3$, and W are defined as in Claim 1; and $R_{20}$ is $C_{1-4}$alkyl or benzyl;

with a compound of formula (VI):

PG-Z-LG (VI)

wherein Z is defined as in Claim 1; PG is a protecting group selected from the group: formyl, benzyl, p-methoxybenzyl, nitrobenzyl, 2,4-dimethoxybenzyl, triphenylmethyl, di-p-anisylmethyl, furylmethyl, $C_{1-4}$alkoxycarbonyl, $C_{1-4}$ allyloxycarbonyl, benzyloxycarbonyl, p-methoxybenzyloxycarbonyl, o-nitrobenzyloxycarbonyl, p-nitrobenzyloxycarbonyl, trimethylsilyl, t-Bu-diMe-silyl, $C_{1-4}$alkylidene, and benzylidene; and LG is a leaving group selected from the group: halogen, mesylate, tosylate, benzenesulfonate, and trifluoromethanesulfonate;

in the presence of a palladium catalyst selected from the group: palladium (II) chloride, palladium (II) acetate, tris(dibenzylideneacetone)dipalladium (0), tetrakis(triphenylphosphine)palladium (0), bis(tri-t-butylphosphine)palladium(0), and allylpalladium chloride dimer; or a copper catalyst selected from the group: copper (III) triflate, tetrakis(acetonitrile)copper(I), hexafluorophosphate, copper(I) iodide, and copper (II) acetate; a ligand selected from the group: 1,1'-bis(diphenylphosphino)ferrocene, (R or S)-1-(2-diphenylphosphino-1-napthyl)isoquinoline, triphenylphosphine, triphenylarsine, 1,3-bis(2,4,6-trimethylphenyl)imidazolium chloride, tri-t-butylphosphine, tri-2-furylphosphine, (R or S)-2,2'-bis(diphenylphosphino)-1,1'-binapthyl (BINAP), (R or S)-2,2'-bis(di-p-tolylphosphino)-1,1'-binapthyl (Tol-BINAP), and N,N-diethlysalicylamide; and a base selected from potassium carbonate, potassium t-butoxide, tetrabutylammonium hydroxide, triethylamine, diisopropylethylamine, cesium carbonate, cesium acetate, and potassium phosphate;

to form a compound of formula (IV):

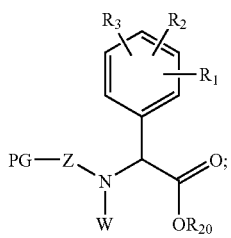

(IV)

and (c) forming a compound of formula (I).

In another preferred embodiment, the present invention provides a process a compound of formula (Ia), which comprises:

(a) contacting a compound of formula (Va):

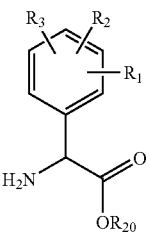

(Va)

wherein $R_1$, $R_2$, and $R_3$, are defined as in Claim 5; and $R_{20}$ is $C_{1-4}$alkyl or benzyl;

with a compound of formula (IIIa):

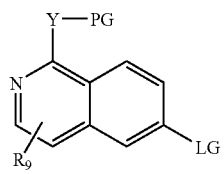

(IIIa)

wherein Y and $R_9$ are defined as in Claim 5; PG is a protecting group selected from the group: formyl, benzyl, p-methoxybenzyl, nitrobenzyl, 2,4-dimethoxybenzyl, triphenylmethyl, di-p-anisylmethyl, furylmethyl, $C_{1-4}$alkoxycarbonyl, $C_{1-4}$ allyloxycarbonyl, benzyloxycarbonyl, p-methoxybenzyloxycarbonyl, o-nitrobenzyloxycarbonyl, p-nitrobenzyloxycarbonyl, trimethylsilyl, t-Bu-diMe-silyl, $C_{1-4}$alkylidene, and benzylidene; and LG is a leaving group selected from the group: halogen, mesylate, tosylate, benzenesulfonate, and trifluoromethanesulfonate;

in the presence of a palladium catalyst selected from the group: palladium (II) chloride, palladium (II) acetate, tris(dibenzylideneacetone)dipalladium (0), tetrakis(triphenylphosphine)palladium (0), bis(tri-t-butylphosphine)palladium(0), and allylpalladium chloride dimer; or a copper catalyst selected from the group: copper (III) triflate, tetrakis(acetonitrile)copper(I), hexafluorophosphate, copper(I) iodide, and copper (II) acetate; a ligand selected from the group: 1,1'-bis(diphenylphosphino)ferrocene, (R or S)-1-(2-diphenylphosphino-1-napthyl)isoquinoline, triphenylphosphine, triphenylarsine, 1,3-bis(2,4,6-trimethylphenyl)imidazolium chloride, tri-t-butylphosphine, tri-2-furylphosphine, (R or S)-2,2'-bis(diphenylphosphino)-1,1'-binapthyl (BINAP), (R or S)-2,2'-bis(di-p-tolylphosphino)-1,1'-binapthyl (Tol-BINAP), and N,N-diethylsalicylamide; and a base selected from potassium carbonate, potassium t-butoxide, tetrabutylammonium hydroxide, triethylamine, diisopropylethylamine, cesium carbonate, cesium acetate, and potassium phosphate;

to form a compound of formula (IV):

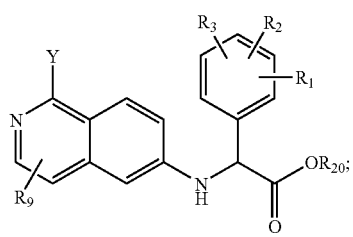

(IVa)

and (c) forming a compound of formula (Ia),

In another preferred embodiment, the present invention provides a process a compound of formula (Ia), which comprises:

contacting a compound of formula (II), wherein $R_{20}$ is methyl; with

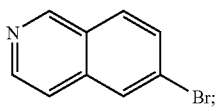

in the presence of diisopropyl ethyl amine;
to form a compound of formula of (IVb):

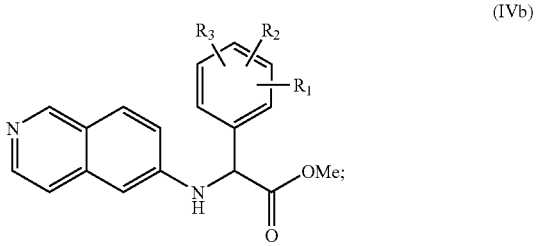

(IVb)

and (c) forming a compound of formula (Ia).

In another preferred embodiment, the present invention provides a process a compound of formula (I), wherein:

(c) forming a compound of formula (I) by contacting a compound of formula (V) with TMS-NR$_6$S(O)$_p$R$_{16}$, wherein $R_6$, $R_{16}$ and p are defined as in Claim 1;

in the presence of a peptide coupling reagent selected from the group: BOP, BOP—Cl, Py-BOP and Py-BROP; and a base selected from the group: triethylamine, diisopropylethylamine, N-methylmorpholine and sodium bicarbonate;

to form a compound of formula (I).

In another preferred embodiment, the present invention provides a process a compound of formula (I), wherein:

(c) forming a compound of formula (Ia) by contacting a compound of formula (Va) with TMS-NR$_6$S(O)$_p$R$_{16}$, wherein $R_6$, $R_{16}$ and p are defined as in Claim 1;

in the presence of a peptide coupling reagent selected from the group: BOP, BOP—Cl, Py-BOP and Py-BROP; and a base selected from the group: triethylamine, diisopropylethylamine, N-methylmorpholine and sodium bicarbonate;

to form a compound of formula (Ia).

In another preferred embodiment, the present invention provides a process a compound of formula (IV):

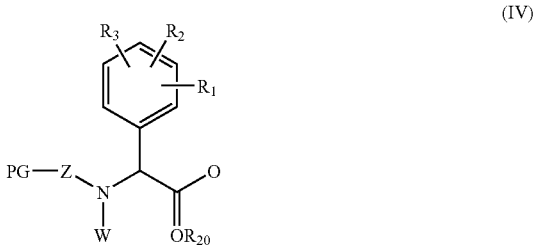

(IV)

wherein $R_1$, $R_2$, $R_3$, W and Z are defined as in Claim 1; $R_{20}$ is $C_{1-4}$alkyl or benzyl; and PG is a protecting group selected from the group: formyl, benzyl, p-methoxybenzyl, nitrobenzyl, 2,4-dimethoxybenzyl, triphenylmethyl, di-p-anisylmethyl, furylmethyl, $C_{1-4}$alkoxycarbonyl, $C_{1-4}$ allyloxycarbonyl, benzyloxycarbonyl, p-methoxybenzyloxycarbonyl, o-nitrobenzyloxycarbonyl, p-nitrobenzyloxycarbonyl, trimethylsilyl, t-Bu-diMe-silyl, $C_{1-4}$alkylidene, and benzylidene.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

A particularly useful compendium of synthetic methods which may be applicable to the preparation of compounds of the present invention may be found in Larock, R. C. *Comprehensive Organic Transformations*, VCH: New York. 1989. Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The compounds of the invention may be prepared by the exemplary processes described in the following Schemes A and C through L. The starting materials for these synthetic routes are either commercially available or may be prepared by methods known to one skilled in the art of organic synthesis from commercially available materials.

SCHEME A

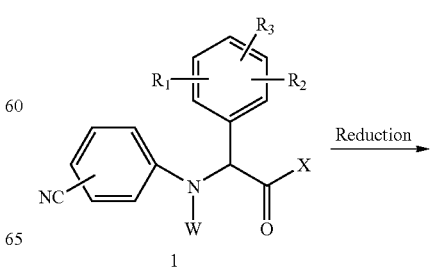

1

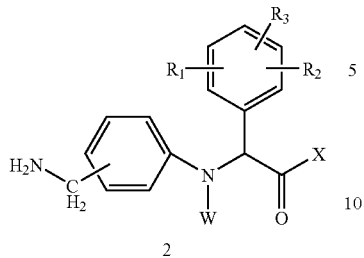

2

Compounds 2 [or compounds of formula (Ia)] can be prepared by reduction of the corresponding nitrile 1 using hydrogen and a catalyst such as Raney Nickel or Pd/C. The preparation of compounds 1 is described in U.S. Pat. No. 6,472,393.

SCHEME C

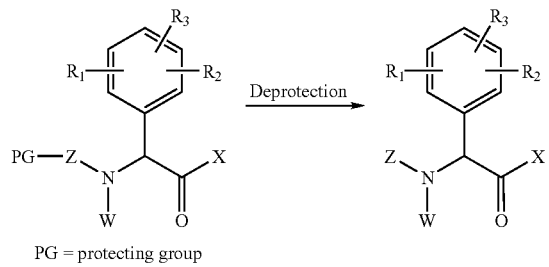

PG = protecting group 5               6

Compounds 6 are typically final products of formula (Ia). Compounds 6 were obtained by deprotection of a basic functionality in compound 5. Typical protecting group for a basic functionality are described in Green and Wuts, "*Protective Groups in Organic Synthesis, Second Edition,*" John Wiley and Sons Eds, New York, (1991). Protecting group for amino or anilino groups include tert-butylcarbamate (Boc) which can be removed with a solution of TFA in DCM. In the case of a primary amino or aniline group, either one or two Boc groups may be employed as protecting groups. Another protecting group for an amino or anilino group is 2,4-dimethoxybenzyl which can be removed by treatment with TFA in anisole or by catalytic hydrogenation. In the case of a primary amine or aniline, the nitrogen can be protected with one or two 2,4-dimethoxybenzyl groups. The first group can be removed with dilute TFA in an organic solvent while the second protecting can be removed with a 10–50% solution of TFA in anisole. Another protecting group for amino or aniline groups is the phthalimide, which can be removed by treatment with hydrazine in methanol. Preparation of compounds of formula 5 is described in Schemes D–K.

SCHEME D

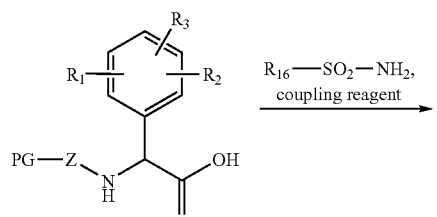

7

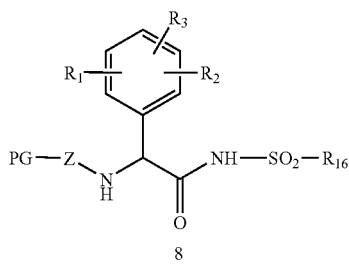

8

Acylsulfonamide 8 can be prepared from the corresponding carboxylic acid 7 by treatment with a primary sulfonamide and a coupling reagent. Coupling reagents include CDI, DIC, and EDC. A base such as DBU or a catalyst such as DMAP can optionally be added. Alternatively, acylsulfonamide 8 can be prepared from carboxylic acid 7 by treatment with a coupling reagent such as BOP and an N-trimethylsilylsulfonamide according to the procedure of Sakaki, J. et al. *Bioorg. Med. Chem. Lett.* 1998, 8, 2241. N-trimethylsilylsulfonamides, in turn, are prepared via silylation of sulfonamides according to the method of Roy, A. K. *J. Am. Chem. Soc.* 1993, 115, 2598. Preparation of carboxylic acid derivatives 7 is described in Schemes H–J.

SCHEME F

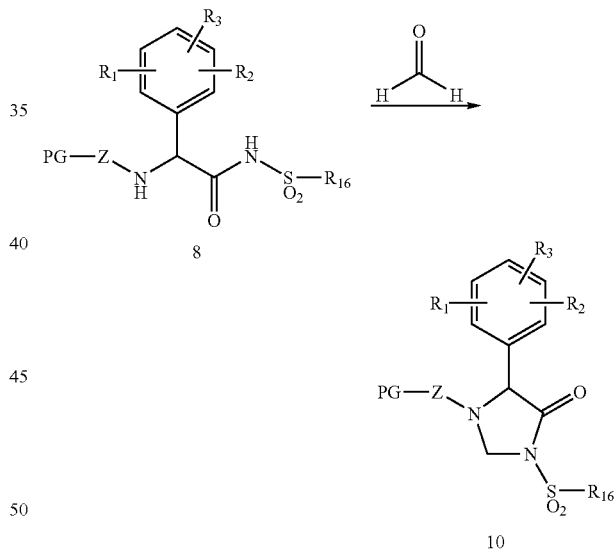

Compounds 10 can be prepared from the corresponding α-amino acylsulfonamide 8 by treatment with formaldehyde in aqueous MeOH containing a small amount (0.1–1%) of TFA.

SCHEME G

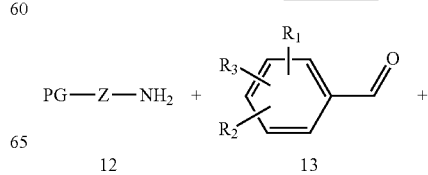

12          13

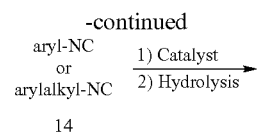

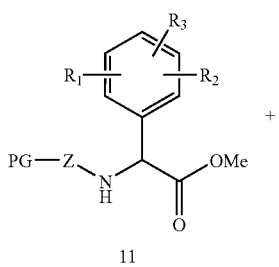

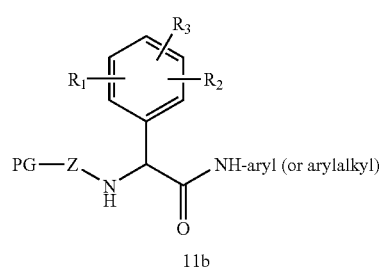

Compounds 11a and 11b can be prepared by a condensation reaction as described in U.S. Pat. No. 6,472,393. Reaction of an amine 12, with an aldehyde 13 and an isonitrile 14 in presence of a Lewis acid and an alkyl alcohol affords condensation product 11 after hydrolysis. Suitable Lewis acid catalysts include boron-trifluoride etherate or aluminium trichloride. Suitable alkyl alcohols include MeOH, EtOH, and i-PrOH. Examples of isonitrile 14 include benzyl isocyanide and tosylmethyl isocyanide. In some cases amides 11b were obtained as a side product in the reaction. These could be separated by column chromatography.

SCHEME H

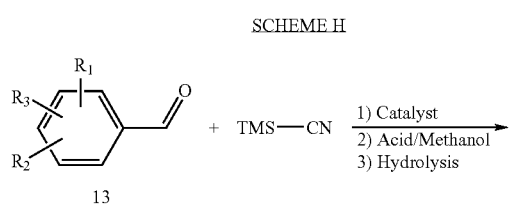

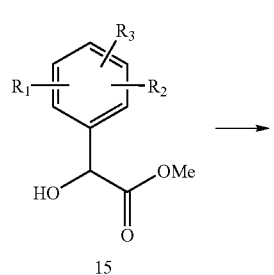

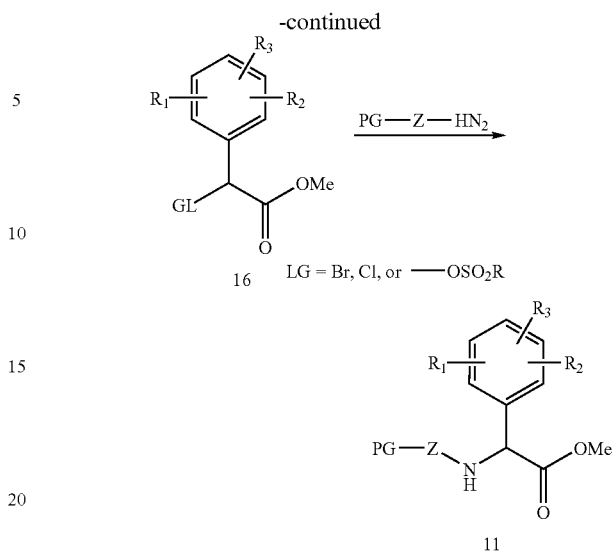

Alternatively to Scheme G, ester 11 can be prepared from hydroxy-ester 15. Compounds 15 can be prepared through a Strecker type synthesis, by condensation of an aldehyde 13 with trimethylsilylcyanide in presence of a Lewis acid catalyst such as boron trifluoride etherate, followed by treatment with hydrochloric acid in MeOH and hydrolysis. Optionally, methyl ester 11 may be converted to the benzyl ester via saponification, followed by alkylation with benzyl bromide. Compounds 15 can be converted to 16 through one of the many halogenation methods known in the art. One suitable method is to treat the alcohol with a solution of bromine, triphenylphosphine and imidazole. Triphenylphosphine can be replaced with polystyrene bound triphenylphosphine which facilitates isolation of 16. Chlorination of compound 16 may be accomplished by treatment with methansulfonyl chloride and triethylamine in DCM. The halide 16 can be converted to 11 by nucleophilic substitution with an amine or aniline in an organic solvent such as DCM or DMF and in presence of a base such as TEA or DIPEA.

SCHEME J

Saponification of methyl esters 11 to the corresponding carboxylic acids 7 can be accomplished using standard conditions well know in the art such as treatment with aqueous lithium hydroxide. Conversion of benzyl esters 11 to the carboxylic acids 7 can be accomplished via catalytic hydrogenation.
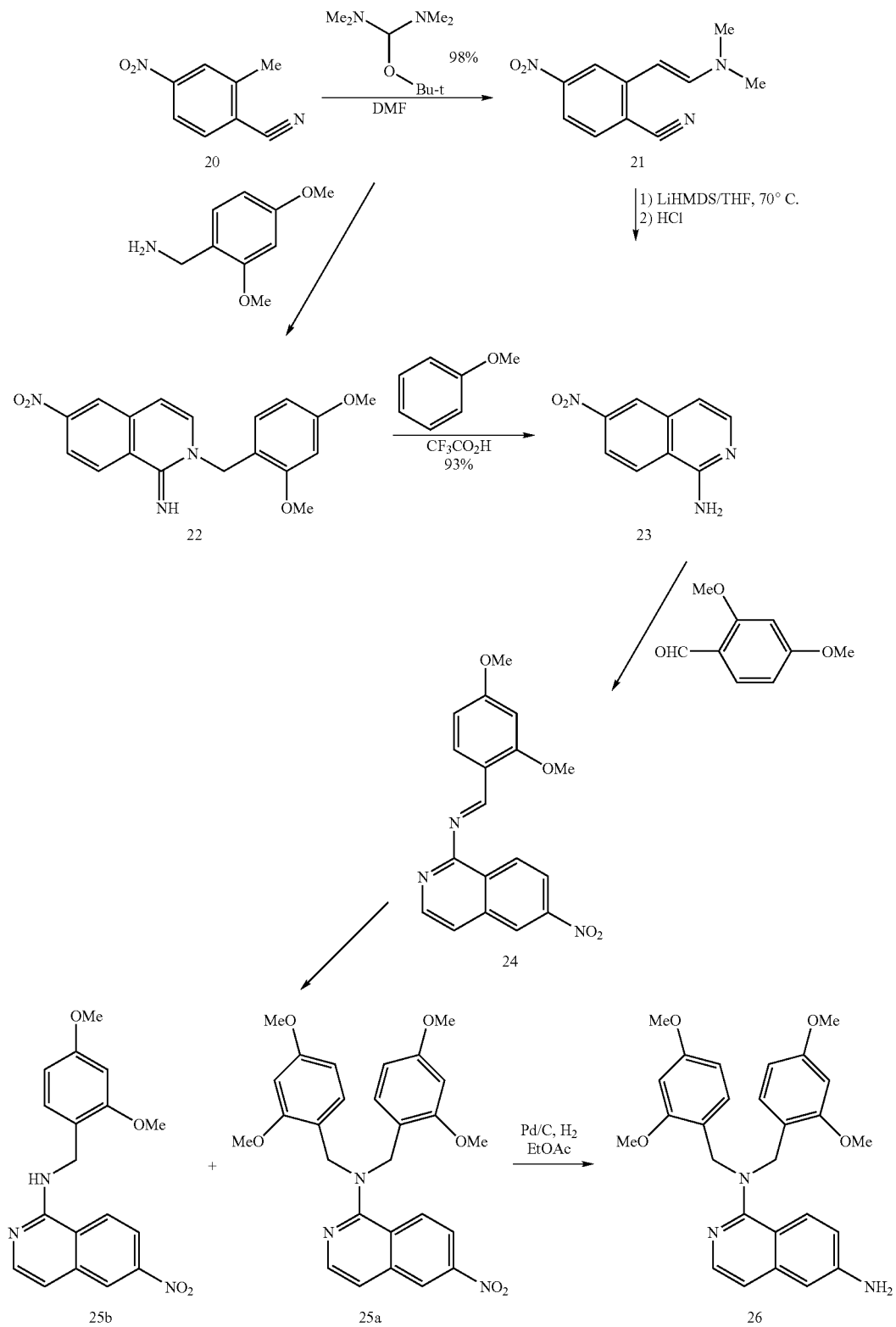

Scheme K described the preparation of reagent 26 which can be used to make compounds of formula (I) by the methods described in Schemes C, D, G, H, I or J. Compound 21 was prepared, according to *J. Med. Chem.*, 1999, 42, 3510–3519, from 2-methyl-4-nitroaniline. A mixture of compound 20 and 1-(1,1-dimethylethoxy)-N,N,N',N'-tetramethyl-methanediamine in dry DMF (10 mL) was stirred at 70° C. for 2 h under $N_2$. After cooling to rt, the reaction mixture was treated with hexane, and the solid was collected by filtration and washed with hexane to give compound 21 as black crystals. Compound 21 was converted to compound 23 in two alternate ways.

In one approach, compound 21 was converted to 23 by adding 1N LiHMDS to a solution of 21 in dry THF under $N_2$. The reaction mixture was stirred at 65° C. for 2 h. After cooling to rt, 12 N HCl was added and the reaction mixture stirred at 50° C. for 1 h. After cooling to rt, the mixture was neutralized with sat'd $NaHCO_3$, the product extracted with EtOAc, and the organic layer washed with water and sat'd NaCl. The product was concentrated and purified to give compound 23 as a yellow solid.

Alternatively, compound 21 was converted to 23 by first mixing compound 21 and 2,4-dimethoxylbenzylamine in DMF and stirring the mixture at 140° C. for 3 h. The solvent was removed by vacuum distillation and residue treated with EtOAc. The orange solid was collected by filtration and washed with hexane to give compound 22. To a solution of compound 22 in anisole was added TFA. The reaction mixture was stirred at 90° C. for 1 h and the solvent removed under reduced pressure. The residue was treated with sat'd $NaHCO_3$ (30 mL) and the product collected by filtration and washed with water to afford compound 23. Compound 23 (366 mg, 1.93 mmol) and 2,4-dimethoxybenzaldehyde were heated for 16 h at 125–130° C. with a stream of nitrogen passing in and out of the reaction flask, and sampling of the reaction mixture at 80° C. indicated conversion to compound 24.

To a solution of 24 and 2,4-dimethoxybenzaldehyde above in THF was added sodium triacetoxyborohydride. The reaction was stirred for 22 h and additional sodium triacetoxyborohydride (1.23 g, 5.8 mmol) was added. After 40 h, the reaction was concentrated to an oil which was taken up in EtOAc, water, and dilute sodium bicarbonate. The EtOAc was washed with water (3×), dried (sodium sulfate), and concentrated to an oily residue, which was purified to give compound 25a as a glassy residue and 140 mg of compound 25b as an amorphous solid. Hydrogenation of compound 25a in EtOAc and MeOH in the presence 10% Pd/C for 1 h at one atmosphere afforded compound 26 as an amorphous solid.

SCHEME L

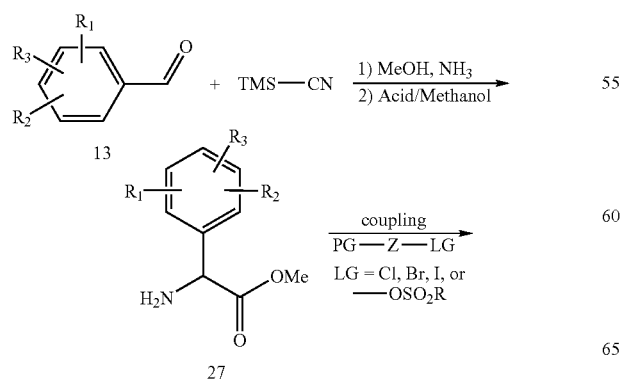

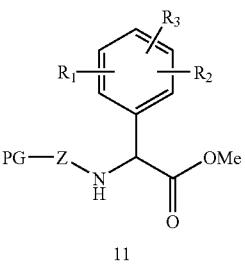

Alternatively to Schemes G and H, as exemplified in Scheme L, esters 11 can be prepared from amino-esters 27. Compounds 27 can be prepared through a Strecker type synthesis, by condensation of an aldehyde 13 with trimethylsilylcyanide in presence of ammonia, followed by treatment with hydrochloric acid in MeOH. Compounds 27 can be converted to 11 via coupling with aryl halides or sulfonates PG-Z-LG by methods known in the art. For example, amino-esters 27 may be coupled to aryl halides PG-Z-Br in the presence of a palladium catalyst, an appropriate ligand, for example, BINAP, and a base such as cesium carbonate to provide esters 11.

SCHEME M

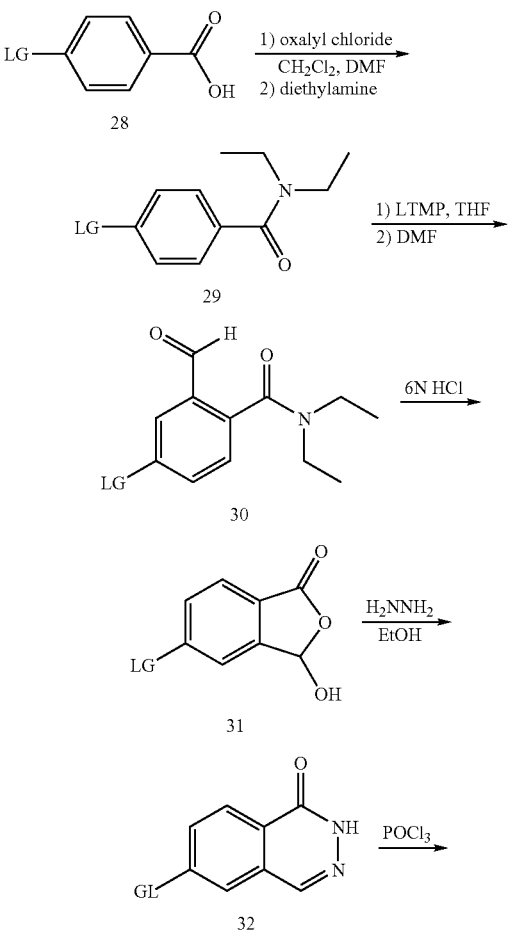

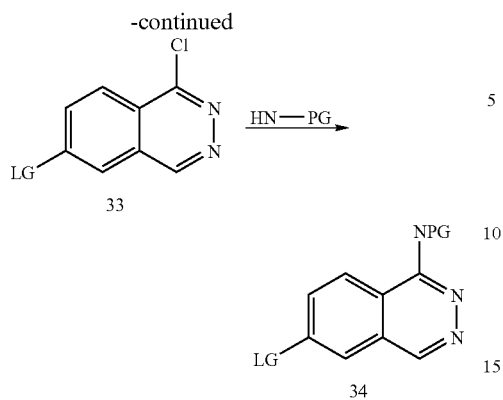

Scheme M exemplifies the synthesis of key intermediates PG-Z-LG (34) where Z=phthalazine, LG is a halogen, and PG is a nitrogen protecting group. Such compounds can be used for the synthesis of compounds of the invention using methods described previously in Schemes C, D, J and L. Commercially available acids 28 are converted to diethylamides 29. Ortho lithiation with lithium 2,2,6,6-tetramethylpiperidide, followed by quenching with DMF affords aldehyde 30. Acidic hydrolysis, followed by cyclization with hydrazine affords phthalazine 32. Chlorination with POCl$_3$, followed by introduction of nitrogen (either protected, unprotected, or with protecting group added as a subsequent step) affords key intermediates 34. Examples of protecting groups (PG) which may be useful include Boc, 2,6-dimethoxybenzyl, and phthalimide.

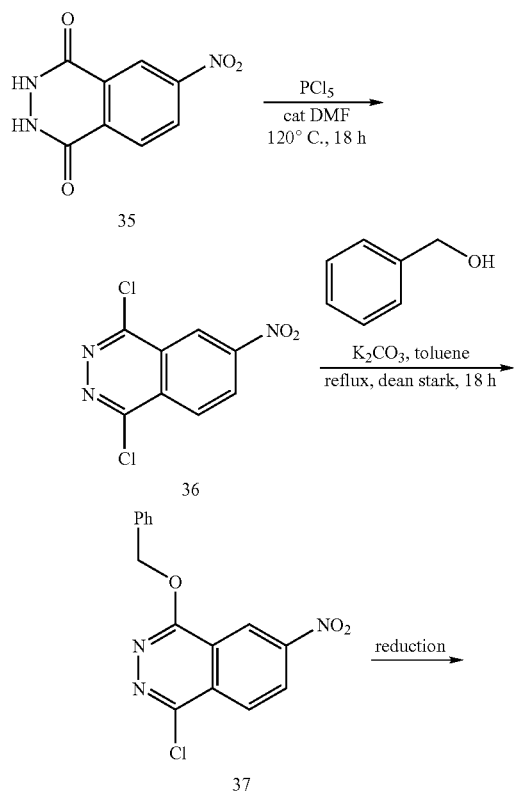

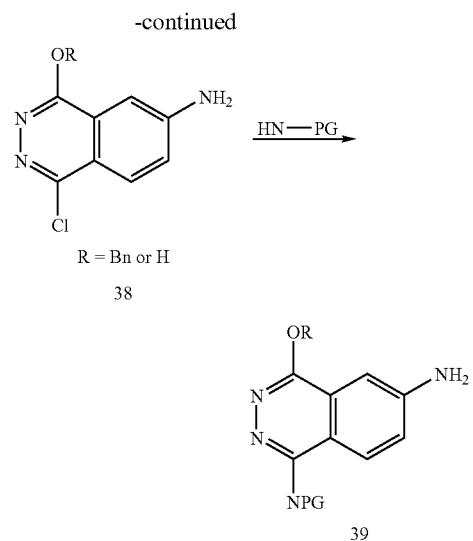

Scheme N exemplifies the synthesis of key intermediates PG-Z-NH$_2$ (39) where Z=hydroxyphthalazine and PG is a nitrogen protecting group. Such compounds can be used for the synthesis of compounds of the invention using methods described previously in Schemes C, D, L, and either G or H. Compound 35 is chlorinated and reacted with benzyl alcohol under basic conditions to give 37. Subsequent selective or nonselective reduction, using for instance, catalytic hydrogenation or Zinin reduction, affords anilinse 38. Introduction of nitrogen (either protected, unprotected, or with protecting group added as a subsequent step) affords key intermediates 39. Examples of protecting groups (PG) which may be useful include Boc, 2,6-dimethoxybenzyl, and phthalimide.

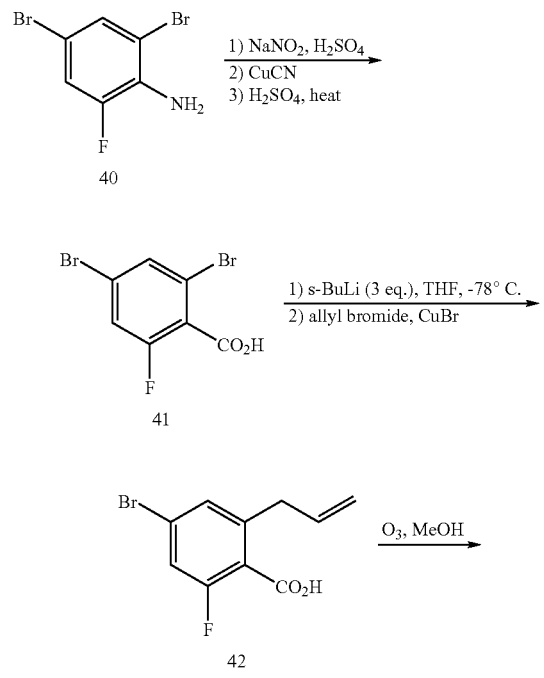

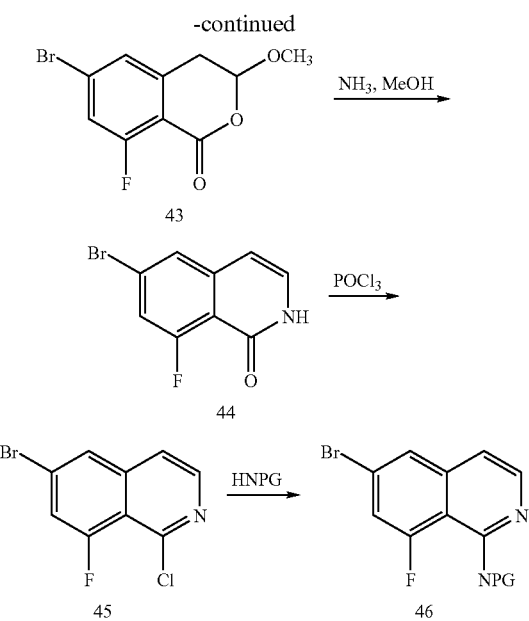

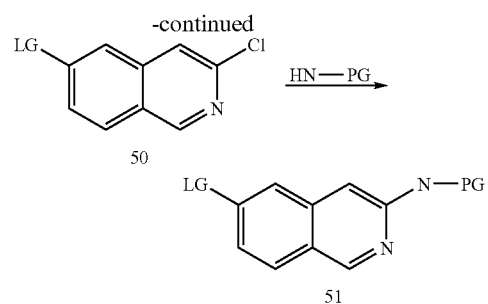

Scheme P exemplifies the synthesis of intermediates PG-Z-LG (51) where LG is a halogen, Z is 3-aminoisoquinoline, and PG is a nitrogen protecting group. Such compounds can be used for the synthesis of compounds of the invention using methods described previously in Schemes C, D, J and L. Nitrosation of indanones 47 affords oximes 48. Chlorination, followed by selective reduction affords 50. Introduction of nitrogen (either protected, unprotected, or with protecting group added as a subsequent step) affords key intermediates 51. Examples of protecting groups (PG) which may be useful include Boc. 2,6-dimethoxybenzyl, and phthalimide.

Scheme O exemplifies the synthesis of fluorinated aminoisoquinoline intermediates 46 where PG is a nitrogen protecting group. Such compounds can be used for the synthesis of compounds of the invention using methods described previously in Schemes C, D, J and L. Diazotization, cyanation, and hydrolysis of aniline 40 affords acid 41. Directed lithium-halogen exchange followed by transmetallation and alkylation with allyl bromide affords 42. Ozonolysis and cyclization with ammonia gives isoquinoline 44. Chlorination with POCl₃, followed by introduction of nitrogen (either protected, unprotected, or with protecting group added as a subsequent step) affords key intermediates 46. Examples of protecting groups (PG) which may be useful include Boc, 2,6-dimethoxybenzyl, and phthalimide.

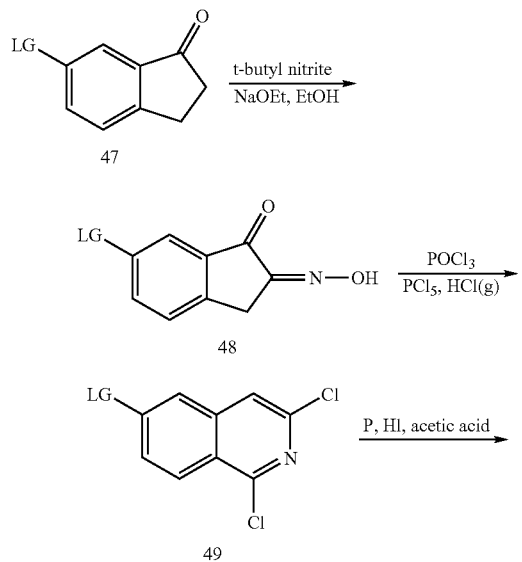

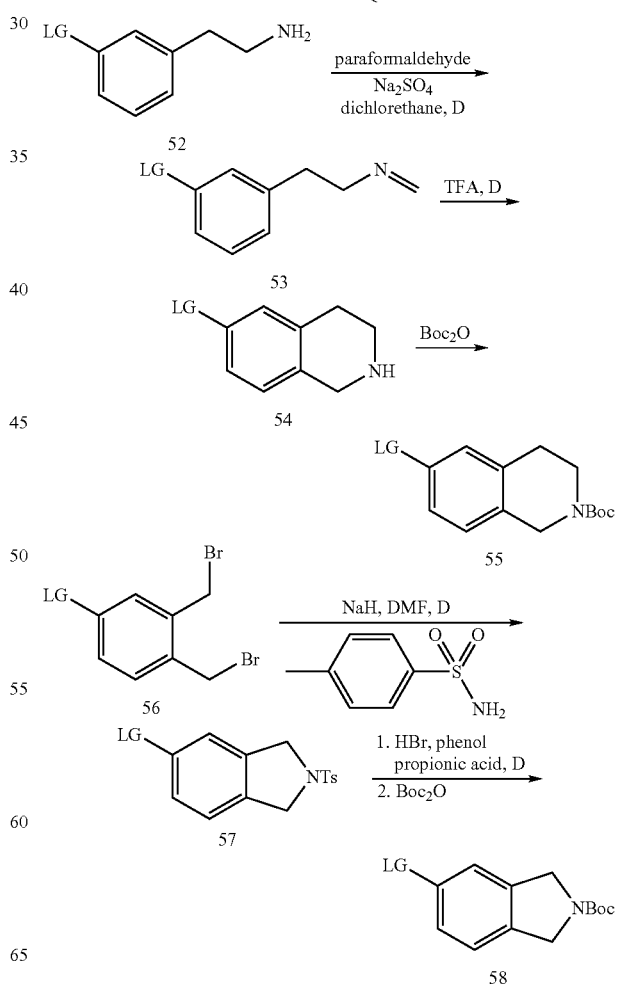

Scheme Q exemplifies the synthesis of intermediates PG-Z-LG (55 and 58) where LG is a halogen, Z is tetrahydroisoquinoline (55) or isoindoline (58). and PG is Boc. Such compounds can be used for the synthesis of compounds of the invention using methods described previously in Schemes C, D, J and L. Phenthylamine 52 can be converted to imine 53, cyclized under acidic conditions, and protected to give 55. Bis-benzyl bromide 56 can be converted to isoindoline 57 by treatment with toluene sulfonamide and strong base. Removal of the sulfonamide and Boc protection affords 58.

Utility

The inventive compounds are inhibitors of the activated coagulation serine protease Factor VIIa and are selective versus Factor IXa, Factor Xa, Factor XIa, and/or thrombin as well as other serine proteases such as trypsin, chymotrypsin, and urokinase. Thus, the compounds are useful for treating or preventing those processes which involve the action of Factor VIIa. As used herein, the term "treating" or "treatment" is intended to encompass responsive measures designed to cure the disease or disorder, to delay the progression of the disease or disorder, and/or to alleviate or lessen its symptoms, as well as prophylaxis measures designed to inhibit or delay the onset of the disease or disorder and/or its symptoms.

In view of their above-referenced serine protease inhibitory activity, the inventive compounds are useful in treating consequences of atherosclerotic plaque rupture including cardiovascular diseases associated with the activation of the coagulation cascade in thrombotic or thrombophilic states. Such diseases include arterial thrombosis, coronary artery disease, acute coronary syndromes, myocardial infarction, unstable angina, chronic stable angina, Prinzmetal's angina, ischemia resulting from vascular occlusion cerebral infarction, stroke and related cerebral vascular diseases (including cerebrovascular accident and transient ischemic attack). Additionally, the compounds are useful in treating or preventing formation of atherosclerotic plaques, transplant atherosclerosis, peripheral arterial disease and intermittent claudication. In addition, the compounds can be used to prevent restenosis following arterial injury induced endogenously (by rupture of an atherosclerotic plaque), or exogenously (by invasive cardiological procedures such as vessel wall injury resulting from angioplasty).

The inventive compounds are also useful in preventing venous thrombosis, coagulation syndromes, deep vein thrombosis (DVT), disseminated intravascular coagulopathy, pulmonary embolism, cerebral thrombosis, atrial fibrillation, and cerebral embolism. The compounds are useful in treating peripheral arterial occlusion, thromboembolic complications of surgery (such as hip replacement, endarterectomy, introduction of artificial heart valves, vascular grafts, and mechanical organs), implantation or transplantation of organ, tissue or cells, and thromboembolic complications of medications (such as oral contraceptives, hormone replacement, and heparin, e.g., for treating heparin-induced thrombocytopenia). The inventive compounds are useful in preventing thrombosis associated with artificial heart valves, stents, and ventricular enlargement including dilated cardiac myopathy and heart failure. The compounds are also useful in treating thrombosis due to confinement (i.e. immobilization, hospitalization, bed rest etc.).

These compounds are also useful in preventing thrombosis and complications in patients genetically predisposed to arterial thrombosis or venous thrombosis (including activated protein C resistance, $FV_{leiden}$, Prothrombin 20210, elevated coagulation factors FVII, FVIII, FIX, FX, FXI, prothrombin, TAFI and fibrinogen), elevated levels of homocystine, and deficient levels of antithrombin, protein C, and protein S. The inventive compounds may be used for treating heparin-intolerant patients, including those with congenital and acquired antithrombin III deficiencies, heparin-induced thrombocytopenia, and those with high levels of polymorphonuclear granulocyte elastase.

The present compounds may further be used to inhibit blood coagulation in connection with the preparation, storage, fractionation, or use of whole blood. For example, the compounds may be used to maintain whole and fractionated blood in the fluid phase such as required for analytical and biological testing, e.g., for ex vivo platelet and other cell function studies, bioanalytical procedures, and quantitation of blood-containing components. The compounds may be used as anticoagulants in extracorpeal blood circuits, such as those necessary in dialysis and surgery (such as coronary artery bypass surgery); for maintaining blood vessel patency in patients undergoing transluminal coronary angioplasty, vascular surgery including bypass grafting, arterial reconstruction, atherectomy, vascular graft and stent patency, tumor cell metastasis, and organ, tissue, or cell implantation and transplantation.

In a particular embodiment, compounds of the present invention are useful for treating any one or more of the aforementioned disorders irrespective of their etiology, e.g., for treating arterial thrombosis, coronary artery disease, acute coronary syndromes, myocardial infarction, unstable angina, ischemia, transplant rejection, rheumatoid arthritis, inflammatory bowel disease, and/or viral infections.

The present invention also provides pharmaceutical compositions comprising at least one compound of formula (I), or a salt thereof, capable of treating a Factor-VIIa associated disorder, in an amount effective therefor, alone or in combination with at least one additional therapeutic agent, and a pharmaceutically acceptable carrier, adjuvant or vehicle. "Additional therapeutic agent" encompasses, but is not limited to, an agent or agents selected from the group consisting of immunosuppressants, potassium channel openers, calcium channel blockers, sodium hydrogen exchanger inhibitors, antiarrhythmic agents, antiatherosclerotic agents, anticoagulants such as antithrombotic agents (Factor Xa inhibitors, anti-platelet agents, or platelet aggregation inhibitors), prothrombolytic agents, fibrinogen antagonists, diuretics, anti-hypertensive agents, ATPase inhibitors, mineralocorticoid receptor antagonists, phospodiesterase inhibitors, antidiabetic agents, anti-inflammatory agents (steroidal and non-steroidal), antioxidants, angiogenesis modulators, antiosteoporosis agents, hormone replacement therapies or hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics (including thyroid receptor antagonists), antiinfective agents, antiviral agents, antibacterial agents, antifungal agents, cholesterol/lipid lowering agents and lipid profile therapies, and agents that mimic ischemic preconditioning and/or myocardial stunning.

In the methods of the present invention, such other therapeutic agent(s) may be administered prior to, simultaneously with or following the administration of the compound(s) of the present invention.

Examples of suitable other anti-inflammatory agents with which the inventive compounds may be used include aspirin, non-steroidal antiinflammatory drugs (NSAIDs) (such as ibuprofen and naproxin), TNF-α inhibitors (such as tenidap and rapamycin or derivatives thereof), or TNF-α antagonists (e.g., infliximab, OR1384), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, therapies for the treatment of irritable bowel syndrome (e.g., Zelmac® and Maxi-K® openers such as those disclosed in U.S. Pat. No. 6,184,231), or other NF-κB inhibitors, such as corticosteroids, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; and nuclear translocation inhibitors, such as deoxyspergualin (DSG).

Examples of suitable other antibiotics with which the inventive compounds may be used include cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins constructed from CD40 and/or CD154/gp39 (e.g., CD40Ig and CD8gp39), β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based antibiotics (e.g., sulfonamides and trimethoprim); polyring systems (e.g., tetracyclins and rifampins); protein synthesis inhibitors (e.g., zyvox, chloropheni-col, clindamycin, etc.); and nitro-class antibiotics (e.g., nitrofurans and nitroimidazoles).

Examples of suitable other antifungal agents with which the inventive compounds may be used include fungal cell wall inhibitors (e.g., candidas), azoles (e.g., fluoconazole and vericonazole), and membrane disruptors (e.g., amphotericin B). Examples of suitable other antiviral agents for use with the inventive compounds include nucleoside-based inhibitors, protease-based inhibitors, viral-assembly inhibitors, and other antiviral agents such as abacavir.

Other suitable therapeutic agents in combination with which the inventive compounds may be used include one or more of the following:

adenosine receptor modulators;

agents used to treat hypertension, heart failure, and/or atheroschlerosis, such as angiotensin-converting enzyme (ACE) inhibitors (e.g., captopril, lisinopril, zofenopril, ramipril, fosinopril, enalapril, ceranopril, cilazopril, delapril, pentopril, and quinapril), vasopeptidase inhibitors, i.e., dual ACE/NEP inhibitors (e.g., omapatrilat and gemopatrilat), AT-1 receptor antagonists (e.g., losartan, irbesartan, and valsartan), ET receptor antagonists (e.g., sitaxsentan, atrsentan, and compounds disclosed in U.S. Pat. No. 5,612,359 and U.S. Pat. No. 6,043,265), Dual ET/AII antagonists (e.g., compounds disclosed in WO 00/01389), neutral endopeptidase (NEP) inhibitors, and Rho-kinase inhibitors;

agents for inhibiting $F_1F_0$-ATPase, including efrapeptin, oligomycin, autovertin B, azide, and compounds described in WO 03/05026;

alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol);

angiogenesis modulators such as endostatin;

anotropic agents such as calcium channel blocking agents (t and l) including verapamil, nifedipine, diltiazem, amlodipine, and mibefradil;

antianginal agents such as nitrates, for example, sodium nitrates, nitroglycerin, isosorbide mononitrate, isosorbide dinitrate, and nitrovisodilators;

antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); K$^+$ channel openers such as I$_{Ach}$ inhibitors and inhibitors of the K$_v$1 subfamily of K$^+$ channel openers such as I$_{Kur}$ inhibitors (e.g., compounds disclosed in U.S. Publication US 20030022890); and gap-junction modulators such as connexions;

anticholinergics such as ipratropium bromide;

anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), P2Y$_1$ and P2Y$_{12}$ antagonists (e.g., clopidogrel, ticlopidine, CS-747, and aspirin/clopidogrel combinations), and Factor Xa inhibitors (e.g., fondaparinux and razaxaban);

antidiabetic agents such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529 assigned to the present assignee, glucagon-like peptide-1 (GLP-1), glucagon phosphorylase, and dipeptidyl peptidase IV (DP4) inhibitors;

antidepressant, antianxiety or antipsychotic agents such as nefazodone, sertraline, diazepam, lorazepam, buspirone, and hydroxyzine palmoate;

antioxidants and/or lipid peroxidation inhibitors such as probucol, BO-653, Vitamin A, Vitamin E, and AGI-1067;

antiosteoporosis agents such as alendronate and raloxifene;

antiobesity agents such as orlistat and aP2 inhibitors (such as those disclosed in U.S. Pat. No. 6,548,529;

antiproliferative agents such as cyclosporin A, paclitaxel, FK 506, and adriamycin;

antiulcer and gastroesophageal reflux disease agents such as famotidine, ranitidine, and omeprazole;

cardiac glycosides such as sodium calcium exchange inhibitors and digitalis;

diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride;

hormone replacement therapies such as estrogen (e.g., congugated estrogens) and estradiol, and hormone receptor modulators such as androgen receptor modulators;

lipid profile modulators including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), squalene synthetase inhibitors, fibrates, bile acid sequestrants (such as questran), niacin and niacin/statin combinations, ACAT1 inhibitors, ACAT2 inhibitors, dual ACAT1/2 inhibitors, microsomal triglyceride transport protein inhibitors (such as disclosed in U.S. Pat. No. 5,739,135, U.S. Pat. No. 5,712,279 and U.S. Pat. No. 5,760,246), cholesterol absorption inhibitors, cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators;

mineralocorticoid receptor antagonists such as spironolactone and eplerenone;

phosphodiesterase (PDE) inhibitors that block the hydrolysis cAMP and/or cGMP including dipyridamole, cilostazol, sildenafil, rolipram, denbutyline, theophylline (1,2-dimethylxanthine), and ARIFLO™ (i.e., cis-4-cyano-4-[3-(cyclopentyloxy)-4-methoxyphenyl]cyclohexane-1-carboxylic acid), or PDE inhibitors in combination with anti-platelet agents;

prostacyclin mimetics such as berapist;

serotonin-2-receptor antagonists (such as ketanserin);

sodium hydrogen exchange-1 (NHE-1) inhibitors such as cariporide and zoniporide;

thrombolytic agents such as tissue plasminogen activator (natural or recombinant), streptokinase, reteplase, activase, lanoteplase, urokinase, prourokinase, tenecteplase (TNK), lanoteplase (nPA), anisolated streptokinase plasminogen activator complex (ASPAC), animal salivary gland plasminogen activators, PAI-1 inhibitors such as XR-330 and T-686, procarboxy peptidase-U, TAFI inhibitors, and inhibitors of α-2-antiplasmin such as anti-α-2-antiplasmin antibody;

urotensin modulators; and vasopressin receptor antagonists.

The above other therapeutic agents, when employed in combination with the compounds of the present invention, may be used in the same dosage form with the compound of formula I, in different dosage forms, in those amounts indicated in the Physicians' Desk Reference (PDR), and/or as otherwise determined by one of ordinary skill in the art.

The compounds of the present invention may act in a synergistic fashion with one or more of the above agents to allow for increased efficacy and/or reduced doses of any of the above agents and therefore minimize potential side-effects such as potential hemorrhagic side effects.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to Factor-VIIa associated disorders.

Factor VIIA Assay

The effectiveness of compounds of the present invention as inhibitors of the coagulation factor VIIa, as well as selectivity versus factors IXa, Xa, XIa, or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of pNA (para-nitroaniline), which was monitored spectrophotometrically by measuring the increase in absorbance at 405 nM, or the release of AMC (amino methylcoumarin, which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2–5 nM, recombinant soluble tissue factor at a concentration of 18–35 nM and the synthetic substrate H-D-Ile-Pro-Arg-pNA (S-2288; Chromogenix or BMPM-2; AnaSpec) at a concentration of 0.001 M. Compounds tested in the assay for Factor VIIa are considered to be active if they exhibit a $K_i$ of equal to or less than 25 µM. Preferred compounds of the present invention have $K_i$'s of equal to or less than 1 µM. More preferred compounds of the present invention have $K_i$'s of equal to or less than 0.1 µM. Even more preferred compounds of the present invention have $K_i$'s of equal to or less than 0.01 µM. Compounds of the present invention have demonstrated $K_i$ values of equal to or less than 25 µM in the assay for Factor VIIa, thereby confirming the utility of the compounds of the present invention as effective inhibitors of coagulation factor VIIa and as anticoagulants for treatment of thromboembolic disorders.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20–100 nM and the synthetic substrate PCIXA2100-B (CenterChem) or Pefafluor IXa 3688 (H-D-Leu-Phe-Gly-Arg-AMC; CenterChem) at a concentration of 0.0004–0.0005 M. Compounds tested in the Factor IXa assay are considered to be active if they exhibit a $K_i$ of equal to or less than 25 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150–1000 pM and the synthetic substrate S-2222 (Bz-Ile-Glu(gamma-OMe, 50%)-Gly-Arg-pNA; Chromogenix) at a concentration of 0.0002–0.0003 M. Compounds tested in the Factor Xa assay are considered to be active if they exhibit a $K_i$ of equal to or less than 25 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75–200 pM (Haematologic Technologies) and the synthetic substrate S-2366 (pyroGlu-Pro-Arg-pNA; Chromogenix) at a concentration of 0.0002–0.00025 M. Compounds tested in the Factor XIa assay are considered to be active if they exhibit a $K_i$ of equal to or less than 25 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200–250 pM and the synthetic substrate S-2366 (pyroGlu-Pro-Arg-pNA; Chromogenix) at a concentration of 0.0002 M. Compounds tested in the thrombin assay are considered to be active if they exhibit a $K_i$ of equal to or less than 25 µM.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20–180 minutes (depending on the protease) and the velocities (rate of absorbance change vs time) were measured. The following relationship was used to calculate $K_i$ values:

$$(v_o-v_s)/v_s=I/(K_i(1+S/K_m))$$

for a competitive inhibitor with one binding site;

$$v_s/v_o=A+((B-A)/1+((IC_{50}/(I)^n))) \text{ and}$$

$$K_i=IC_{50}/(1+S/K_m)$$

for a competitive inhibitor
where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The effectiveness of compounds of the present invention as inhibitors of the coagulation factor VIIa can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 h before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-Venous Shunt Thrombosis Model:

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The following examples illustrate preferred embodiments of the present invention and do not limit the scope of the present invention which is defined in the claims. Abbreviations that are employed in the Examples and Schemes are set forth below for ease of reference as follows:

Abbreviations
Me=methyl
Et=ethyl
MeOH=methanol
EtOH=ethanol
i-PrOH=isopropanol
Ph=phenyl
BINAP=2-2'-bis(diphenylphosphino)1-1'-binaphthyl
Bn=benzyl
t-Bu=tertiary butyl
Boc=tert-butoxycarbonyl
BOP=benzotriazol-1-yloxytris(dimethylamino)phosphonium heafluorophosphate
BOP-Cl: Bis(2-oxo-3-oxazolidinyl)phosphinic chloride
AcOH=acetic acid
i-$Pr_2$NEt=diisopropylethylamine
CBZ=carbobenzyloxy or carbobenzoxy or benzyloxycarbonyl
EtOAc=ethyl acetate
CDI=carbonyl diimidazole
DBU=1,8-Diazabicyclo[5.4.0]undec-7-ene
DMF=dimethyl formamide
DMSO=dimethyl sulfoxide
DME=1,2 dimethoxyethane
DCE=1,2 dichloroethane
DCM=dichloromethane
DMAP=4-dimethylaminopyridine
DCC=dicyclohexylcarbodiimide
DIC or DIPCDI=diisopropylcarbodiimide
DIAD=diisopropyl azodicarboxylate
DIPEA=diisopropylethylamine
DPPF=1,1'-bis(diphenylphosphino)ferrocene
DEPBT=3-(diethoxyphosphoryloxy)-1,2,3-benzotriazin-4 (3H)-one
DMB=2,4-dimethoxy-benzyl
LiOH=lithium hydroxide NMM=N-methyl morpholine
NaHCO$_3$=sodium bicarbonate
NaBH(OAc)$_3$=sodium triacetoxyborohydride
Na$_2$SO$_4$=sodium sulfate
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HCl=hydrochloric acid
HOBT or HOBT.H$_2$O=1-hydroxybenzotriazole hydrate
HOAT=1-Hydroxy-7-azabenzotriazole
HATU=[O-(7-azabenzotriazol-1-yl)-1,1,3,3-tetramethyluronium hexafluorophosphate
HBTU=O-benzotriazol-1-yl-n,n,n',n'-tetramethyluronium hexafluorophosphate
LTMP=lithium 2,2,6,6-tetramethylpiperidide
Py-Brop=bromo-tris-pyrolidino phosphonium hexafluorophosphate
Py-BOP=(benzotriazole-1-yloxy)tripyrrolidinophosphonium hexafluorophaosphate
Pd/C=palladium on carbon
Pd$_2$(dba)$_3$=tris(dibenzylideneacetone)dipalladium (O)
Pd(OAc)$_2$=Palladium acetate
SAX=Strong Anion Exchanger
SCX=Strong Cation Exchanger
PVP=polyvinylpyridine
THF=tetrahydrofuran
TFA=trifluoroacetic acid
TEA=triethylamine
TBS=t-butyldimethylsilyl
Tf=trifluoromethanesulfonyl
h=hour or hours
L=liter
mL=milliliter
µL=microliter
g=gram(s)
mg=milligram(s)
meq=milliequivalent
rt or RT=room temperature
conc.=concentrated
sat or sat'd=saturated
TLC=thin layer chromatography
HPLC=high performance liquid chromatography
RP HPLC=reverse phase HPLC
LC/MS=high performance liquid chromatography/mass spectrometry
MS or Mass Spec=mass spectrometry
MW=molecular weight
mp=melting point

EXAMPLE 1

N-[2-(4-Aminomethyl-phenylamino)-2-(3-ethoxy-4-isopropoxy-phenyl)-acetyl]-benzenesulfonamide trifluoroacetic acid salt

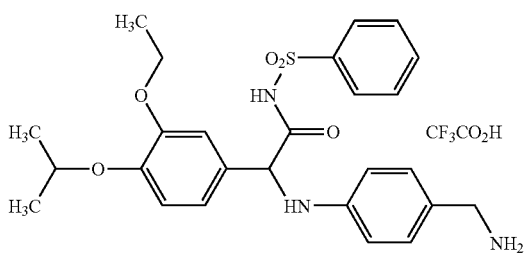

A suspension of N-[2-(4-cyano-phenylamino)-2-(3-ethoxy-4-isopropoxy-phenyl)-acetyl]-benzenesulfonamide (98.7 mg, 0.2 mM) (prepared as described in U.S. Pat. No. 6,472,393), and Raney-Nickel (50 mg) in 5 mL MeOH and 1 mL AcOH was hydrogenated in a Parr-equipment at 35 psi for 4 days. The reaction suspension was filtered (syringe filter), the filtrate concentrated in vacuo, and the oily residue purified by prep-HPLC yielding 70.9 mg (58%) of the TFA salt of Example 1 in the form of a white lyophilate. LR-MS, M-H peak=496.2.

EXAMPLE 2

N-[2-(3-Ethoxy-4-isopropoxy-phenyl)-2-(1,2,3,4-tetrahydro-isoquinolin-7-ylamino)-acetyl]-benzenesulfonamide trifluoroacetic acid salt

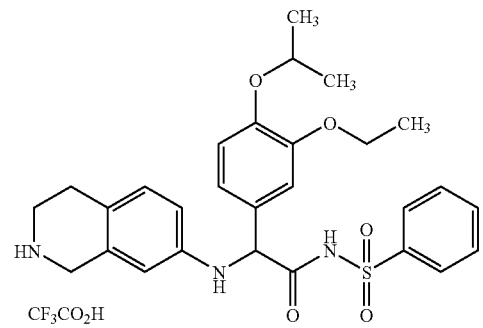

2A 3-ethoxy-4-isopropoxybenzaldehyde

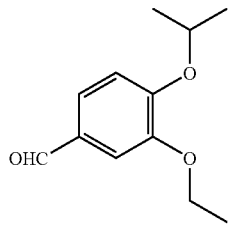

To a solution of 3-ethoxy-4-hydroxy-benzaldehyde (10.0 g, 60.2 mmol) in 100 mL DMF, were added K$_2$CO$_3$ (9.99 g, 72.3 mmol) and 2-iodopropane (12.0 mL, 120.4 mmol). The mixture was stirred at 80° C. for 2 h. then was diluted with EtOAc. The organic phase was washed with water (4×), 10% Na$_2$S$_2$O$_3$ and brine; dried (Na$_2$SO$_4$); filtered through 1" silica gel and concentrated to afford 12.26 g (98%) of 2A as a pale yellow oil.

2B

7-{[(3-ethoxy-4-isopropoxy-phenyl)-methoxycarbonyl-methyl]-amino}-3,4-dihydro-1H-isoquinoline-2-carboxylic acid tert-butyl ester

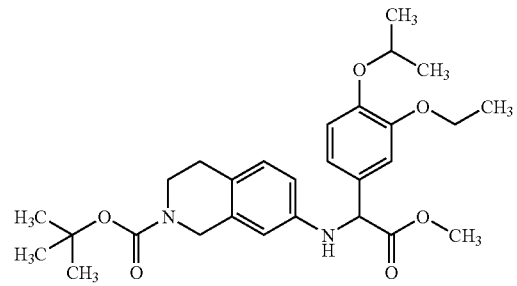

7-Amino-3,4-dihydro-1H-isoquinoline-2-carboxylic acid tert-butyl ester (99.33 mg, 0.40 mmol) and 2A (83.30 mg, 0.40 mmol) were dissolved into anhydrous MeOH (2.0 mL) and heated at 60° C. for 3.5 h. The mixture was cooled to rt and benzyl isonitrile (48.71 µL, 0.40 mmol) was added. The reaction was cooled to 0° C. and boron trifluoride diethyl etherate (152.07 µL, 1.20 mmol) was added in two aliquots. The reaction was allowed to warm to rt with shaking overnight. Water (60 µL) was added and the reaction was shaken at rt for 1 h and concentrated. The residual oil was redissolved into EtOAc and washed with water (3×) and brine, dried over anhydrous Na$_2$SO$_4$, filtered, and concentrated. (The Boc protecting group fell off during the synthesis to give the free secondary amine.) The free amine product was captured on cation exchange resin and eluted off with ammonia in MeOH. The product was purified by preparative HPLC. The purified product (22.7 mg, 0.0570 mmol) was dissolved into anhydrous DCM (1.0 mL). TEA (9.54 µL, 0.0684 mmol) and DMAP (0.70 mg, 0.0057 mmol) were added. The reaction was cooled to 0° C. and di-tert-butyl dicarbonate (14.94 mg, 0.0684 mmol) was added. The reaction was allowed to warm to rt with shaking overnight and concentrated. The residue was dissolved into EtOAc and washed with sat'd NaHCO$_3$, water and brine, dried over anhydrous Na$_2$SO$_4$, filtered, and concentrated to yield 2B which was used in the subsequent step without further purification.

2C

7-{[carboxy-(3-ethoxy-4-isopropoxy-phenyl)-methyl]-amino}-3,4-dihydro-1H-isoquinoline-2-carboxylicacid tert-butyl ester

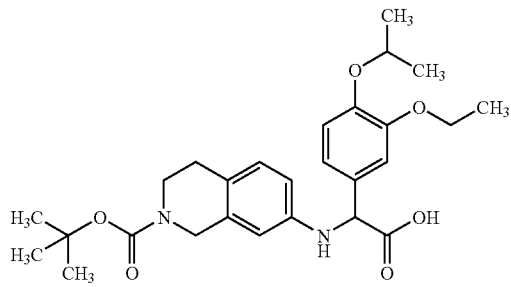

Compound 2B was dissolved into THF (1.5 mL). 2N LiOH (0.50 mL) was added. The reaction was vortexed at rt for 6.5 h. It was then concentrated to remove the THF. The residual oil was redissolved into water. Ice was added. This solution was acidified with 1N HCl and extracted with EtOAc. The combined EtOAc extracts were washed with water and brine, dried over anhydrous sodium sulfate, filtered and concentrated to yield 2C which was used in the subsequent step without further purification.

2D

7-[2-benzenesulfonylamino-1-(3-ethoxy-4-isopropoxy-phenyl)-2-oxo-ethylamino]-3,4-dihydro-1H-isoquinoline-2-carboxylic acid tert-butyl ester

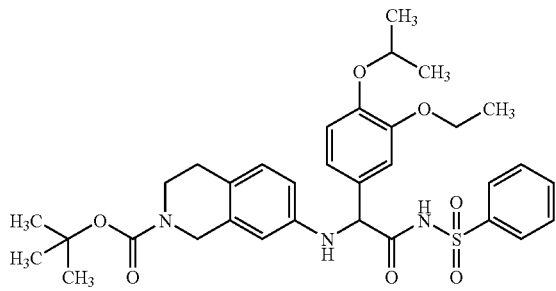

Compound 2C (15.5 mg, 0.0320 mmol) was dissolved in anhydrous THF (1.0 mL). Carbonyldiimidazole (10.9 mg, 0.1236 mmol) was added and the reaction was stirred at rt for 2 h. A solution of benzenesulfonamide (19.4 mg, 0.1236 mmol) and DBU (18.5 µL, 0.1236 mmol) in anhydrous THF (0.50 ml) was prepared and mixed at RT for 10 mins. This solution was then added to the activated ester solution. The reaction was stirred at RT for 48 h. After concentration, the residue was redissolved into EtOAc with the addition of HOAc (pH 4.0). This organic solution was washed with water (3×) and brine, dried over anhydrous sodium sulfate, filtered and concentrated. The residue was purified by preparative HPLC using CH$_3$CN/H$_2$O/TFA as solvent system to afford 2D.

2E

Example 2

Compound 2D was treated with 20% TFA in DCM to yield 3.2 mg of Example 2 as the trifluoracetic acid salt. ((M+H)$^+$=524, HPLC Retention Time=2.54 min, column: Phenominex 4.6 mm×50 mm, 0–100% B 4 min gradient, Solvent A=10% MeOH—90% H$_2$O—10 mM NH$_4$OAc, Solvent B=90% MeOH—10% H$_2$O—10 mM NH$_4$OAc, 4 mL/min, Wavelength=220)

EXAMPLE 3

N-[2-(3-Aminomethyl-phenylamino)-2-(3-ethoxy-4-isopropoxy-phenyl)-acetyl]-benzenesulfonamide trifluoroacetic acid salt

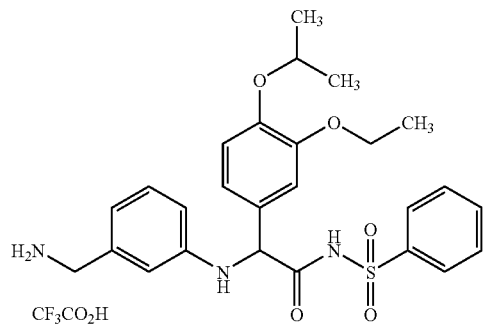

3A

[3-(tert-butoxycarbonylamino-methyl)-phenylamino]-(3-ethoxy-4-isopropoxy-phenyl)-acetic acid methyl ester

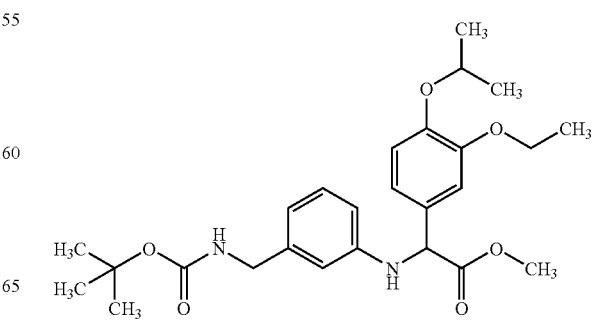

Compound 3A was prepared following the same or similar procedure as described above for 2B, except (3-aminobenzyl)-carbamic acid tert-butyl ester (88.91 mg, 0.40 mmol) was used instead of 7-amino-3,4-dihydro-1H-isoquinoline-2-carboxylic acid tert-butyl ester.

3B

[3-(tert-butoxycarbonylamino-methyl)-phenylamino]-(3-ethoxy-4-isopropoxy-phenyl)-acetic acid

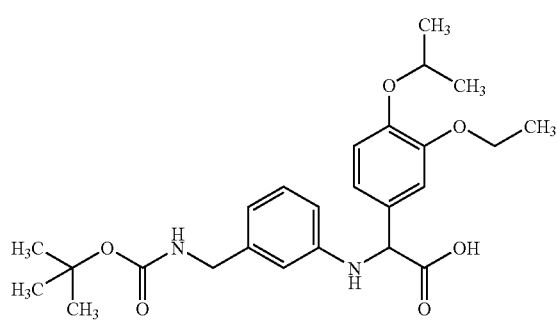

Compound 3B was prepared from compound 3A following the same or similar procedure described above in 2C.

3C

{3-[2-benzenesulfonylamino-1-(3-ethoxy-4-isopropoxy-phenyl)-2-oxo-ethylamino]-benzyl}-carbamic acid tere-butyl ester

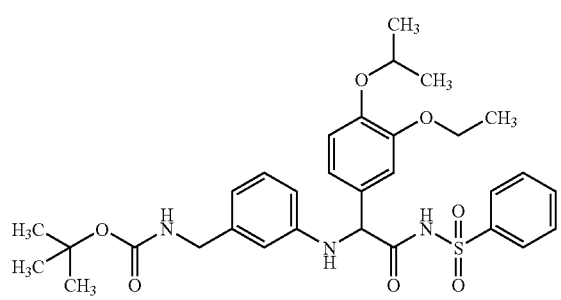

Compound 3C was prepared from compound 3B following the same or similar procedure as described in 2D.

3D

Example 3

Compound 3C was treated with 20% TFA in DCM to yield 1.1 mg of Example 3 as the trifluoroacetic acid salt. ((M+H)$^+$=498, HPLC Retention Time=2.61 min, column: Phenominex 4.6 mm×50 mm, 0–100% B 4 min gradient, Solvent A=10% MeOH—90% H$_2$—10 mM NH$_4$OAc, Solvent B=90% MeOH—10% H$_2$O—10 mM NH$_4$OAc, 4 mL/min, Wavelength=220).

EXAMPLE 4

4-[3-Benzenesulfonyl-5-(3-ethoxy-4-isopropoxy-phenyl)-4-oxo-imidazolidin-1-yl]-benzamidine trifluoroacetic acid salt

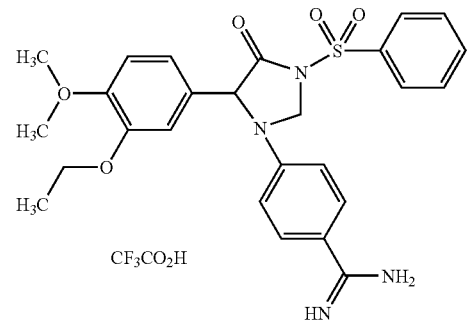

62.4 mg (0.1 mM) of 4-[2-Benzenesulfonylamino-1-(3-ethoxy-4-isopropoxy-phenyl)-2-oxo-ethylamino]-benzamidne (prepared as described in U.S. Pat. No. 6,472,393) was dissolved in 10 mL 95:5:0.1 methanol/H$_2$O/TFA and one drop formaldehyde solution was added. Stirring for 20 min and concentration at 40° C. yielded white fine needles of Example 4 (62 mg, 97.5%) as the trifluoracetic acid salt.

EXAMPLE 5

N-[2-(1-Amino-isoquinolin-6-ylamino)-2-(3-ethoxy-4-isopropoxy-phenyl)-acetyl]-benzenesulfonamide trifluoracetic acid salt

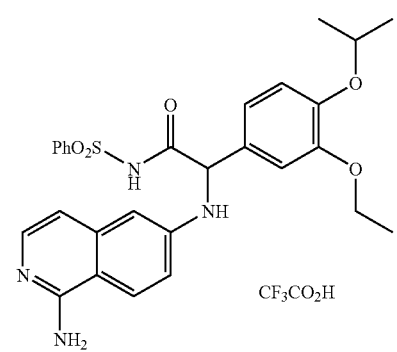

5A 2-(6-Nitro-isoquinolin-1-yl)-isoindole-1,3-dione

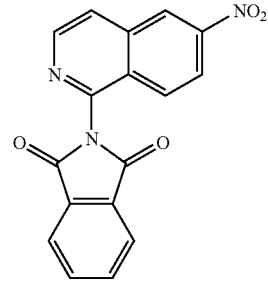

To a suspension of 6-nitro-isoquinolin-1-ylamine (23, Scheme K) (1.00 g, 5.29 mmol) in TEA (7.5 mL, 53 mmol)

and THF 7.5 mL at 0° C., was added phthaloyl dichloride (0.80 mL, 5.55 mmol). The mixture was stirred at rt for 5 h, then poured into 100 mL rapidly stirred water. The precipitate was collected by filtration, rinsed with water, and dried in vacuo at 40° C. to afford 1.32 g of 5A as a yellow solid. ¹H NMR (400 MHz, CDCl₃) δ 8.87 (d, J=2.2, 1H), 8.77 (d, J=5.7, 1H), 8.34 (dd, J=9.2, 2.2, 1H), 8.04–8.00 (m, 4H), 7.89–7.87 (m, 2H).

5B 2-(6-Amino-isoquinolin-1-yl)-isoindole-1,3-dione

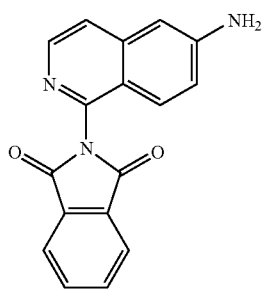

A mixture of 5A (630 mg, 1.97 mmol) and PtO₂ (300 mg) in 50 mL EtOAc was hydrogenated under H₂ (1 atm) for 24 h, then was filtered and concentrated to afford 500 mg of 5B, which was used without further purification.
LC/MS: 290.24 (M+H)⁺.

5C

Methyl 2-(3-ethoxy-4-isopropoxyphenyl)-2-hydroxyacetate

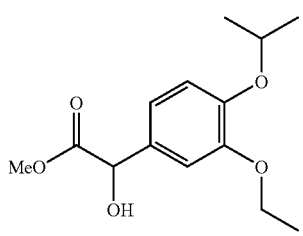

To a solution of 2A (6.00 g, 28.8 mmol) in 100 mL CH₂Cl₂ at rt, were added TMSCN (19.2 mL, 144.1 mmol) and boron trifluoride diethyl etherate (1.44 mL, 11.4 mmol). The mixture was stirred at rt for 3 days, then was concentrated to a brown oil. The residue was dissolved in 100 mL Et₂O and cooled to 0° C. Methanol (5 mL) was added, followed by 85 mL 1M HCl in Et₂O. The mixture was stirred for 30 min then was allowed to stand at 40° C. for 48 h. The resultant precipitate was collected by filtration, then was dissolved in 1:1 CH₂Cl₂/H₂O. The biphasic mixture was stirred at rt for 1 h, then the phases were separated. The aqueous phase was extracted with CH₂Cl₂ (2×). The combined organic extract was washed with brine, dried (Na₂SO₄) and concentrated. The crude residue was purified by flash chromatography (30 to 35% EtOAc/hexanes, stepwise gradient) to afford 3.89 g of 5C as a colorless solid.

5D (3-Ethoxy-4-isopropoxy-phenyl)-hydroxy-acetic acid

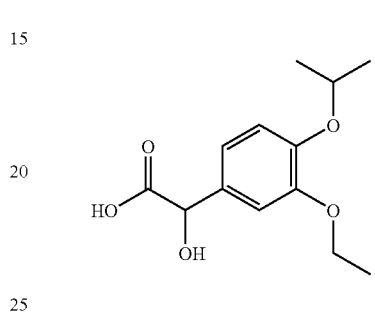

To a solution of 5C (2.54 g, 9.47 mmol) in 30 mL THF at rt, was added a 1 M aqueous solution of LiOH (10.4 mL, 10.4 mmol). The solution was stirred at rt for 1 h, then the volatile solvent was removed in vacuo. The aqueous mixture was acidified with 1N HCl, then extracted with EtOAc (4×). The combined organic extract was washed with brine, dried (Na₂SO₄), and concentrated to afford 2.41 g of 5D as an off-white solid. ¹H NMR (400 MHz, CDCl₃) δ 6.87–6.79 (m, 3H), 5.07 (s, 1H), 4.42–4.36 (m, 1H), 3.98 (q, J=7.0, 2H), 1.32 (t, J=7.0, 3H), 1.25 (d, J=6.1, 6H).

5E (3-Ethoxy-4-isopropoxy-phenyl)-hydroxy-acetic acid benzyl ester

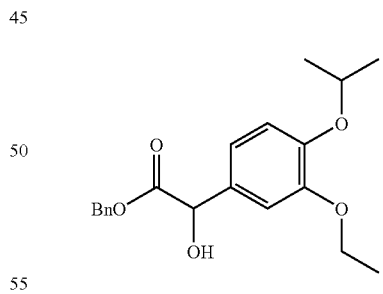

To a solution of 5D (2.41 g, 9.47 mmol) in 25 mL DMF at rt, were added Cs₂CO₃ (6.17 g, 18.9 mmol) and benzyl bromide (1.18 mL, 9.94 mmol). The mixture was stirred at rt for 2 h, then diluted with EtOAc. The organic phase was washed with H₂O (3×) and brine, dried (Na₂SO₄), and concentrated. The crude residue was purified by flash chromatography (step gradient, 25 to 30% EtOAc/hexanes) to afford 2.99 g of 5E as a colorless solid. LC/MS: 367.2 (M+Na)⁺.

5F

Chloro-(3-ethoxy-4-isopropoxy-phenyl)-acetic acid benzyl ester

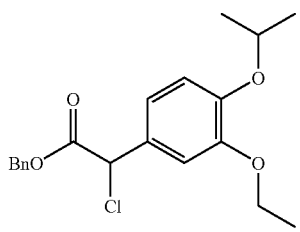

To a solution of 5E (2.99 g, 8.68 mmol) and TEA (1.82 mL, 13.0 mmol) at 0° C., was added methanesulfonyl chloride (0.742 mL, 9.55 mmol). The mixture was stirred at rt for 2 h, then diluted with EtOAc. The organic phase was washed with 0.5 N HCl, water, and brine, dried ($Na_2SO_4$), filtered through a 1" pad of silica gel, and concentrated to afford 2.90 g of 5F as a pale yellow solid, which was used in the following step without further purification.

5G

[1-(1,3-Dioxo-1,3-dihydro-isoindol-2-yl)-isoquinolin-6-ylamino]-(3-ethoxy-4-isopropoxy-phenyl)-acetic acid benzyl ester

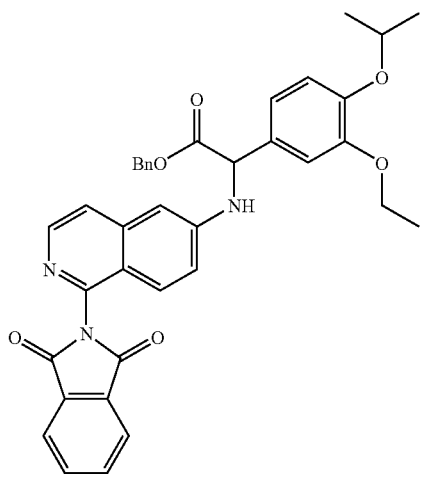

To a solution of 5F (1.23 g, 3.39 mmol) in 5 mL DMF, were added 5B (842 mg, 2.82 mmol) and diisopropylethylamine (0.737 mL, 4.23 mmol). The mixture was stirred at 90° C. for 17 h, then was diluted with EtOAc. The organic phase was washed with water and brine, dried ($Na_2SO_4$), and concentrated. The crude product was purified by flash chromatography (10% EtOAc/$CHCl_3$). The resultant oil was triturated with 30 mL EtOAc and insoluble materials were removed by filtration. The filtrate was concentrated to afford 950 mg of 5G. LC/MS: 616.36 $(M+H)^+$.

5H

[1-(1,3-Dioxo-1,3-dihydro-isoindol-2-yl)-isoquinolin-6-ylamino]-(3-ethoxy-4-isopropoxy-phenyl)-acetic acid

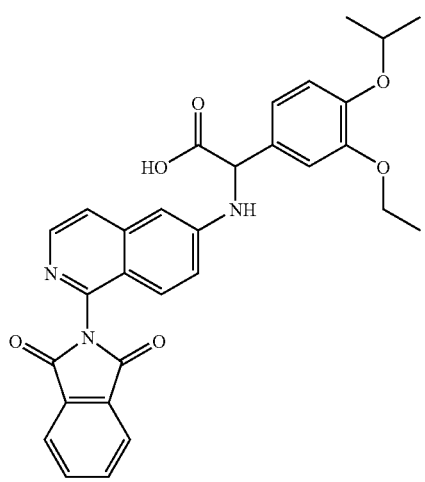

A mixture of 5G (950 mg) and 10% Pd—C (1.0 g) in 20 mL THF was hydrogenated at 60 psi $H_2$ for 20 h, then filtered and concentrated to afford 760 mg of 5H which was used without further purification in the following step. LC/MS: 526.23 $(M+H)^+$.

5I

N-[2-[1-(1,3-Dioxo-1,3-dihydro-isoindol-2-yl)-isoquinolin-6-ylamino]-2-(3-ethoxy-4-isopropoxy-phenyl)-acetyl]-benzenesulfonamide

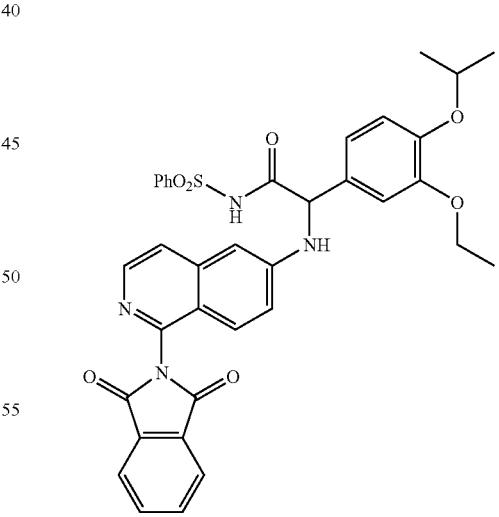

To a solution of 5H (350 mg, 0.666 mmol) in 15 mL $CH_2Cl_2$/DMF (10:1), was added TEA (0.460 mL, 3.30 mmol), BOP (353 mg, 0.799 mmol), and $PhSO_2NHTMS$ (305 mg, 1.33 mmol) (prepared according to the following reference: Roy, A. K. *J. Am. Chem. Soc.* 1993, 115, 2598). The mixture was stirred at rt for 1 h, then was diluted with EtOAc, washed with $H_2O$ and brine, dried ($Na_2SO_4$), and concentrated. The crude material was purified by silica gel chromatography (40% acetone/CH$_2$Cl$_2$) to afford 300 mg of racemic 5I. LC/MS: 665.30 (M+H)$^+$.

5J

Chiral Separation of 5I 400 mg of racemic 5I (300 mg from above along with an additional 100 mg from another batch) was chromatographed on a 2.0 cm×50.0 cm Chiralpak OD column eluting with 50% IPA/heptane with 0.1% TFA at 55 mL/min to afford enantiomer 1 (170 mg) followed by enantiomer 2 (170 mg).

5K

Preparation of Enantiomers 1 and 2 of Example 5

To a mixture of enantiomer 1 of 5I (40 mg) in 2 mL EtOH, was added 2 drops hydrazine hydrate. The mixture was stirred at 50° C. for 2 h and concentrated. The resultant crude residue was dissolved in DMSO and purified by preparative chromatography (gradient, 10 to 98% CH$_3$CN/H$_2$O+0.1% TFA) to afford 21 mg of enantiomer 1 of Example 5 as the trifluoracetic acid salt. LC/MS: 535.35 (M+H)$^+$; Chiral HPLC (Chiralpak AD, 60/40/0.1 hexanes:IPA:TFA) 99% e.e.

Enantiomer 2 of 5I (40 mg) was deprotected and purified in the same fashion to afford 23 mg of enantiomer 2 of Example 5 as the trifluoracetic acid salt. LC/MS: 535.35 (M+H)$^+$; Chiral HPLC (Chiralpak AD, 60/40/0.1 hexanes:IPA:TFA) 92% e.e.

The following examples were prepared in racemic form as their trifluoroacetic acid salts via the general synthetic route described in Example 5.

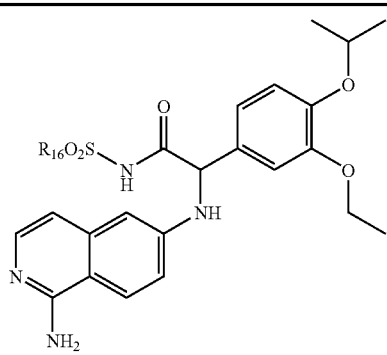

| Example | R$_{16}$ | MS (M + H$^+$) |
|---|---|---|
| 6 | 4-OH-phenyl | 551.42 |
| 7 | 4-CO$_2$H-phenyl | 580.42 |
| 8 | 4-NO$_2$-phenyl | 580.42 |
| 9 | benzyl | 549.45 |
| 10 | 2-naphthyl | 585.47 |
| 11 | 4-OMe-phenyl | 565.46 |
| 12 | 4-NH$_2$-phenyl | 550.46 |
| 13 | 3-CO$_2$H-phenyl | 580.42 |
| 14 | 4-Me-phenyl | 549.48 |
| 15 | 4-F-phenyl | 553.42 |
| 16 | Me | 473.47 |
| 17 | Et | 487.44 |
| 18 | i-Pr | 501.42 |

-continued

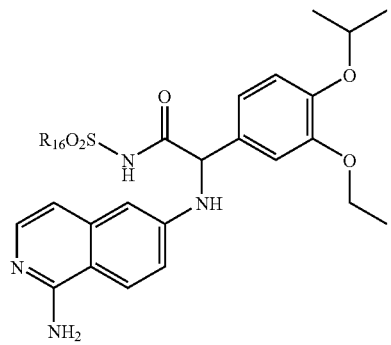

| Example | R$_{16}$ | MS (M + H$^+$) |
|---|---|---|
| 19 | t-Bu | 515.42 |
| 20 | 5-Cl-1,3-diMe-1H-pyrazol-4-yl | 587.43 |
| 21 | 3-F-phenyl | 553.39 |
| 22 | 3-NO$_2$-phenyl | 580.42 |
| 23 | benzo[1,2,5]thiadiazol-4-yl | 593.42 |
| 24 | Quinolin-8-yl | 586.42 |
| 25 | 3-NH$_2$-phenyl | 550.42 |
| 26 | 2,4-diMe-thiazol-5-yl | 570.36 |
| 27 | 5-Me-1-phenyl-1H-pyrazol-4-yl | 615.45 |
| 28 | 2,3-dihydro-benzo[1,4]dioxin-5-yl | 593.41 |
| 29 | 2-NO$_2$-phenyl | 580.38 |
| 30 | 4-(2-tert-butyl cabamoyl-ethyl)-phenyl | 578.55 |
| 31 | 3-CH$_2$OH-phenyl | 565.40 |
| 32 | 4-CH$_2$OH-phenyl | 565.41 |
| 33 | 3-CO$_2$H-4-OH-phenyl | 595.42 |
| 34 | 3-OH-phenyl | 551.40 |
| 35 | 2-OH-phenyl | 551.41 |
| 36 | 3-CN-phenyl | 560.42 |
| 37 | 3-Me-phenyl | 549.41 |
| 38 | 2-NH$_2$-phenyl | 550.37 |
| 39 | 4-(2-CH$_2$CH$_2$NH$_2$)-phenyl | 578.45 |
| 40 | 4-CH$_2$NH$_2$-phenyl | 664.58 |
| 41 | 3-CH$_2$NH$_2$-phenyl | 664.58 |

EXAMPLE 42

2-Amino-1H-benzoimidazole-5-sulfonic acid [2-(1-amino-isoquinolin-6-ylamino)-2-(3-ethoxy-4-isopropoxy-phenyl)-acetyl]-amide bis-trifluoroacetic acid salt

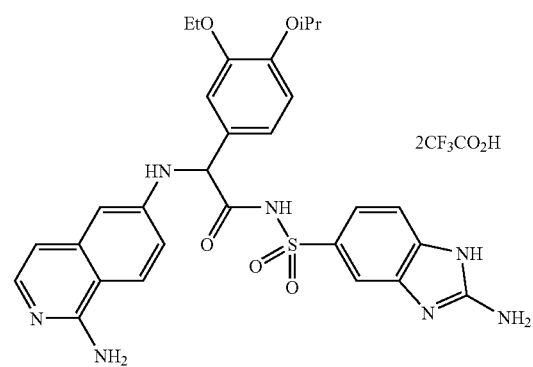

42A

1H-Benzoimidazol-2-ylamine

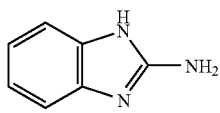

A mixture of carbendazin (2.00 g, 10.5 mmol) and KOH (1.32 g, 13.5 mmol) in 40 mL MeOH and 12 mL H$_2$O was refluxed for 36 h. The mixture was cooled and the MeOH was evaporated. The mixture was extracted with EtOAc (3×) and THF (2×). The combined organic was washed with brine, dried (Na$_2$SO$_4$) and concentrated to afford 1.30 g of intermediate 42A.

42B

2-Amino-3H-benzoimidazole-5-sulfonyl chloride hydrochloride salt

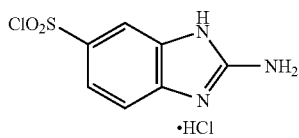

To chlorosulfonic acid (1 mL) at 0° C., was added intermediate 42A (100 mg). The mixture was stirred at rt for 1.5 h, then poured onto ice. The precipitate was was collected by filtration, rinsed with water, and sucked dry to afford 163 mg of 42B as a white powder. LC-MS: 232.18 (M+H)$^+$.

42C

2-Amino-3H-benzoimidazole-5-sulfonyl azide

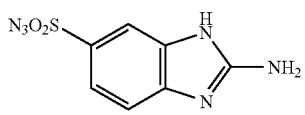

To a solution of 42B (150 mg, 0.559 mmol) in 4 mL THF/H$_2$O (3:1) at rt, was added NaN$_3$ (109 mg, 1.68 mmol). The mixture was stirred for 1 h, then diluted with water and extracted with EtOAc (3×). The combined organic extract was washed with brine, dried (Na$_2$SO$_4$) and concentrated to afford 145 mg of 42C as a yellow oil. LC-MS: 239.19 (M+H)$^+$.

42D

2-Amino-1H-benzoimidazole-5-sulfonic acid [2-[1-(1,3-dioxo-1,3-dihydro-isoindol-2-yl)-isoquinolin-6-ylamino]-2-(3-ethoxy-4-isopropoxy-phenyl)-acetyl]-amide

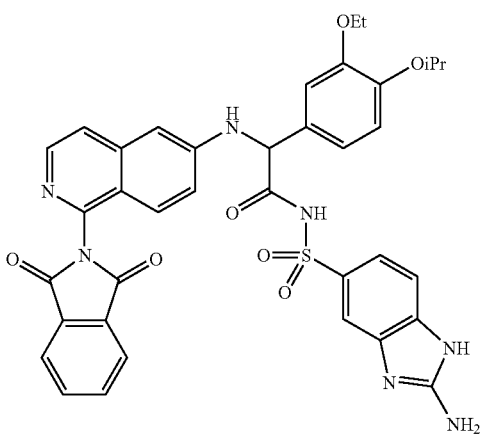

To a solution of 5H (50 mg, 0.095 mmol) in 1 mL THF at −10° C., were added N-methylmorpholine (12.5 µL, 0.095 mmol) and iso-butyl chloroformate (12.4 µL, 0.114 mmol). The mixed anhydride was stirred at −10° C. for 30 min. Simultaneously, a solution of trimethylsilane thiolate was prepared as follows: To a solution of 1,1,1,3,3,3-hexamethyl-disilathiane (40 µL, 0.19 mmol) in 0.5 mL THF at −10° C., was added a solution of tetrabutylammonium fluoride (1M in THF, 190 µL, 0.19 mmol). The green solution was stirred for 5 min. 350 mL of this solution (0.095 mmol) was added to the mixed anhydride. The reaction was stirred at −10° C. for 30 min, then at rt for 30 min. The solvent was evaporated under a stream of Ar and coevaporated with MeOH (2×) to afford the thioacid. The thioacid was dissolved in 1 mL MeOH. To this mixture was added 2,6-lutidine (33 µL, 0.285 mmol) followed by a solution of sulfonylazide 42C in 1 mL MeOH. The mixture was stirred at rt for 3 days, then evaporated to afford the intermediate 42D, which was used in the following step without further purification.

42E

Example 42

To a mixture of 42D in 3 mL MeOH, was added 3 drops of hydrazine hydrate. The mixture was stirred at 50° C. for 30 min, then concentrated. The product was purified by preparative LC-MS to afford 25.5 mg of Example 42 as the bis-trifluoroacetic acid salt. LC-MS: 590.51 (M+H)$^+$.

EXAMPLE 43

N-[2-(3-Amino-benzo[d]isoxazol-6-ylamino)-2-(3-ethoxy-4-isopropoxy-phenyl)-acetyl]-benzenesulfonamide trifluoroacetic acid salt

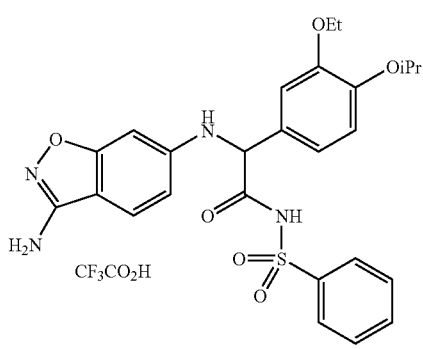

43A

Chloro-(3-ethoxy-4-isopropoxy-phenyl)-acetic acid methyl ester

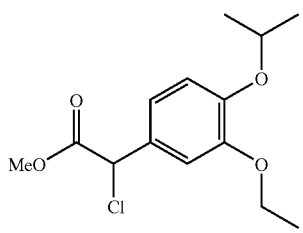

A solution of 5C (500 mg, 1.86 mmol) in 10 mL CH$_2$Cl$_2$ at 0° C., were added TEA (390 μL, 2.80 mmol) and methanesulfonyl chloride (159 μL, 2.05 mmol). The mixture was stirred at 0° C. for 2 h, then diluted with EtOAc. The organic phase was washed 0.2 N HCl, water and brine; dried (Na$_2$SO$_4$), filtered through a 1" pad of SiO$_2$ and concentrated to afford 43A as an orange oil that was used without further purification.

43B (4-Cyano-3-fluoro-phenylamino)-(3-ethoxy-4-isopropoxy-phenyl)-acetic acid methyl ester

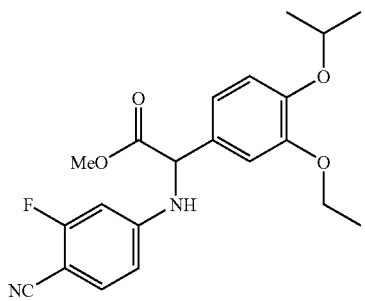

To a solution of compound 43A (190 mg, 0.663 mmol) in 2.5 mL DMF, were added 4-Amino-2-fluorobenzonitrile (prepared according to the method of Mackman, R. L. *J. Med. Chem.* 2001, 44, 3856–3871) (86 mg, 0.632 mmol) and DIEA (165 μL, 0.948 mmol). The mixture was stirred at 90° C. for 24 h, then diluted with EtOAc. The organic phase was washed with water, sat. NaHCO$_3$, and brine; dried (Na$_2$SO$_4$) and concentrated. The crude material was purified by flash chromatography (30% EtOAc/hexanes) to afford 91 mg of 43B. $^1$H NMR (400 MHz, CDCl$_3$) δ 7.28 (t, 1H), 6.94–6.84 (m, 3H), 6.34 (dd, 1H), 6.22 (dd, 1H), 5.63 (d, J=4.8, 1H), 4.93 (d, J=5.7, 1H), 4.49–4.44 (m, 1H), 4.07–4.00 (m, 2H), 3.76 (s, 3H), 1.40 (t, J=6.6, 3H), 1.33 (d, J=6.2, 6H).

43C (4-Cyano-3-fluoro-phenylamino)-(3-ethoxy-4-isopropoxy-phenyl)-acetic acid

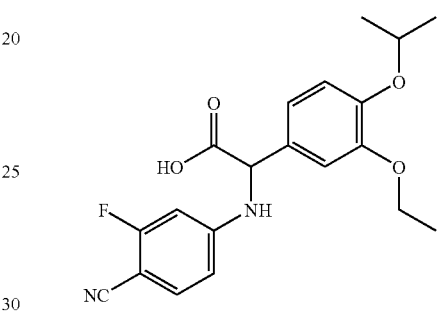

To a solution of 43B (119 mg, 0.308 mmol) in 5 mL THF/H$_2$O (4:1), was added 339 μL 1N LiOH. The mixture was stirred at rt for 1 h, then THF was evaporated. The mixture was diluted with EtOAc/H$_2$O and was acidified with 1N HCl. The phases were separated and the aqueous phase was extracted with EtOAc (3×). The combined organic phase was washed with brine, dried (Na$_2$SO$_4$) and concentrated to afford 115 mg of 43C, which was used in the following step without further purification.

43D

N-[2-(4-Cyano-3-fluoro-phenylamino)-2-(3-ethoxy-4-isopropoxy-phenyl)-acetyl]-benzenesulfonamide To a solution of 43C (115 mg, 0.309 mmol) in 3 mL CH$_2$Cl$_2$/DMF (4:1) at rt, were added TEA (215 μL, 1.54 mmol), BOP (164 mg, 0.371 mmol), and PhSO$_2$NHTMS (142 mg, 0.618 mmol). The mixture was stirred at rt for 4 h, then concentrated. The crude residue was purified by preparative LC/MS to afford 75 mg of 43D. LC-MS: 510.36 (M−H)$^+$.

43E

Example 43

To a solution of N-hydroxy-acetamide (29 mg, 0.39 mmol) in 0.5 mL DMF at rt, was added potassium tert-butoxide (44 mg, 0.39 mmol). The mixture was stirred at rt 30 min, then 43D (20 mg, 0.039 mmol) was added. The mixture was stirred at 90° C. for 18 h. The crude mixture was purified by preparative LC/MS chromatography to afford 8.0 mg of Example 43 as the trifluoroacetic acid salt. LC-MS: 525.42 (M+H)$^+$.

EXAMPLE 44

N-[2-(3-Amino-1H-indazol-6-ylamino)-2-(3-ethoxy-4-isopropoxy-phenyl)-acetyl]-benzenesulfonamide trifluoroacetic acid salt

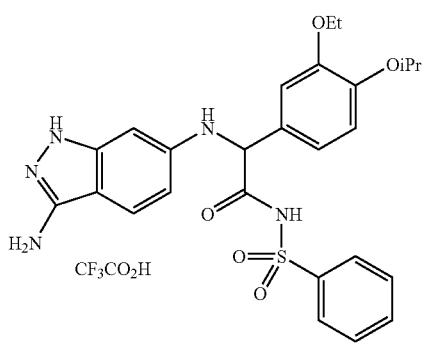

To a solution of hydrazinecarboxylic acid tert-butyl ester (51.7 mg, 0.39 mmol) in 0.5 mL DMF, was added potassium tert-butoxide (44 mg, 0.39 mmol). The mixture was stirred at rt for 30 min, then 43D (20 mg, 0.039 mmol) was added. The mixture was stirred at 90° C. for 15 h, then 120° C. for 2 h. Hydrazine (3 drops) was added and the mixture was stirred at 160° C. for 4 h, then at 120° C. for 64 h. The crude mixture was purified by preparative LC/MS chromatography to afford 8.0 mg of Example 44 as the trifluoroacetic acid salt. LC-MS: 524.37 (M+H)$^+$.

EXAMPLE 45

N-[2-(2-Amino-3H-benzoimidazol-5-ylamino)-2-(3-ethoxy-4-isopropoxy-phenyl)-acetyl]-benzene-sulfonamide trifluoracetic acid salt

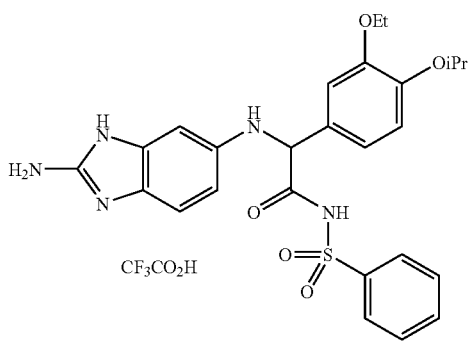

45A

6-Nitro-1H-benzoimidazol-2-ylamine

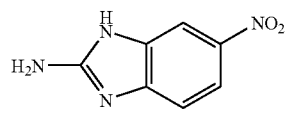

To a mixture of 4-nitro-1,2-phenylenediamine (1.00 g, 6.53 mmol) in 4:1 ethanol/water (25 mL), was added cyanuric bromide. The mixture was stirred at rt for 3 days. The ethanol was evaporated and the mixture was made basic with ammonium hydroxide. The mixture was diluted with 20 mL H$_2$O, cooled to 0° C. for 1 h, then the resultant precipitated was collected by filtration to afford 1.15 g of 45A as a greenish tan solid. $^1$H NMR (400 MHz, D$_6$-DMSO) δ 7.93 (d, J=2.2, 1H), 7.88 (dd, J=8.8, 2.2, 1H), 7.17 (d, J=8.8, 1H), 6.94 (s, 2H).

45B

Boc-Protected 6-nitro-1H-benzoimidazol-2-ylamine

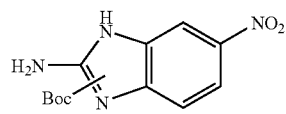

To a mixture of 45A (200 mg, 1.12 mmol) in 5 mL MeOH, was added Boc$_2$O (244 mg, 1.12 mmol) and catalytic DMAP. The mixture was stirred for 3 h, then concentrated. The crude residue was dissolved in EtOAc and a small amount of THF, then filtered through a 1" pad of SiO$_2$. The filtrate was concentrated to afford 307 mg of 45B as a mixture of Boc-protected isomers, which was used without further purification in the following step.

45C

Boc-Protected 3H-Benzoimidazole-2,5-diamine

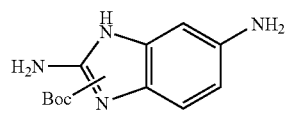

To a solution of 45B (307 mg) in 5 mL MeOH, was added 50 mg 10% Pd—C. The mixture was evacuated and flushed with H$_2$ (3×), then was stirred under an atmosphere of H$_2$ for 3 h. The mixture was filtered and concentrated to afford 307 mg of 45C, which was used without purification in the following step.

45D

Boc-Protected (2-Amino-1H-benzoimidazol-5-ylamino)-(3-ethoxy-4-isopropoxy-phenyl)-acetic acid methyl ester

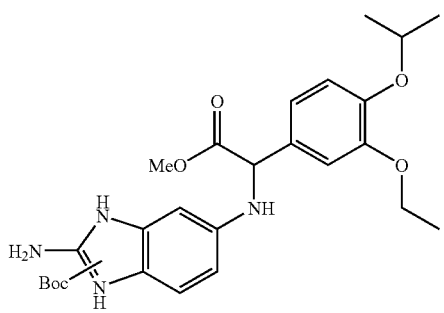

A mixture of 45C (275 mg, 1.12 mmol), compound 43A (160 mg, 0.558 mmol), and DIEA (293 μL, 1.68 mmol) in 5 mL DMF, was stirred at 50° C. for 18 h. The mixture was diluted with EtOAc, washed with water (2×) and brine, dried (Na$_2$SO$_4$) and concentrated. The crude residue was purified by flash chromatography (step gradient elution: 30 to 35 to 40% acetone/hexanes) to afford 270 mg of 45D as a mixture of Boc-protected isomers.

45E

Boc-Protected (2-amino-1H-benzoimidazol-5-ylamino)-(3-ethoxy-4-isopropoxy-phenyl)-acetic acid

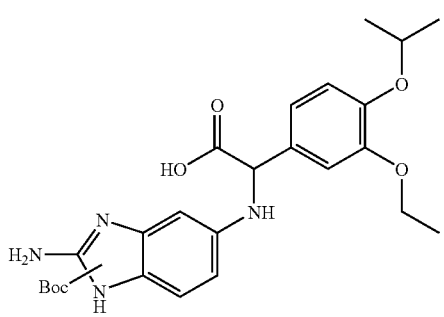

A mixture of 45D (164 mg, 0.329 mmol) in THF (3 mL) and 1 M LiOH (0.362 mL, 0.362 mmol) was stirred at rt for 3 h. The THF was evaporated. The mixture was diluted with 5 mL H$_2$O, then neutralized (pH=7) with 1N HCl. The mixture was extracted with EtOAc (2×). The aqueous phase was acidified to pH 6 with the addition of 1N HCl, then extracted with EtOAc (2×). The aqueous phase was acidified to pH 5 with the addition of 1N HCl, then extracted with EtOAc (2×). The combined organic phase was washed with brine, dried (Na$_2$SO$_4$), and concentrated to afford 130 mg of 45E.

45F

Example 45

To a solution of 45E (40 mg, 0.083 mmol) in 1 mL CH$_2$Cl$_2$/DMF (8:1) at rt, were added TEA (58 mL, 0.413 mmol), PhSO$_2$NHTMS (38 mg, 0.165 mmol), and BOP (44 mg, 0.099 mmol). The mixture was stirred at rt for 3 h, then diluted with EtOAc. The organic phase was washed with H$_2$O and brine, dried (Na$_2$SO$_4$) and concentrated to afford the acylsulfonamide product. (LC-MS: 624.57 (M+H)$^+$). The crude Boc-protected material was dissolved in 5 mL 20% TFA/CH$_2$Cl$_2$ and stirred 30 min at rt. The solvent was evaporated and the crude material was purified by preparative LC-MS to afford 6.2 mg of Example 45 as a tan solid. LC-MS: 524.27 (M+H)$^+$.

EXAMPLE 46

2-(4-aminoquinazolin-7-ylamino)-2-(3-ethoxy-4-isopropoxyphenyl)-N-(phenylsulfonyl)acetamide trifluoroacetic acid salt

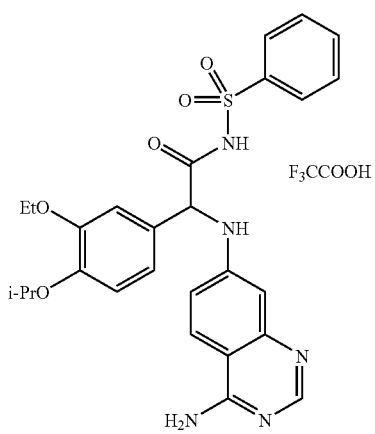

46A 7-nitroquinazolin-4(3H)-one

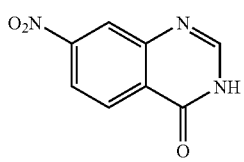

A mixture of 4-nitroanthranilic acid (2.07 g, 11.4 mmol) and formamide (2 mL, 50 mmol) was heated to 200° C. (oil bath temperature) with stirring for 1.5 h. Water (4 mL) was added to the cooled reaction mixture. The resulting slurry was filtered and washed with ethanol (3×) to afford 46A (2.048 g, 94%) as brown crystals. LC-MS: 192.2 (M+H)$^+$.

46B 4-chloro-7-nitroquinazoline

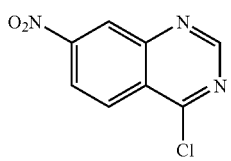

A mixture of 46A (1.32 g, 6.91 mmol), phosphorous oxychloride (2.40 mL, 25.8 mmol), and phosphorous pentachloride (2.1 g, 10.1 mmol) was heated at reflux for 5 h. The cooled solid was suspended in hexanes, filtered, and washed with hexanes. The recovered solid was dissolved in dichloromethane and washed with aqueous sodium hydroxide (1 M). The organic layer was dried and concentrated on a rotary evaporator to afford 46B (1.246 g, 86%) as light orange crystals. LC-MS: 210.1 (M+H)$^+$.

46C

N-(2,4-dimethoxybenzyl)-7-nitroquinazolin-4-amine

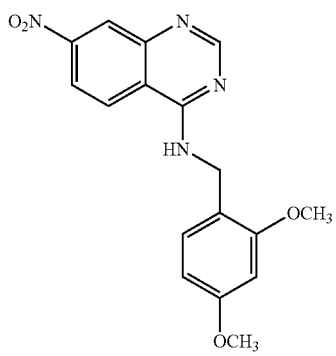

To a solution of 46B (192 mg, 0.916 mmol) and triethylamine (0.19 mL, 1.36 mmol) in dimethylformamide (2 mL, was added 2,4-dimethoxybenzylamine (0.14 mL, 0.93 mmol). The mixture was stirred at 50° C. for 1 h. Water (10 mL) was added and the resulting suspension was filtered, washed with water, and dried to give 46C (0.231 g, 74%) as a yellow solid. LC-MS: 341.25 (M+H)$^+$.

46D

N$^4$-(2,4-dimethoxybenzyl)quinazoline-4,7-diamine

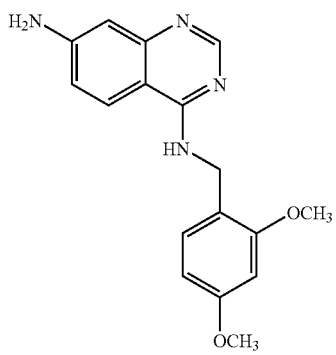

To a solution of 46C (120 mg, 0.353 mmol) in ethanol (2 mL), was added 10% palladium on carbon (30 mg). The reaction flask was evacuated, flushed with hydrogen (3×), and then stirred under hydrogen (1 atm) for 4 h. The reaction mixture was filtered, concentrated, and dissolved in ethanol (5 mL). 10% Palladium on carbon (23 mg) was added. The reaction flask was evacuated, flushed with hydrogen (3×), and then stirred under hydrogen (60 psi) for 3 h. The mixture was filtered and concentrated to afford 46D (93 mg, 85%) as a yellow oil. LC-MS: 311.3 (M+H)$^+$.

46E

Benzyl 2-(4-(2,4-dimethoxybenzylamino)quinazolin-7-ylamino)-2-(3-ethoxy-4-isopropoxyphenyl) acetate

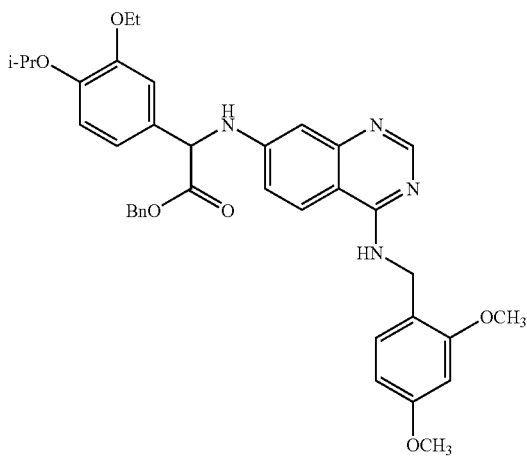

To a mixture of 46D (85 mg, 0.274 mmol) and 5F (101 mg, 0.278 mmol) in dimethylformamide (1 mL) was added diisopropylethylamine (0.240 mL). The reaction mixture was stirred at 25° C. for 1.5 h, 45° C. for 4 h, 70° C. for 2.5 h, and 90° C. for 22 h. The cooled reaction mixture was diluted with ethyl acetate and extracted with hydrochloric acid (1N) and sodium bicarbonate solution (saturated). The organic layer was dried and concentrated. The residue was purified by silica gel chromatography (Chromatotron) using a gradient of 20 to 100% (v/v) ethyl acetate in hexane, to afford 46E (27.7 mg, 16%). LC-MS: 637.29 (M+H)$^+$.

46F 2-(4-(2,4-dimethoxybenzylamino)quinazolin-7-ylamino)-2-(3-ethoxy-4-isopropoxyphenyl)acetic acid

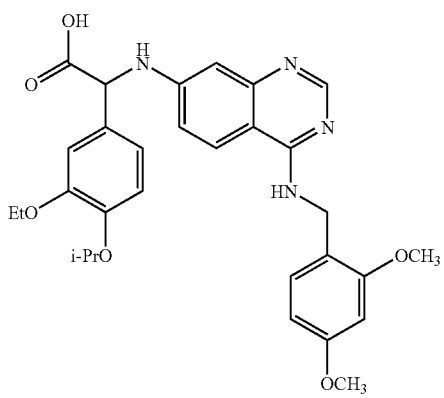

To a solution of 46E (58 mg, 0.09 mmol) in ethanol (2 mL), was added 10% palladium on carbon (26 mg). The reaction flask was evacuated, flushed with hydrogen (3×), and then stirred under hydrogen (1 atm) for 4 h. The reaction mixture was filtered and concentrated to afford 46F (50 mg, 100%) as a yellow foam. LC-MS: 547.26 (M+H)$^+$.

46G

Example 46

2-(4-aminoquinazolin-7-ylamino)-2-(3-ethoxy-4-isopropoxyphenyl)-N-(phenylsulfonyl)acetamide trifluoroacetic acid salt

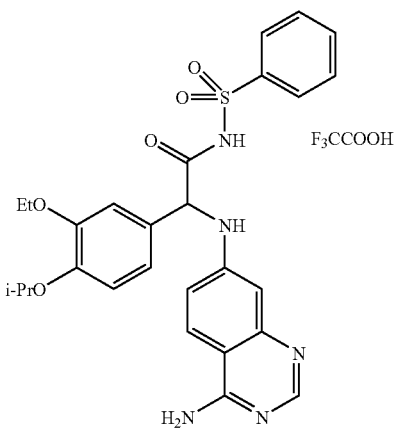

To a solution of 46F (20 mg, 0.036 mmol) in dichloromethane (0.2 mL) was added triethylamine (0.025 mL, 0.179 mmol), PhSO₂NHTMS (24 mg, 0.105 mmol), and BOP (21 mg, 0.046 mmol). The reaction mixture was stirred at rt for 1 h. The solvent was evaporated and the crude material was purified by preparative LC-MS to afford a yellow solid. This material was dissolved in 1:1 trifluoroacetic acid/dichloromethane (0.4 mL) and stirred 1 h at rt. The solvent was evaporated and the crude material was purified by preparative LC-MS to afford Example 46 (5 mg, 26%) as a white amorphous solid. LC-MS: 536.21 (M+H)⁺. ¹H NMR (400 MHz, CD₃OD) δ 8.39 (s, 1H), 7.94(d, 1H), 7.84 (d, 2H), 7.63 (t, 1H), 7.48 (t, 2H), 7.09 (d, 1H), 6.88 (dd, 2H), 6.82 (s, 1H), 6.45 (br s, 1H), 5.01 (s, 1H), 4.52 (m, 1H), 3.91 (m, 1H), 3.82 (m, 1H), 1.35 (t, 3H), 1.30 (d, 6H).

EXAMPLE 47

2-(4-aminoquinazolin-7-ylamino)-2-(3-ethoxy-4-isopropoxyphenyl)-N-(methylsulfonyl)acetamide trifluoroacetic acid salt

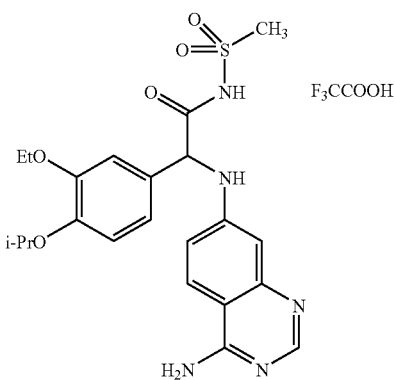

To a solution of 46F (20 mg, 0.036 mmol) in dichloromethane (0.5 mL) was added triethylamine (0.025 mL, 0.179 mmol), CH₃SO₂NHTMS (18 mg, 0.108 mmol), and BOP (21 mg, 0.046 mmol). The reaction mixture was stirred at rt for 1 h. The solvent was evaporated and the residue was purified by preparative LC-MS. This material was dissolved in 1:1 trifluoroacetic acid/dichloromethane (0.4 mL) and stirred 1 h at rt. The solvent was evaporated and the crude material was purified by preparative LC-MS to afford to afford Example 47 (9 mg, 53%) as a white amorphous solid. LC-MS: 474.24 (M+H)⁺. ¹H NMR (400 MHz, CD₃OD) δ 8.40 (s, 1H), 8.00 (d, 1H), 7.17 (dd, 1H), 7.11 (d, 1H), 7.07 (dd, 1H), 7.00 (d, 1H), 6.51 (br s, 1H), 5.10 (s, 1H), 4.55 (m, 1H), 4.08 (q, 2H), 3.22 (s, 3H), 1.40 (t, 3H), 1.30 (d, 6H),

EXAMPLE 48

2-(1-Aminoisoquinolin-6-ylamino )-2-(3-ethoxy-4-isopropoxyphenyl)-N-(2,2,2-trifluoroethylsulfonyl)acetamide trifluoroacetic acid salt

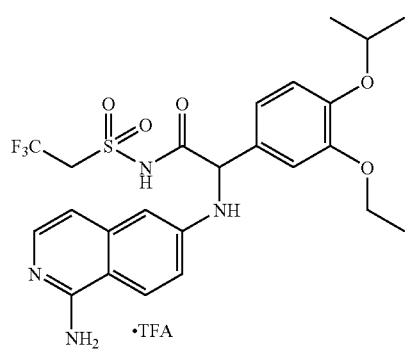

48A 2,2,2-trifluoro-N-(trimethylsilyl)-ethanesulfonamide:

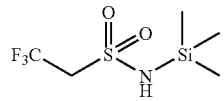

2,2,2-Trifluoroethanesulfonyl chloride (1.00 g, 5.48 mmol) and 1,1,1,3,3,3-hexamethyldisilazane (1.30 mL, 6.23 mmol) were stirred for 2 h at 100° C. After cooling to rt, the reaction was filtered and concentrated to provide 48A (1.08 g).

48B

Example 48

Example 48 was prepared from 48A and acid 5H using procedures analogous to those used in Example 5. ¹H NMR (400 MHz, CD₃OD) δ 8.06 (d, J=9.2, 1H), 7.30 (d, J=7.1, 1H), 7.17–7.04 (m, 3H), 6.95 (d, J=8.3, 1H), 6.84 (d, J=7.1, 1H), 6.66 (d, J=2.2, 1H), 5.05 (s, 1H), 4.52 (septet, J=6.1, 1H), 4.07 (q, J=7.0, 2H), 3.51 (m, 2H), 1.38 (t, J=7.0, 3H), 1.28 (d, J=5.7, 6H); MS: 541.17 (M+H)⁺

EXAMPLE 49

2-(1-Aminoisoquinolin-6-ylamino)-N-(cyclopropyl-sulfonyl)-2-(3-ethoxy-4-isopropoxyphenyl)acetamide trifluoroacetic acid salt

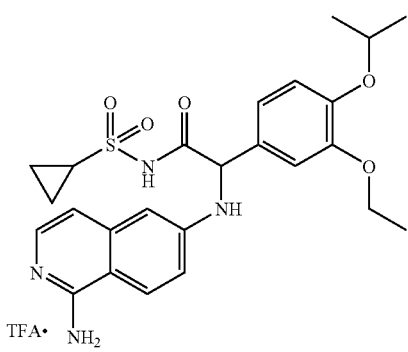

Example 49 was prepared from N-(trimethylsilyl)cyclopropanesulfonamide (accessible from cyclopropanesulfonamide according to the following reference: Roy, A. K. *J. Am. Chem. Soc.* 1993, 15, 2598) and acid 5H using procedures analogous to those used in Example 5. MS: 499.10 (M+H)+

EXAMPLE 50

2-(1-Aminoisoquinolin-6-ylamino)-N-(3-aminosulfonyl-phenylsulfonyl)-2-(3-ethoxy-4-isopropoxyphenyl)acetamide trifluoroacetic acid salt

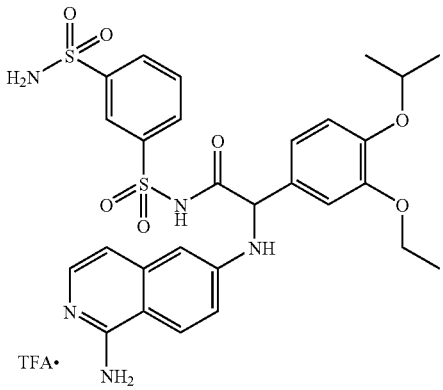

50A:

N-1-(trimethylsilyl)benzene-1,3-disulfonamide

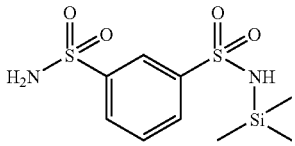

To benzene-1,3-disulfonamide (118 mg, 0.499 mmol) in benzene (3 mL) was added TEA (111 mg, 1.10 mmol). The whole was cooled to 0° C. and chlorotrimethylsilane (109 mg, 1.00 mmol) was added. The reaction was warmed to 79° C. for 48 h then cooled to rt, filtered and concentrated to provide 50A (156 mg).

50B

Example 50

Example 50 was prepared from 50A and acid 5H using procedures analogous to those used in Example 5. $^1$H NMR (400 MHz, CD$_3$OD) δ 8.33 (m, 1H), 8.00–7.94 (m, 2H), 7.94 (d, J=3.9, 1H), 7.54 (t, J=7.9, 1H), 7.22 (d, J=1H), 6.99 (dd, J=2.2, 9.3, 1H), 6.84–6.72 (m, 3H), 6.64 (d, J=7.0, 1H), 6.38 (d, J=2.2 1H), 4.92 (s, 1H), 4.44 (septet, J=6.0, 1H), 3.92–3.78 (m, 2H), 1.28 (t, J=7.0, 3H), 1.20 (dd, J=1.5, 5.9, 6H); MS: 614.17 (M+H)+

EXAMPLE 51

2-(3-Ethoxy-4-isopropoxyphenyl)-2-(isoquinolin-6-ylamino)-N-(phenylsulfonyl)-acetamide trifluoroacetic acid salt

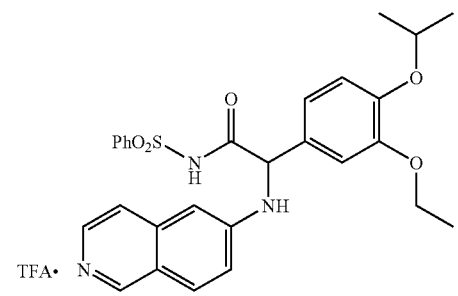

51A:

2-Amino-2-(3-ethoxy-4-isopropoxyphenyl)acetonitrile

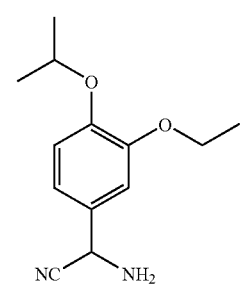

3-Ethoxy-4-isopropoxybenzaldehyde (2A) (19.5 g, 93.6 mmol) was dissolved in a 7N MeOH solution of ammonia (240 mL) and the whole was cooled to 0° C. Trimethylsilyl cyanide (19.2 mL 144 mmol) was added and the reaction was stirred overnight with gradual warming to rt. The reaction was concentrated then purified via silica gel chromatography (eluting with 0–45% ethyl acetate in hexane) to provide 51A (16.8 g).

51B

Methyl 2-amino-2-(3-ethoxy-4-isopropoxyphenyl)acetate

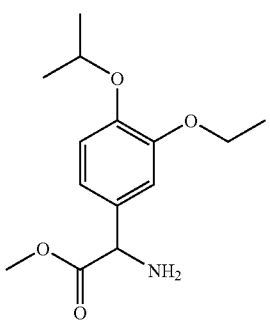

Compound 51A (9.78 g, 41.8 mmol) was dissolved in MeOH (200 mL) and HCl (g) was bubbled through the system for 10 min. The reaction was brought to reflux for 4 h and was then concentrated and dissolved in methylene chloride. The organic solution was washed with brine and saturated aqueous sodium bicarbonate, dried (Na$_2$SO$_4$), and purified via silica gel chromatography (eluting with 0–85% ethyl acetate in hexane) to provide 51B (8.80 g) LC/MS: 268.15 (M+H)$^+$

51C

Methyl 2-(3-ethoxy-4-isopropoxyphenyl)-2-(isoquinolin-6-ylamino)acetate

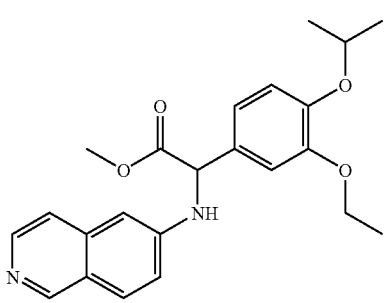

Compound 51B (172 mg, 0.640 mmol), 6-bromoisoquinoline (140 mg, 0.670 mmol), cesium carbonate (626 mg, 1.92 mmol), racemic BINAP (20.0 mg, 0.0321 mmol) and Pd$_2$(dba)$_3$ (10 mg, 0.0109 mmol) were combined in a sealed tube and the whole was degassed for 5 min with nitrogen. Toluene (3 mL) was added and the reaction was sealed and heated to 100° C. for 20 h. After cooling to rt, the reaction was diluted with ethyl acetate and was washed with brine. The organic layer was dried (Na$_2$SO$_4$), filtered and concentrated. The resulting residue was purified via silica gel chromatography (eluting with 10–90% ethyl acetate in hexane) to provide 51C (182 mg). LC/MS: 395.20 (M+H)$^+$

51D

2-(3-Ethoxy-4-isopropoxyphenyl)-2-(isoquinolin-6-ylamino)acetic acid hydrochloric acid salt

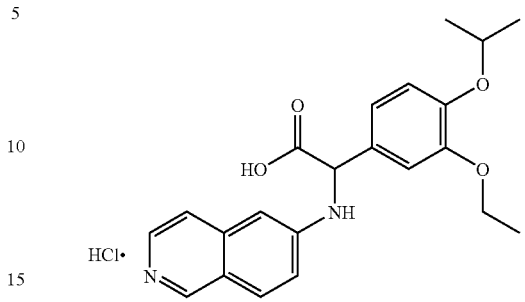

Compound 51C (406 mg, 1.03 mmol) was dissolved in THF (10 mL) and a 1 M aqueous LiOH solution (3 mL) was added. The reaction was stirred at rt for 1 h and was then concentrated. The residue was dissolved in water (20 mL) and was washed with ethyl acetate (2×10 mL). The aqueous layer was acidified with 1 N HCl to provide a yellow precipitate. The whole was cooled in an ice bath then filtered and dried to provide 51D (230 mg). MS: 381.18 (M+H)$^+$

51E

Example 51

To 51D (38.0 mg, 0.0913 mmol) in 2 mL CH$_2$Cl$_2$/DMF (10:1) was added PhSO$_2$NHTMS (305 mg, 1.33 mmol) (prepared according to the following reference: Roy, A. K. J. Am. Chem. Soc. 1993, 115, 2598). BOP (54.0 mg, 0.120 mmol) and TEA (0.05 mL). The mixture was stirred at rt for 1 h, then was concentrated. The resulting residue was purified via preparative chromatography (eluting with CH$_3$CN/H$_2$O/TFA) to afford Example 51 (51.0 mg). $^1$H NMR (500 MHz, CD$_3$OD) δ 8.98 (s, 1H), 8.02 (d, J=7.1, 1H), 7.94 (d, J=9.4, 1H), 7.78 (d, J=7.2, 2H), 7.64 (d, J=6.6, 1H), 7.54 (t, J=7.7, 1H), 7.39 (t, J=8.0, 2H), 7.31 (d, J=8.8, 1H), 6.82 (m, 2H), 6.78 (s, 1H), 6.59 (br s, 1H), 5.05 (s, 1H), 4.44 (septet J=6.1, 1H), 3.88–3.74 (m, 2H), 1.27 (t, J=6.9, 3H), 1.21 (dd, J=2.2, 6.1, 6H); MS: 520.19 (M+H)$^+$

51F

Chiral Separation of 51E 210 mg of racemic 51E was chromatographed on a 5.0 cm×50.0 cm Chiralpak AD column eluting with 25%–40% IPA/heptane with 0.1% TFA at 50 mL/min to afford enantiomer 1 (90 mg) followed by enantiomer 2 (81 mg).

Example 52

N-(3-Cyanophenylsulfonyl)-2-(3-ethoxy-4-isopropoxyphenyl)-2-(isoquinolin-6-ylamino)acetamide trifluoroacetic acid salt

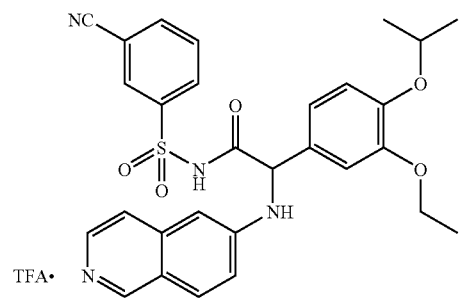

Example 52 was prepared from 3-cyano-N-(trimethylsilyl)-benzenesulfonamide (accessible from 3-cyanobenzenesulfonamide according to the following reference: Roy, A. K. *J. Am. Chem. Soc.* 1993, 115, 2598) and acid 51D following a procedure analogous to that used in Example 51. MS: 545.19 (M+H)+

EXAMPLE 53

N-(3-Aminosulfonyl-phenylsulfonyl)-2-(3-ethoxy-4-isopropoxyphenyl)-2-(isoquinolin-6-ylamino)acetamide trifluoroacetic acid salt

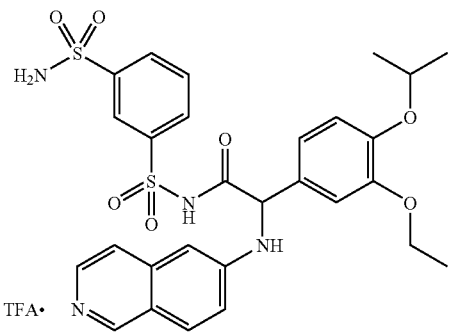

Example 53 was prepared from 50A and acid 51D following a procedure analogous to that used in Example 51. 1H NMR (400 MHz, CD3OD) δ 9.05 (s, 1H), 8.43 (m, 1H), 8.11–8.06 (m, 3H), 8.03 (d, J=9.1, 1H), 7.68 (d, J=70, 1H), 7.64 (t, J=7.5, 1H), 7.39 (dd, J=2.2, 9.2, 1H), 6.95–6.90 (m, 3H), 6.62 (br s, 1H), 5.13 (s, 1H), 4.55 (septet, J=6.1, 1H), 4.02–3.87 (m, 2H), 1.37 (t, J=7.0, 3H), 1.30 (dd, J=1.6, 5.9, 6H); MS: 599.16 (M+H)+

53B

Chiral Separation of 53

180 mg of racemic 53 was chromatographed on a 5.0 cm×50.0 cm Chiralpak AD column eluting with 50% IPA/heptane with 0.1% TFA at 50 mL/min to afford enantiomer 1 (69 mg) followed by enantiomer 2 (71 mg).

EXAMPLE 54

N-(Cyclopropylsulfonyl)-2-(3-ethoxy-4-isopropoxyphenyl)-2-(isoquinolin-6-ylamino)acetamide trifluoroacetic acid salt

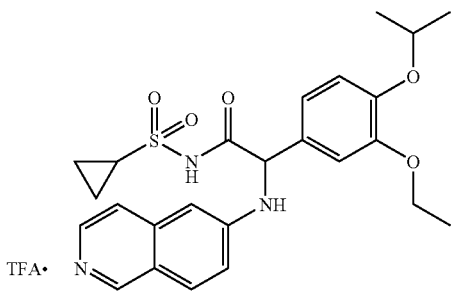

Example 54 was prepared from N-(trimethylsilyl)cyclopropanesulfonamide (accessible from cyclopropanesulfonamide according to the following reference: Roy, A. K. *J. Am.*

*Chem. Soc.* 1993, 115, 2598) and acid 51D following a procedure analogous to that used in Example 51. 1H NMR (400 MHz, CD3OD) δ 9.09 (s, 1H), 8.11 (t, J=7.9, 2H), 7.84 (d, J=7.0, 1H), 7.50 (dd, J=2.2, 9.2, 1H), 7.14 (d, J=2.2, 1H), 7.10 (dd, J=2.0, 8.1, 1H), 7.01 (d, J=8.3, 1H), 6.85 (br s, 1H), 5.22 (s, 1H), 4.56 (septet, J=6.40, 1H), 4.08 (q, J=7.0 2H), 3.30 (pentet, J=1.6, 1H), 1.40 (t, J=7.0, 3H), 1.30 (d, J=6.2, 6H), 1.27–0.94 (m, 4H); MS: 484.06 (M+H)+

EXAMPLE 55

N-(3-Carboxamide-phenylsulfonyl)-2-(3-ethoxy-4-isopropoxyphenyl)-2-(isoquinolin-6-ylamino)acetamide trifluoroacetic acid salt

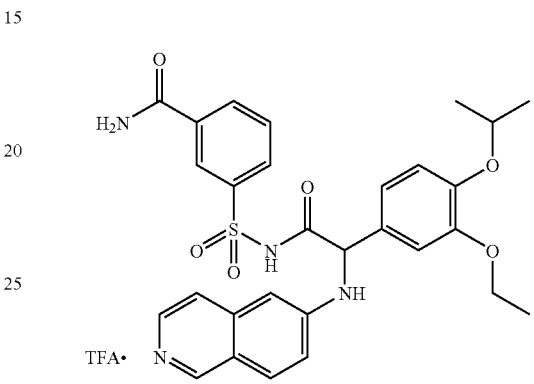

55A 3-(Aminosulfonyl)benzamide

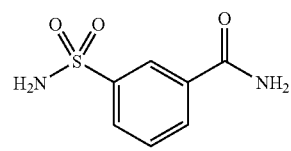

To 3-(chlorosulfonyl)benzoyl chloride (956 mg, 4.00 mmol) in THF (4 mL) at 0° C. was added a 30% aqueous solution of ammonium hydroxide (1.6 mL). The reaction was stirred for 30 min (0° C. to rt). Water was added and the product was extracted with ethyl acetate. The organic layer was washed with brine, dried (Na2SO4), filtered and concentrated to provide 55A (705 mg). LC/MS: 199.13 (M−H)−

55B

N1,N3-Bis(trimethylsilyl)-3-(aminosulfonyl)benzamide

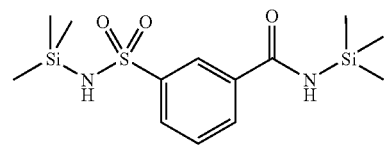

To 55A (200 mg, 1.00 mmol) in benzene (3 mL) was added chlorotrimethylsilane (218 mg, 2.00 mmol) and TEA (223 mg, 2.20 mmol) and the whole was heated to 80° C. in a sealed tube for 16 h. The reaction was cooled to rt then filtered and concentrated to provide 55B (100 mg).

55C

Example 55

Example 55 was prepared from 55B and acid 51D following a procedure analogous to that used in Example 51. LC/MS: 563.24 (M+H)+

EXAMPLE 56

N-(2-Aminoethylsulfonyl)-2-(3-ethoxy-4-isopropoxyphenyl)-2-(isoquinolin-6-ylamino)acetamide ditrifluoroacetic acid salt

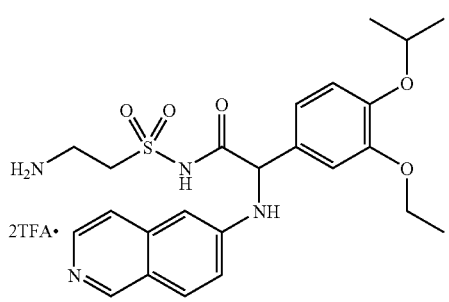

56A

N-(2-(1,3-Dioxoisoindolin-2-yl)ethylsulfonyl)-2-(3-ethoxy-4-isopropoxyphenyl)-2-(isoquinolin-6-ylamino)acetamide trifluoroacetic acid salt

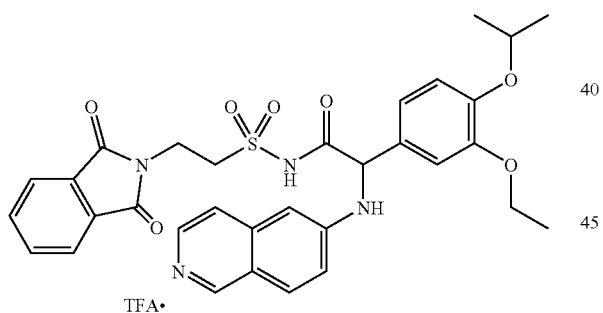

Compound 56A was prepared from 2-(1,3-dioxoisoindolin-2-yl)-N-(tritmethylsilyl)ethanesulfonamide (accessible in two steps from commercially available 2-(1,3-dioxoisoindolin-2-yl)ethanesulfonyl chloride according to procedures found in Example 55 and in the following reference: Roy, A. K. *J. Am. Chem. Soc.* 1993, 115, 2598) and acid 51D following a procedure analogous to that used in Example 51. LC/MS: 617.25 (M+H)+

56B

Example 56

To 56A (37.0 mg, 0.0600 mmol) in EtOH (4 mL) was added hydrazine (8 drops) and the whole was warmed to 50° C. for 1 h. The reaction was cooled to rt then concentrated and purified via preparative HPLC using MeOH/water/TFA as an eluent. Two products were isolated: the first to elute was Example 56 (15.0 mg, LC/MS: 487.21 [M+H]+) followed by N-(2-sulfamoylethyl)-2-(3-ethoxy-4-isopropoxyphenyl)-2-(isoquinolin-6-ylamino)acetamide (12 mg, LC/MS: 487.25 [M+H]+).

EXAMPLE 57

2-(1-Aminoisoquinolin-6-ylamino)-N-(3-carboxamide-plenylsulfonyl)-2-(3-ethoxy-4-isopropoxyphenyl) trifluoroacetic acid salt

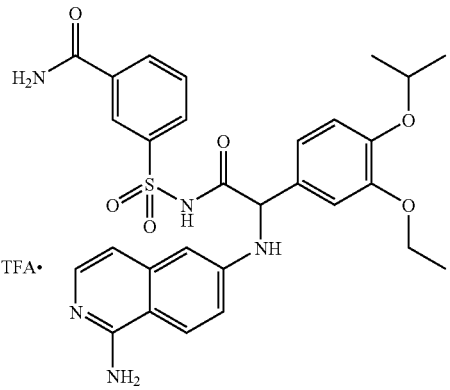

Example 57 was prepared from 3-(aminosulfonyl)benzamide (55A) and acid 5H using procedures analogous to those used in Example 5. MS: 578.19 (M+H)+

EXAMPLE 58

2-(1-Aminoisoquinolin-6-ylamino)-2-(3-ethoxy-4-isopropoxyphenyl)-N-(methylsulfonyl)acetamide hydrochloride salt

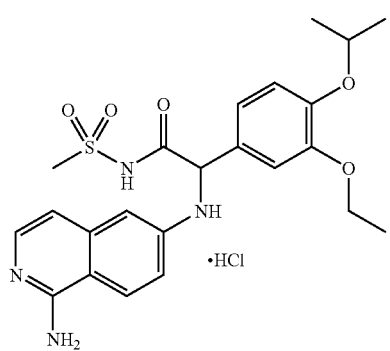

58A

6-Nitro-1-bis(tert-butyl carbonyl)aminoisoquinoline

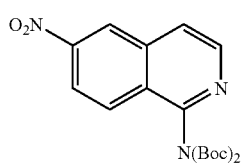

A mixture of 6-nitroisoquinolin-1-amine (23, Scheme K, 50 mg) and di-tert-butyl dicarbonate (200 mg) was heated at 130° C. for 1.0 h. The crude residue was purified by flash chromatography (25% EtOAc/hexanes) to afford 78 mg (78% yield) of 58A as a solid. $^1$H NMR (400 MHz, CDCl$_3$) δ ppm 1.33 (s, 18 H) 7.86 (d, J=5.27 Hz, 1 H) 8.15 (d, J=9.23 Hz, 1 H) 8.39 (dd, J=9.23, 2.20 Hz, 1 H) 8.62 (d, J=5.71 Hz, 1 H) 8.82 (d, J=2.20 Hz, 1 H). LC-MS: 801 (2M+Na).

58B

6-Amino-1-bis(tert-butyl carbonyl)aminoisoquinoline

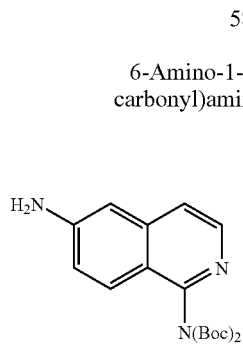

58A (55 mg) in methanol (2.5 mL) was hydrogenated with a hydrogen balloon in the presence of Pd/C (10%, 35 mg) for 2.0 h. Filtration of the Pd/C and concentration gave the product as a white solid (47 mg, 92%). $^1$H NMR (400 MHz, CDCl$_3$) δ ppm 1.33 (m, 18 H) 4.18 (s, 2 H) 6.89 (d, J=2.20 Hz, 1 H) 6.99 (dd, J=901, 2.42 Hz, 1 H) 7.35 (d, J=6.59 Hz, 1 H) 7.75 (d, J=8.79 Hz, 1 H) 8.22 (d, J=5.71 Hz, 1H), LC-MS: 741 (2M+Na).

58C

Benzyl 2-(1-bis(tert-butyl carbonyl)aminoisoquino-lin-6-ylamino)-2-(3-ethoxy-4-isopropoxyphenyl) acetate

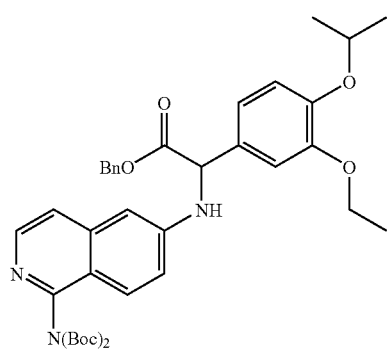

To a mixture of 58B (43 mg, 0.12 mmol) and 5F (87 mg, 0.24 mmol) in acetonitrile (1.0 mL) was added DIPEA (63 μl, 0.26 mmol). The mixture was heated at 80° C. for 3 h. After it cooled to rt, it was quenched with 5% citric acid, extracted with EtOAc and dried over Na$_2$SO$_4$. The crude residue was purified by flash chromatography (35% EtOAc/hexanes) to afford 58C (73 mg, 80% yield) as a solid. $^1$H NMR (400 MHz, CDCl$_3$) δ ppm 1.34 (m, 27 H) 3.98 (m, 2 H) 4.48 (m, 1 H) 5.18 (m, 3 H) 5.40 (d, J=5.27 Hz, 1 H) 6.53 (d, J=2.20 Hz, 1 H) 6.89 (d, J=7.91 Hz, 1 H) 7.01 (m, 4 H) 7.22 (m, 4 H) 7.31 (m, 4 H) 7.71 (d, J=8.79 Hz, 1 H) 8.18 (d, J=5.71 Hz, 1 H). LS-MS: 686 (M+H).

58D 2-(1-Bis(tert-butyl carbonyl)amino isoquinolin-6-ylamino)-2-(3-ethoxy-4-isopropoxyphenyl)acetic acid

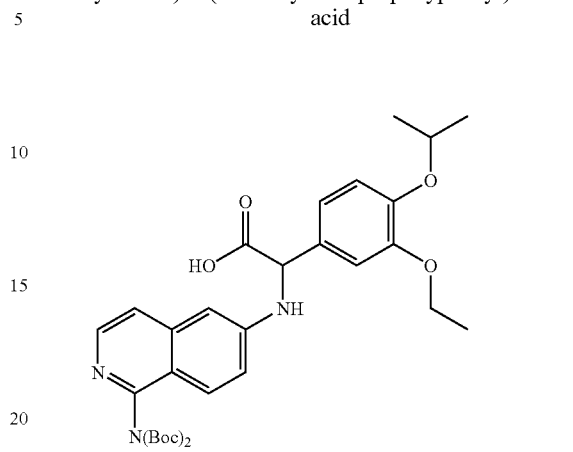

58C (475 mg) in methanol (10 mL) was hydrogenated with a hydrogen balloon in the presence of with Pd/C (10%, 150 mg) for 2.0 h. Filtration of the Pd/C and concentration gave compound 58D as a white solid (385 mg). $^1$ H NMR (400 MHz, CDCl$_3$) δ ppm 1.24 (s, 18 H) 1.31 (t, J=5.49 Hz, 6 H) 1.37 (t, J=7.03 Hz, 3 H), 4.04 (m, 2 H) 4.45 (m, 1 H) 5.07 (s, 1 H) 6.53 (d, J=1.76 Hz, 1 H) 6.88 (d, J=7.91 Hz, 1 H) 7.08 (m, 3 H) 7.31 (d, J=6.15 Hz, 1 H) 7.72 (d, J=9.23 Hz, 1 H) 8.17 (d, j=5.71 Hz, 1 H). LC-MS: 596 (M+H).

58E 2-(1-Bis(tert-butyl carbonyl)aminoisoquinolin-6-ylamino)-2-(3-ethoxy-4-isopropoxyphenyl)-N-(methylsulfonyl)acetamide

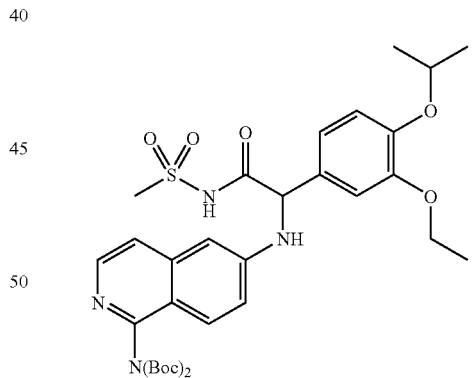

A mixture of 58D (100 mg, 0.1.7 mmol), N-(trimethylsilyl)methanesulfonamide (56 mg, 0.34 mmol), BOP (89.2 mg, 0.2 mmol), and Et$_3$N (117 μL, 0.85 mmol) in CH$_2$Cl$_2$ (1.0 mL) was stirred at rt for 2 h, then was diluted with EtOAc, washed with H$_2$O and brine, dried (Na$_2$SO$_4$), and concentrated. The crude material was purified via reverse phase preparative HPLC (eluting with CH$_3$CN/H$_2$O/TFA) to afford 77 mg (68% yield) of 58E. $^1$H NMR (400 MHz, CDCl$_3$) δ ppm 1.23 (m, 24 H) 1.31 (t, J=7.03 Hz, 3 H) 3.15 (s, 3 H) 4.00 (q, J=7.03 Hz, 2 H) 4.47 (m, 1 H) 5.10 (s, 3 H) 6.93 (d, J=8.35 Hz, 1 H) 7.00 (d, J=2.20 Hz, 1 H) 7.02 (d, J=1.76 Hz, 1 H) 7.06 (d, J=2.20 Hz, 1 H) 7.33 (dd, J=9.23, 2.20 Hz, 1 H 7.60 (d, J=6.15 Hz, 1 H) 7.73 (d, J=9.67 Hz, 1 H) 8.03 (d, J=6.15 Hz, 1 H). MS: 673 (M+H$^+$).

58F

Example 58

To a mixture of 58E (10 mg) in EtOAc (0.5 mL) was added 4.0 M HCl in dioxane (0.4 mL, 100 equiv.). The mixture was stirred at rt for 6 h. After removal of solvent, 7.0 mg of 58F (Example 58) was obtained as a white solid. $^1$H NMR (400 MHz, CD$_3$OD) δ ppm 1.21 (d, J=6.15 Hz, 6 H) 1.30 (t, J=6.81 Hz, 3 H) 3.14 (m, 3 H) 3.99 (q, J=7.03 Hz, 2 H) 4.46 (m, 1 H) 5.06 (s, 1 H) 6.61 (d, J=2.20 Hz, 1 H) 6.81 (d, J=7.03 Hz, 1 H) 6.91 (d, J=8.35 Hz, 1 H) 6.98 (m, 1 H) 7.04 (d, J=1.76 Hz, 1 H) 7.10 (dd, J=9.23, 2.2 Hz, 1 H) 7.25 (d, J=7.03 Hz, 1 H) 8.02 (d, J=9.23 Hz, 1 H). MS: 473 (M+H$^+$).

We claim:

1. A compound according to formula (I),

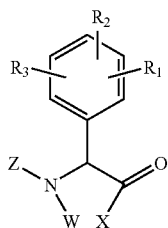

(I)

or a stereoisomer or a pharmaceutically-acceptable salt or hydrate thereof, wherein:

X is —NR$_6$S(O)$_p$R$_{16}$;

W is hydrogen or —(CR$_7$R$_8$)$_q$—W$_1$;

W$_1$ is hydrogen or may be taken together with R$_6$ to define a bond so that X and W are joined together to form a five to seven membered heterocyclic ring;

Z is isoquinolyl optionally substituted with 1–3 substituents selected from R$_9$ and/or R$_{10}$;

R$_1$, R$_2$ and R$_3$ are attached to any available carbon atom of the phenyl ring and are independently selected from hydrogen, halogen, cyano, nitro, C$_{1-10}$alkyl, C$_{2-10}$alkenyl, substituted C$_{1-10}$alkyl, substituted C$_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_t$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroary, cycloalkyl, and heterocyclo;

R$_6$ is hydrogen, C$_{1-4}$alkyl, NH$_2$, C$_{1-4}$alkylamino, hydroxy, or C$_{1-4}$alkoxy, or together with W$_1$ is a bond so that X and W join together to form a five to seven membered heterocyclic ring;

R$_7$ and R$_8$ are independently selected from hydrogen, —OR$_{18}$, —NR$_{18}$R$_{19}$, —NR$_{18}$SO$_2$R$_{20}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, sulfonamido, sulfonyl, and phenyl in turn optionally substituted with 1–3 of halogen, cyano, haloalkyl, haloalkoxy, nitro, hydroxy, C$_{1-4}$alkyl, C$_{1-4}$hydroxyalkyl, C$_{1-4}$alkoxy, amino, NH(C$_{1-4}$alkyl), N(C$_{1-4}$alkyl)$_2$, and C$_{1-4}$aminoalkyl;

R$_9$ and R$_{10}$ are independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and C$_{3-7}$cycloalkyl; wherein when R$_9$ or R$_{10}$ is selected from heterocyclo, heteroaryl, phenyl, and C$_{3-7}$cycloalkyl, each of said cyclic groups in turn is optionally substituted with up to three of C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

R$_{12}$, R$_{13}$, R$_{14}$, R$_{18}$, R$_{19}$, R$_{22}$ R$_{23}$, and R$_{24}$ are independently selected from hydrogen, alkyl, substituted alkyl, alkenyl, substituted alkenyl, aryl, heteroaryl, cycloalkyl, and heterocyclo;

R$_{15}$, R$_{20}$ and R$_{21}$ are independently selected from alkyl, substituted alkyl, alkenyl, substituted alkenyl, aryl, heteroaryl, cycloalkyl, and heterocyclo;

R$_{16}$ is alkyl, substituted alkyl, alkenyl, substituted alkenyl, aryl, heteroaryl, cycloalkyl, or heterocyclo;

p is 1 or 2;

q is 1, 2 or 3;

t is 1 or 2; and u is 1 or 2;

provided that: R$_1$, R$_2$, and R$_3$ are not all simultaneously hydrogen.

2. A compound according to claim 1, or a stereoisomer or a pharmaceutically-acceptable salt or hydrate thereof, wherein:

X is —NR$_6$S(O)$_p$R$_{16}$;

W is hydrogen or —(CH$_2$)$_q$—H;

Z is isoquinolyl optionally substituted with 1–3 substituents selected from R$_9$ and/or R$_{10}$;

R$_1$, R$_2$ and R$_3$ are attached to any available carbon atom of the phenyl ring and are independently selected from hydrogen, halogen, cyano, nitro, C$_{1-10}$alkyl, C$_{2-10}$alkenyl, substituted C$_{1-10}$alkyl, substituted C$_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_t$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroary, cycloalkyl, and heterocyclo;

R$_6$ is hydrogen;

R$_9$ and R$_{10}$ are independently selected from hydrogen, halogen, alkyl, substituted alkyl, haloalkyl, haloatkoxy, cyano, nitro, —S(=O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and C$_{3-7}$cycloalkyl; wherein when R$_9$ or R$_{10}$ is selected from heterocyclo, heteroaryl, phenyl, and C$_{3-7}$cycloalkyl, each of said cyclic groups in turn is optionally substituted with up to three of C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

R$_{12}$, R$_{13}$, R$_{14}$, R$_{18}$, R$_{19}$, R$_{22}$R$_{23}$, and R$_{24}$ are independently selected from hydrogen, alkyl, substituted alkyl, alkenyl, substituted alkenyl, aryl, heteroaryl, cycloalkyl, and heterocyclo;

$R_{15}$, $R_{20}$ and $R_{21}$ are independently selected from alkyl, substituted alkyl, alkenyl, substituted alkenyl, aryl, heteroaryl, cycloalkyl, and heterocyclo;

$R_{16}$ is alkyl, substituted alkyl, alkenyl, substituted alkenyl, aryl, heteroaryl, cycloalkyl, or heterocyclo;

p is 1 or 2;

q is 1, 2 or 3;

t is 1 or 2; and u is 1 or 2;

provided that: $R_1$, $R_2$, and $R_3$ are not all simultaneously hydrogen.

3. A compound according to claim 1, or a stereoisomer or a pharmaceutically-acceptable salt or hydrate thereof, wherein the compound is of formula (Ia):

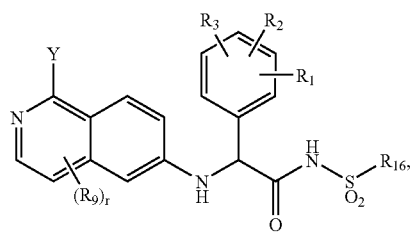

(Ia)

wherein:

Y is $NH_2$ or H;

$R_1$, $R_2$ and $R_3$ are attached to any available carbon atom of the phenyl ring and are independently selected from H, halogen, CN, $NO_2$, $C_{1-6}$alkyl, $C_{2-6}$alkenyl, substituted $C_{1-6}$alkyl, substituted $C_{2-6}$alkenyl, —C(=O)$NR_{12}R_{13}$, —$OR_{12}$—$CO_2R_{12}$, —C(=O)$R_{12}$, —$SR_{12}$, —S(=O)$_tR_{15}$, —$NR_{12}R_{13}$, —$NR_{12}SO_2R_{15}$, —$NR_{14}SO_2NR_{12}R_{13}$, —$NR_{12}CO_2R_{13}$, —$NR_{12}C(=O)R_{13}$, —$NR_{14}C(=O)NR_{12}R_{13}$, —$SO_2NR_{12}R_{13}$, aryl, heteroaryl, cycloalkyl, and heterocyclo;

$R_9$ is, independently at each occurrence, H, halogen, alkyl, substituted alkyl, haloalkyl, haloalkoxy, cyano, nitro, —S(O)$_uR_{21}$, —$NR_{22}SO_2R_{21}$, —C(=O)$NR_{22}R_{23}$, —$OR_{22}$, —$CO_2R_{22}$, —C(=O)$R_{22}$, —$SR_{22}$, —$NR_{22}R_{23}$, —$NR_{22}CO_2R_{23}$, —$NR_{22}C(=O)R_{23}$, —$NR_{22}C(=O)NR_{23}R_{24}$, —$SO_2NR_{22}R_{23}$, —$NR_{22}SO_2NR_{23}R_{24}$, five or six membered heterocyclo or heteroaryl, phenyl, or $C_{3-7}$cycloalkyl; wherein when $R_9$ is selected from heterocyclo, heteroaryl, phenyl, and $C_{3-7}$cycloalkyl, each of said cyclic groups in turn is optionally substituted with up to three of $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, and/or cyano;

$R_{16}$ is $C_{1-6}$alkyl substituted with 0–3 $R_{25}$, phenyl substituted 0–3 $R_{25}$, naphthyl substituted with 0–3 $R_{25}$, a 5–10 membered heteroaryl substituted with 0–3 $R_{25}$ and selected from 1H-pyrazol-4-yl, 1H-pyrazol-4-yl, thiazol-5-yl, 2-naphthyl, quinolin-8-yl, benzo[1,2,5]thiadiazol-4-yl, 2,3-dihydro-benzo[1,4]dioxin-5-yl, or 1H-benzoimidazol-5-yl;

$R_{25}$ is, independently at each occurrence, $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, cyano, carboxy, nitro, phenyl, —$SO_2NR_{22}R_{23}$, or —CO $NR_{22}R_{23}$; and r is 0 to 2.

4. A compound according to claim 3, or a stereoisomer or a pharmaceutically-acceptable salt or hydrate thereof, wherein the compound is of formula (Ib):

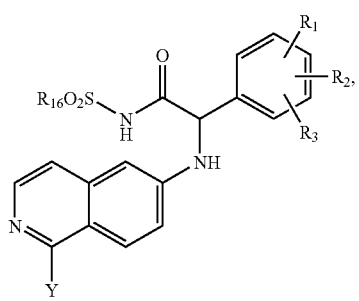

(Ib)

wherein:

Y is H or $NH_2$;

$R_{16}$ is Me, Et, Pr, i-Pr, cyclo-Pr, Bu, i-Bu, t-Bu, phenyl, 2-Me-phenyl, 3-Me-phenyl, 4-Me-phenyl, 2-F-phenyl, 3-F-phenyl, 4-F-phenyl, 2-OH-phenyl, 3-OH-phenyl, 4-OH-phenyl, 2-OMe-phenyl, 3-OMe-phenyl, 4-OMe-phenyl, 2-$CH_2$OH-phenyl, 3-$CH_2$OH-phenyl, 4-$CH_2$OH-phenyl, 2-$CO_2$H-phenyl, 3-$CO_2$H-phenyl, 4-$CO_2$H-phenyl, 3-$CONH_2$-phenyl, 4-$CONH_2$-phenyl, 3-$CO_2$H-4-OH-phenyl, 3-$SO_2NH_2$-phenyl, 4-$SO_2NH_2$-phenyl, 2-CN-phenyl, 3-CN-phenyl, 4-CN-phenyl, 3-$NO_2$-phenyl, 4-$NO_2$-phenyl, 2-$NH_2$-phenyl, 3-$NH_2$-phenyl, 4-$NH_2$-phenyl, 3-$CH_2NH_2$-phenyl, 4-$CH_2NH_2$-phenyl, 4-(2-$CH_2CH_2NH_2$)-phenyl, 4-(2-tert-butyl cabamoyl-ethyl)-phenyl, benzyl, 5-Cl-1,3-diMe-1H-pyrazol-4-yl, 5-Me-1-phenyl-1H-pyrazol-4-yl, 2,4-diMe-thiazol-5-yl, 2-naphthyl, Quinolin-8-yl, Benzo[1,2,5]thiadiazol-4-yl, 2,3-dihydro-benzo[1,4]dioxin-5-yl, 2-amino-1H-benzoimidazol-5-yl, hydroxymethyl, hydroxyethyl, hydroxypropyl, aminomethyl, aminoethyl, aminopropyl, 2,2,2-trifluoroethyl, 3-$SO_2NH_2$-propyl, 3-$CONH_2$-propyl, 2-$SO_2NH_2$-ethyl, 2-$CONH_2$-ethyl, 4-$SO_2NH_2$-butyl, or 4-$CONH_2$-butyl.

5. A compound according to claim 4, or a stereoisomer or a pharmaceutically-acceptable salt or hydrate thereof, wherein the compound is of formula (Ib) wherein $R_1$ and $R_2$ are $C_{1-4}$alkoxy.

6. A compound according to claim 1, or a steroisomer or a pharmaceutically-acceptable salt or hydrate thereof, wherein $R_1$ and $R_2$ are $OR_{12}$.

7. A compound according to claim 6, or a stereoisomer or a pharmaceutically-acceptable salt or hydrate thereof, wherein $R_{12}$ is hydrogen, $C_{1-6}$alkyl, phenyl, or benzyl optionally substituted with 1–2 halogen, cyano, haloalkyl, haloalkoxy, nitro, hydroxy, $C_{1-4}$alkyl, $C_{1-4}$hydroxyalkyl, $C_{1-4}$alkoxy, amino, NH($C_{1-4}$alkyl), and/or N($C_{1-4}$alkyl)$_2$.

8. A compound according to claim 1, or a stereoisomer or a pharmaceutically-acceptable salt or hydrate thereof, wherein W is hydrogen.

9. A compound according to claim 1, or a stereoisomer or a pharmaceutically-acceptable salt or hydrate thereof, wherein Z is selected from:

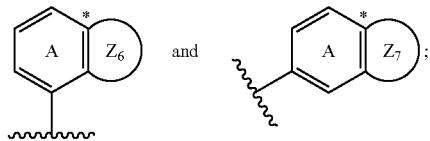

$Z_6$ is fused to ring A comprising the common carbon atom C* and is

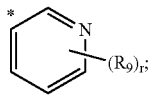

$Z_7$ is fused to ring A comprising the common carbon atom C* and is selected from:

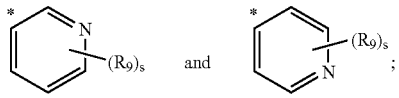

r is 0, 1, or 2; and
s is 0, 1, 2, or 3.

10. A compound according to claim 1, or a stereoisomer or a pharmaceutically-acceptable salt or hydrate thereof, wherein Z is selected from:

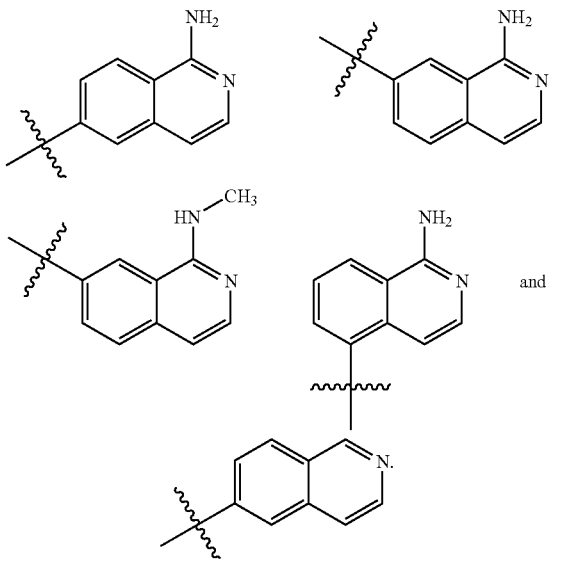

11. A compound according to claim 1, or a stereoisomer or a pharmaceutically-acceptable salt thereof, wherein the compound is of formula (Ic):

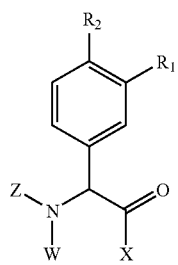

(Ic)

wherein:
X is —NR$_6$S(=O)$_p$R$_{16}$;
W is hydrogen or —(CH$_2$)$_q$—H;

Z is isoquinolyl optionally substituted with 1–3 substituents selected from R$_9$ and/or R$_{10}$;

R$_1$ and R$_2$ are independently hydrogen, halogen, cyano, nitro, C$_{1-10}$alkyl, C$_{2-10}$alkenyl, substituted C$_{2-10}$alkyl, substituted C$_{2-10}$alkenyl, —C(=O)NR$_{12}$R$_{13}$, —OR$_{12}$, —CO$_2$R$_{12}$, —C(=O)R$_{12}$, —SR$_{12}$, —S(=O)$_t$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, or heterocyclo;

R$_6$ is hydrogen or together with W is a bond so that X and W join together to form a five to seven membered heterocyclic ring;

R$_9$ and R$_{10}$ are independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and C$_{3-7}$cycloalkyl; wherein when R$_9$ or R$_{10}$ is selected from heterocyclo, heteroaryl, phenyl, and C$_{3-7}$cycloalkyl, each of said cyclic groups in turn is optionally substituted with up to three of C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

R$_{12}$, R$_{13}$, R$_{14}$, R$_{22}$ R$_{23}$, and R$_{24}$ are independently selected from hydrogen, alkyl, substituted alkyl, alkenyl, substituted alkenyl, aryl, heteroaryl, cycloalkyl, and heterocyclo;

R$_{15}$ and R$_{21}$ are independently selected from alkyl, substituted alkyl, alkenyl, substituted alkenyl, aryl, heteroaryl, cycloalkyl, and heterocyclo;

R$_{16}$ is C$_{1-6}$alkyl substituted with 0–2 R$_{25}$, phenyl substituted 0–3 R$_{25}$, naphthyl substituted with 0–3 R$_{25}$, a 5–10 membered heteroaryl substituted with 0–3 R$_{25}$ and selected from 1H-pyrazol-4-yl, 1H-pyrazol-4-yl, thiazol-5-yl, 2-naphthyl, quinolin-8-yl, benzo[1,2,5]thiadiazol-4-yl, 2,3-dihydro-benzo[1,4]dioxin-5-yl, or 1H-benzoimidazol-5-yl;

R$_{25}$ at each occurrence is selected from C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

p is 1 or 2;
q is 1, 2 or 3;
t is 1 or 2; and
u is 1 or 2.

12. A compound according to claim 1, or a stereoisomer or a pharmaceutically-acceptable salt thereof, wherein the compound is of formula (Id):

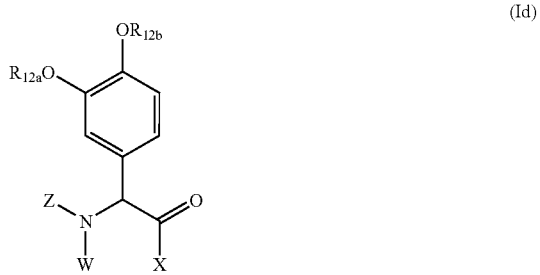

(Id)

97 wherein:

X is —NR$_6$S(O)$_p$R$_{16}$;

W is hydrogen or —(CH$_2$)$_p$—W$_1$;

W$_1$ is hydrogen or may be taken together with R$_6$ to define a bond so that X and W are joined together to form a five to seven membered heterocyclic ring;

Z is selected from:

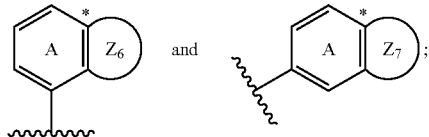

Z$_6$ is fused to ring A comprising the common carbon atom C* and is

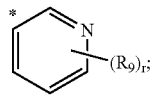

Z$_7$ is fused to ring A comprising the common carbon atom C* and is selected from:

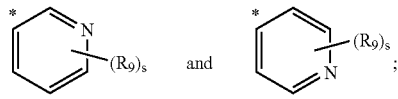

R$_6$ is hydrogen or together with W$_1$ is a bond so that X and W join together to form a five to seven membered heterocyclic ring;

R$_9$ is independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and C$_{3-7}$cycloalkyl, provided that R$_9$ is not —C(=NR$_{22}$)NR$_{23}$R$_{24}$ when W or W$_1$ is hydrogen; wherein when R$_9$ is independently selected from heterocyclo, heteroaryl, phenyl, and C$_{3-7}$cycloalkyl, each of said cyclic groups in turn is optionally substituted with up to three of C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylammo, and/or cyano;

R$_{12}$, R$_{12a}$, R$_{12b}$, R$_{22}$ R$_{23}$, and R$_{24}$ are independently selected from hydrogen, alkyl, substituted alkyl, alkenyl, substituted alkenyl, aryl, heteroaryl, cycloalkyl, and heterocyclo;

R$_{16}$ is C$_{1-6}$alkyl substituted with 0–2 R$_{25}$, phenyl substituted 0–3 R$_{25}$, naphthyl substituted with 0–3 R$_{25}$, a 5–10 membered heteroaryl substituted with 0–3 R$_{25}$ and selected from 1H-pyrazol-4-yl, 1H-pyrazol-4-yl, thiazol-5-yl, 2-naphthyl, quinolin-8-yl, benzo[1,2,5]thiadiazol-4-yl, 2,3-dihydro-benzo[1,4]dioxin-5-yl, or 1H-benzoimidazol-5-yl;

R$_{21}$ is selected from alkyl, substituted alkyl, alkenyl, substituted alkenyl, aryl, heteroaryl, cycloalkyl, and heterocyclo;

98

R$_{25}$ at each occurrence is selected from C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

p is 1 or 2;

q is 1, 2 or 3;

r is 0, 1, or 2;

s is 0, 1, 2, or 3;

t is 1 or 2; and u is 1 or 2.

13. A compound of claim 1, or a stereoisomer or a pharmaceutically-acceptable salt thereof, wherein the compound is of formula (Ie):

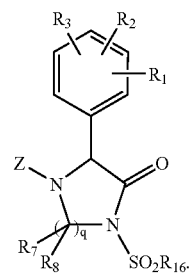

(Ie)

14. A compound of claim 13, or a stereoisomer or a pharmaceutically-acceptable salt thereof, wherein the compound is of formula (If):

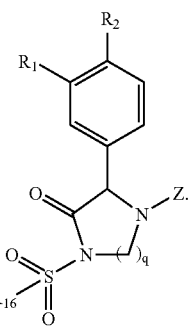

(If)

15. A compound according to claim 1, wherein the compound is selected from the group:

N-[2-(1-amino-isoquinolin-6-ylamino)-2-(3-ethoxy-4-isopropoxy-phenyl)-acetyl]-benzenesulfonamide;

N-[2-(1-amino-isoquinolin-6-ylamino)-2-(3-ethoxy-4-isopropoxy-phenyl)-acetyl]-4-hydroxy-benzenesulfonamide;

4-[2-(1-amino-isoquinolin-6-ylamino)-2-(3-ethoxy-4-isopropoxy-phenyl)-acetylsulfamoyl]-benzoic acid;

N-[2-(1-amino-isoquinolin-6-ylamino)-2-(3-ethoxy-4-isopropoxy-phenyl)-acetyl]-4-nitro-benzenesulfonamide;

N-[2-(1-amino-isoquinolin-6-ylamino)-2-(3-ethoxy-4-isopropoxy-phenyl)-acetyl]-C-phenyl-methanesulfonamide;

naphthalene-2-sulfonic acid [2-(1-amino-isoquinolin-6-ylamino)-2-(3-ethoxy-4-isopropoxy-phenyl)-acetyl]-amide;

N-[2-(1-amino-isoquinolin-6-ylamino)-2-(3-ethoxy-4-isopropoxy-phenyl)-acetyl]-4-methoxy-benzenesulfonamide;
4-amino-N-[2-(1-amino-isoquinolin-6-ylamino)-2-(3-ethoxy-4-isopropoxy-phenyl)-acetyl]-benzenesulfonamide;
3-[2-(1-amino-isoquinolin-6-ylamino)-2-(3-ethoxy-4-isopropoxy-phenyl)-acetylsulfamoyl]-benzoic acid;
N-[2-(1-amino-isoquinolin-6-ylamino)-2-(3-ethoxy-4-isopropoxy-phenyl)-acetyl]-4-methyl-benzenesulfonamide;
N-[2-(1-amino-isoquinolin-6-ylamino)-2-(3-ethoxy-4-isopropoxy-phenyl)-acetyl]-4-fluoro-benzenesulfonamide;
methanesulfonic acid [2-(1-amino-isoquinolin-6-ylamino)-2-(3-ethoxy-4-isopropoxy-phenyl)-acetyl]-amide;
ethane-1-sulfonic acid [2-(1-amino-isoquinolin-6-ylamino)-2-(3-ethoxy-4-isopropoxy-phenyl)-acetyl]-amide;
propane-2-sulfonic acid [2-(1-amino-isoquinolin-6-ylamino)-2-(3-ethoxy-4-isopropoxy-phenyl)-acetyl]-amide;
2-methyl-propane-2-sulfonic acid [2-(1-amino-isoqunolin-6-ylamino)-2-(3-ethoxy-4-isopropoxy-phenyl)-acetyl]-amide;
5-chloro-1,3-dimethyl-1H-pyrazole-4-sulfonic acid [2-(1-amino-isoquinolin-6-ylamino)-2-(3-ethoxy-4-isopropoxy-phenyl)-acetyl]-amide;
N-[2-(1-amino-isoquinolin-6-ylamino)-2-(3-ethoxy-4-isopropoxy-phenyl)-acetyl]-3-fluoro-benzenesulfonamide;
N-[2-(1-amino-isoquinolin-6-ylamino)-2-(3-ethoxy-4-isopropoxy-phenyl)-acetyl]-3-nitro-benzenesulfonamide;
benzo[1,2,5]thiadiazol-4-sulfonic acid [2-(1-amino-isoquinolin-6-ylamino)-2-(3-ethoxy-4-isopropoxy-phenyl)-acetyl]-amide;
quinoline-8-sulfonic acid [2-(1-amino-isoquinolin-6-ylamino)-2-(3-ethoxy-4-isopropoxy-phenyl)-acetyl]-amide;
3-amino-N-[2-(1-amino-isoquinolin-6-ylamino)-2-(3-ethoxy-4-isopropoxy-phenyl)-acetyl]-benzenesulfonamide;
2,4-dimethyl-thiazole-5-sulfonic acid [2-(1-amino-isoquinoln-6-ylamino)-2-(3-ethoxy-4-isopropoxy-phenyl)-acetyl]-amide;
5-methyl-1-phenyl-1H-pyrazole-4-sulfonic acid [2-(1-amino-isoquinoln-6-ylamino)-2-(3-ethoxy-4-isopropoxy-phenyl)-acetyl]-amide;
2,3-dihydro-benzo[1,4]dioxine-5-sulfonic acid [2-(1-amino-isoquinolin-6-ylamino)-2-(3-ethoxy-4-isopropoxy-phenyl)-acetyl]-amide;
N-[2-(1-amino-isoquinolin-6-ylamino)-2-(3-ethoxy-4-isopropoxy-phenyl)-acetyl]-2-nitro-benzenesulfonamide;
(2-{4-[2-(1-amino-isoquinolin-6-ylamino)-2-(3-ethoxy-4-isopropoxy-phenyl)-acetylsulfamoyl]-phenyl}-ethyl)-carbamic acid tert-butyl ester;
N-[2-(1-amino-isoquinolin-6-ylamino)-2-(3-ethoxy-4-isopropoxy-phenyl)-acetyl]-3-hydroxymethyl-benzenesulfonamide;
N-[2-(1-amino-isoquinolin-6-ylamino)-2-(3-ethoxy-4-isopropoxy-phenyl)-acetyl]-4-hydroxymethyl-benzenesulfonamide;
5-[2-(1-amino-isoquinolin-6-ylamino)-2-(3-ethoxy-4-isopropoxy-phenyl)-acetylsulfamoyl]-2-hydroxy-benzoic acid;
N-[2-(1-amino-isoquinolin-6-ylamino)-2-(3-ethoxy-4-isopropoxy-phenyl)-acetyl]-3-hydroxy-benzenesulfonamide;
N-[2-(1-amino-isoquinolin-6-ylamino)-2-(3-ethoxy-4-isopropoxy-phenyl)-acetyl]-2-hydroxy-benzenesulfonamide;
N-[2-(1-amino-isoquinolin-6-ylamino)-2-(3-ethoxy-4-isopropoxy-phenyl)-acetyl]-3-cyano-benzenesulfonamide;
N-[2-(1-amino-isoquinolin-6-ylamino)-2-(3-ethoxy-4-isopropoxy-phenyl)-acetyl]-3-methyl-benzenesulfonamide;
2-amino-N-[2-(1-amino-isoquinolin-6-ylamino)-2-(3-ethoxy-4-isopropoxy-phenyl)-acetyl]-benzenesulfonamide;
4-(2-amino-ethyl)-N-[2-(1-amino-isoquinolin-6-ylamino)-2-(3-ethoxy-4-isopropoxy-phenyl)-acetyl]-benzenesulfonamide;
4-aminomethyl-N-[2-(1-amino-isoquinolin-6-ylamino)-2-(3-ethoxy-4-isopropoxy-phenyl)-acetyl]-benzenesulfonamide;
3-aminomethyl-N-[2-(1-amino-isoquinolin-6-ylamino)-2-(3-ethoxy-4-isopropoxy-phenyl)-acetyl]-benzenesulfonamide;
2-amino-1H-benzoimidazole-5-sulfonic acid [2-(1-amino-isoquinolin-6-ylamino)-2-(3-ethoxy-4-isopropoxy-phenyl)-acetyl]-amide;
2-(1-aminoisoquinolin-6-ylamino)-2-(3-ethoxy-4-isopropoxyphenyl)-N-(2,2,2-trifluoroethylsulfonyl)acetamide;
2-(1-aminoisoquinolin-6-ylamino)-N-(cyclopropylsulfonyl)-2-(3-ethoxy-4-isopropoxyphenyl)acetamide;
2-(1-aminoisoquinolin-6-ylamino)-N-(3-aminosulfonylphenylsulfonyl)-2-(3-ethoxy-4-isopropoxyphenyl)acetamide;
2-(3-ethoxy-4-isopropoxyphenyl)-2-(isoquinolin-6-ylamino)-N-(phenylsulfonyl)-acetamide;
N-(3-cyanophenylsulfonyl)-2-(3-ethoxy-4-isopropoxyphenyl)-2-(isoquinolin-6-ylamino)acetamide;
N-(3-aminosulfonyl-phenylsulfonyl)-2-(3-ethoxy-4-isopropoxyphenyl)-2-(isoquinolin-6-ylamino)acetamide;
N-(cyclopropylsulfonyl)-2-(3-ethoxy-4-isopropoxyphenyl)-2-(isoquinolin-6-ylamino)acetamide;
N-(3-carboxamide-phenylsulfonyl)-2-(3-ethoxy-4-isopropoxyphenyl)-2-(isoquinolin-6-ylamino)acetamide;
N-(2-aminoethylsulfonyl)-2-(3-ethoxy-4-isopropoxyphenyl)-2-(isoquinolin-6-ylamino)acetamide;
2-(1-aminoisoquinolin-6-ylamino)-N-(3-carboxamidephenylsulfonyl)-2-(3-ethoxy-4-isopropoxyphenyl)acetamide;
2-(1-aminoisoquinolin-6-ylamino)-N-(3-carboxamidephenylsulfonyl)-2-(3-ethoxy-4-isopropoxyphenyl)acetamide; and
2-(1-aminoisoquinolin-6-ylamino)-2-(3-ethoxy-4-isopropoxyphenyl)-N-(methylsulfonyl)acetamide; or a stereoisomer or pharmaceutically acceptable salt thereof.

16. A pharmaceutical composition, comprising: a pharmaceutically acceptable carrier and a therapeutically effective amount of a compound of claim 1 or a pharmaceutically acceptable salt, or hydrate thereof.

17. A method for treating thrombosis, comprising: administering to a patient in need thereof a therapeutically effective amount of a compound of claim 1 or a pharmaceutically acceptable salt, or hydrate thereof.

18. A method according to claim 17, wherein the thrombosis is selected from the group consisting of arterial thrombosis, venous thrombosis, deep vein thrombosis and cerebral thrombosis.

19. A pharmaceutical composition, comprising: a pharmaceutically acceptable carrier and a therapeutically effective amount of a compound of claim 2, or a stereoisomer or a pharmaceutically-acceptable salt thereof.

20. A pharmaceutical composition, comprising: a pharmaceutically acceptable carrier and a therapeutically effective amount of a compound of claim 3, or a stereoisomer or a pharmaceutically-acceptable salt thereof.

21. A pharmaceutical composition, comprising: a pharmaceutically acceptable carrier and a therapeutically effective amount of a compound of claim 4, or a stereoisomer or a pharmaceutically-acceptable salt thereof.

22. A pharmaceutical composition, comprising: a pharmaceutically acceptable carrier and a therapeutically effective amount of a compound of claim 5, or a stereoisomer or a pharmaceutically-acceptable salt thereof.

23. A pharmaceutical composition, comprising: a pharmaceutically acceptable carrier and a therapeutically effective amount of a, compound of claim 6, or a stereoisomer or a pharmaceutically-acceptable salt thereof.

24. A pharmaceutical composition, comprising: a pharmaceutically acceptable carrier and a therapeutically effective amount of a compound of claim 7, or a stereoisomer or a pharmaceutically-acceptable salt thereof.

25. A pharmaceutical composition, comprising: a pharmaceutically acceptable carrier and a therapeutically effective amount of a compound of claim 8, or a stereoisomer or a pharmaceutically-acceptable salt thereof.

26. A pharmaceutical composition, comprising: a pharmaceutically acceptable carrier and a therapeutically effective amount of a compound of claim 9, or a stereoisomer or a pharmaceutically-acceptable salt thereof.

27. A pharmaceutical composition, comprising: a pharmaceutically acceptable carrier and a therapeutically effective amount of a compound of claim 10, or a stereoisomer or a pharmaceutically-acceptable salt thereof.

28. A method for treating thrombosis, comprising: administering to a patient in need thereof a therapeutically effective amount of a compound of claim 1, or a stereoisomer or a pharmaceutically acceptable salt thereof.

29. A compound of formula (IV):

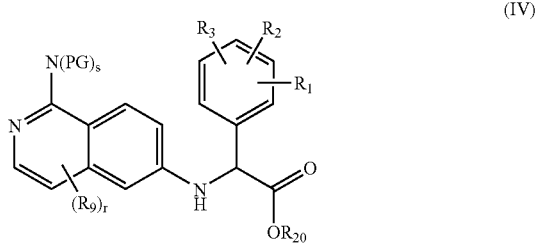

wherein $R_1$, $R_2$, $R_3$, and $R_9$ are defined as in claim 1; $R_{20}$ is $C_{1-4}$alkyl or benzyl; PG is a protecting group independently selected at each occurence from the group: formyl, benzyl, p-methoxybenzyl, nitrobenzyl, 2,4-dimethoxybenzyl, triphenylmethyl, di-p-anisylmethyl, furylmethyl, $C_{1-4}$alkoxycarbonyl, $C_{3-4}$allyloxycarbonyl, benzyloxycarbonyl, p-methoxybenzyloxycarbonyl, o-nitrobenzyloxycarbonyl, p-nitrobenzyloxycarbonyl, trimethylsilyl, t-Bu-diMe-silyl, $C_{1-4}$alkylidene, and benzylidene; r is 0, 1, or 2, and s is 1 or 2; when s is 2, both PG may be taken together with the nitrogen to which they are attached to form a phthalimide group.

30. A process for preparing a compound of claim 29, which comprises: contacting a compound of formula (II):

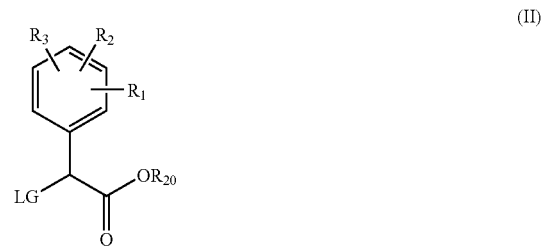

wherein LG is a leaving group selected from the group: halogen, mesylate, tosylate, benzenesulfonate, and trifluoromethanesulfonate;

with a compound of formula (III):

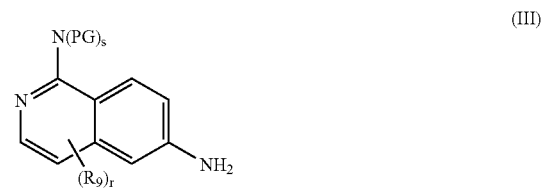

in the presence of a base selected from the group: diisopropylethylamine, triethylamine, potassium carbonate, potassium bicarbonate, and potassium phosphate.

31. A process according to claim 30, for preparing a compound of formula of (IVb):

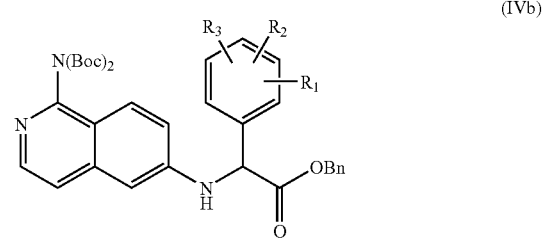

which comprises: contacting a compound of formula (II), wherein $R_{20}$ is benzyl;

with

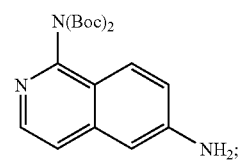

in the presence of diisopropyl ethyl amine.

32. A process for preparing a compound of claim 29, which comprises: contacting a compound of formula (V):

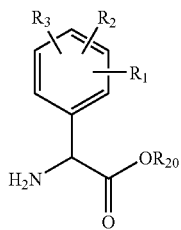
(V)

with a compound of formula (VI):

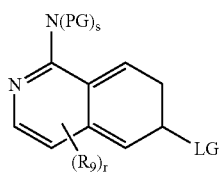
(VI)

in the presence of a palladium catalyst selected from the group: palladium (II) chloride, palladium (II) acetate, tris(dibenzylideneacetone)dipalladium (0), tetrakis (triphenylphosphine)palladium (0), bis(tri-t-butylphosphine)palladium(0), and allylpalladium chloride dimer; or a copper catalyst selected from the group: copper (III) triflate, tetrakis(acetonitrile)copper(I), hexafluorophosphate, copper(I) iodide, and copper (II) acetate; a ligand selected from the group: 1,1'-bis(diphenylphosphino)ferrocene, (R or S)-1-(2-diphenylphosphino-1-napthyl)isoquinoline, triphenylphosphine, triphenylarsine, 1,3-bis(2,4,6-trimethylphenyl)imidazolium chloride, tri-t-butylphosphine, tri-2-furylphosphine, (R or S)-2,2'-bis(diphenylphosphino)-1,1'-binapthyl (BINAP), (R or S)-2,2'-bis(di-p-tolylphosphino)-1,1'-binapthyl (Tol-BINAP), and N,N-diethylsalicylamide; and a base selected from potassium carbonate, potassium t-butoxide, tetrabutylammonium hydroxide, triethylamine, diisopropylethylamine, cesium carbonate, cesium acetate, and potassium phosphate.

\* \* \* \* \*